(12) United States Patent
Ziaie et al.

(10) Patent No.: US 9,999,369 B2
(45) Date of Patent: Jun. 19, 2018

(54) LASER-SCRIBED FERROGEL SENSOR WITH MAGNETIC PARTICLES

(71) Applicants: Purdue Research Foundation, West Lafayette, IN (US); Regents of the University of Minnesota, Minneapolis, MN (US)

(72) Inventors: Babak Ziaie, West Lafayette, IN (US); Ronald A. Siegel, Minneapolis, MN (US)

(73) Assignees: Purdue Research Foundation, West Lafayette, IN (US); Regents of the University of Minnesota, Minneapolis, MN (US)

( * ) Notice: Subject to any disclaimer, the term of this patent is extended or adjusted under 35 U.S.C. 154(b) by 576 days.

(21) Appl. No.: 14/557,247

(22) Filed: Dec. 1, 2014

(65) Prior Publication Data

US 2015/0087945 A1 Mar. 26, 2015

Related U.S. Application Data

(63) Continuation-in-part of application No. 13/800,860, filed on Mar. 13, 2013, now Pat. No. 9,737,244.
(Continued)

(51) Int. Cl.
*A61B 5/1455* (2006.01)
*A61B 5/05* (2006.01)
(Continued)

(52) U.S. Cl.
CPC .............. *A61B 5/05* (2013.01); *A61B 5/0031* (2013.01); *A61B 5/14503* (2013.01);
(Continued)

(58) Field of Classification Search
None
See application file for complete search history.

(56) References Cited

U.S. PATENT DOCUMENTS 6,201,980 B1 3/2001 Darrow et al.
6,310,387 B1 10/2001 Seefeldt et al.
(Continued)

OTHER PUBLICATIONS

Office Action for U.S. Appl. No. 13/800,860, dated Sep. 23, 2015, Babak Ziaie, Sensor Having Ferrogel With Magnetic Particles, 11 pages.
(Continued)

*Primary Examiner* — Eric Winakur
*Assistant Examiner* — Marjan Fardanesh
(74) *Attorney, Agent, or Firm* — Lee & Hayes, PLLC; Christopher J. White

(57) ABSTRACT

A method of making a sensor includes depositing a layer of hydrogel over a substrate, the hydrogel configured to change thickness or volume in response to a selected condition and including a plurality of magnetic particles disposed in the hydrogel so that a magnetic property of the hydrogel changes with changes of thickness or volume of the hydrogel. The hydrogel is sacrificed in selected region(s) of the layer so that the hydrogel outside the selected region(s) forms a plurality of spaced-apart islands of the hydrogel. The islands of the hydrogel are enclosed in an enclosure at least partly permeable to a selected fluid. A sensor for detecting a condition includes the substrate, islands, and a device coil arranged with respect to the hydrogel so that changes in the magnetic property modulate an electrical property of the sensor. A system includes the substrate, islands, and a magnetic-field detector.

25 Claims, 43 Drawing Sheets

Related U.S. Application Data

(60) Provisional application No. 61/910,414, filed on Dec. 1, 2013, provisional application No. 61/609,960, filed on Mar. 13, 2012.

(51) Int. Cl.
*A61B 5/145* (2006.01)
*G01R 3/00* (2006.01)
*A61K 9/00* (2006.01)
*A61K 9/06* (2006.01)
*A61K 47/32* (2006.01)
*A61B 5/00* (2006.01)

(52) U.S. Cl.
CPC ...... *A61B 5/14532* (2013.01); *A61B 5/14539* (2013.01); *A61K 9/0009* (2013.01); *A61K 9/06* (2013.01); *A61K 47/32* (2013.01); *G01R 3/00* (2013.01); *Y10T 29/49155* (2015.01)

(56) References Cited

U.S. PATENT DOCUMENTS

| | | |
|---|---|---|
| 6,480,730 B2 | 11/2002 | Darrow et al. |
| 6,750,311 B1 | 6/2004 | Van Antwerp et al. |
| 6,972,658 B1 | 12/2005 | Findley et al. |
| 2002/0032380 A1 | 3/2002 | Acker et al. |
| 2002/0115740 A1 | 8/2002 | Beuhler et al. |
| 2003/0028087 A1* | 2/2003 | Yuzhakov ......... A61B 5/14514 600/345 |
| 2005/0283094 A1* | 12/2005 | Thym ............... A61B 5/15142 600/583 |
| 2006/0264715 A1 | 11/2006 | Mir et al. |
| 2008/0242976 A1* | 10/2008 | Robertson .......... A61B 5/1107 600/425 |
| 2011/0312004 A1 | 12/2011 | Chinnayelka et al. |

OTHER PUBLICATIONS

Office Action for U.S. Appl. No. 13/800,860, dated Jun. 16, 2016, Ziaie et al., "Sensor Having Ferrogel With Magnetic Particles", 11 pages.

* cited by examiner

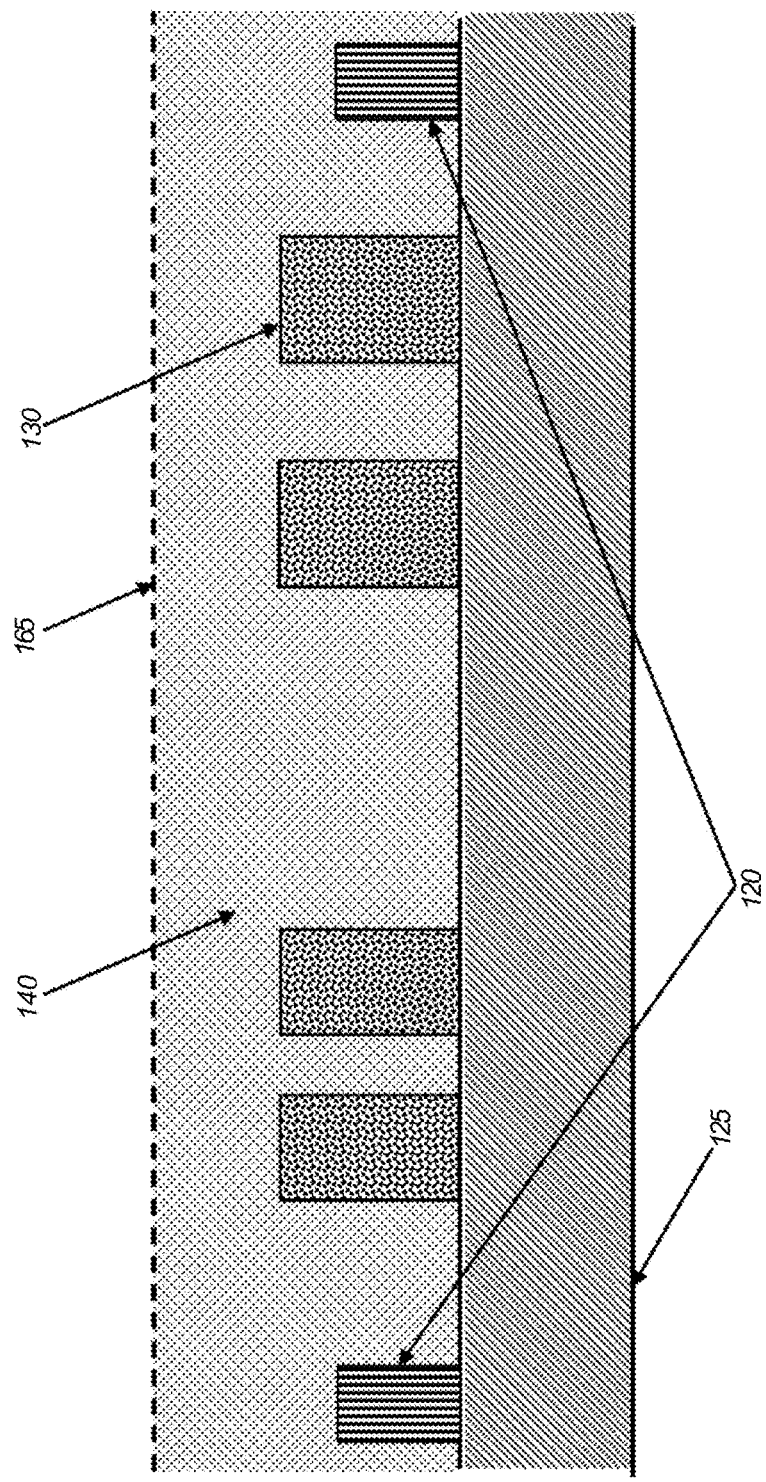

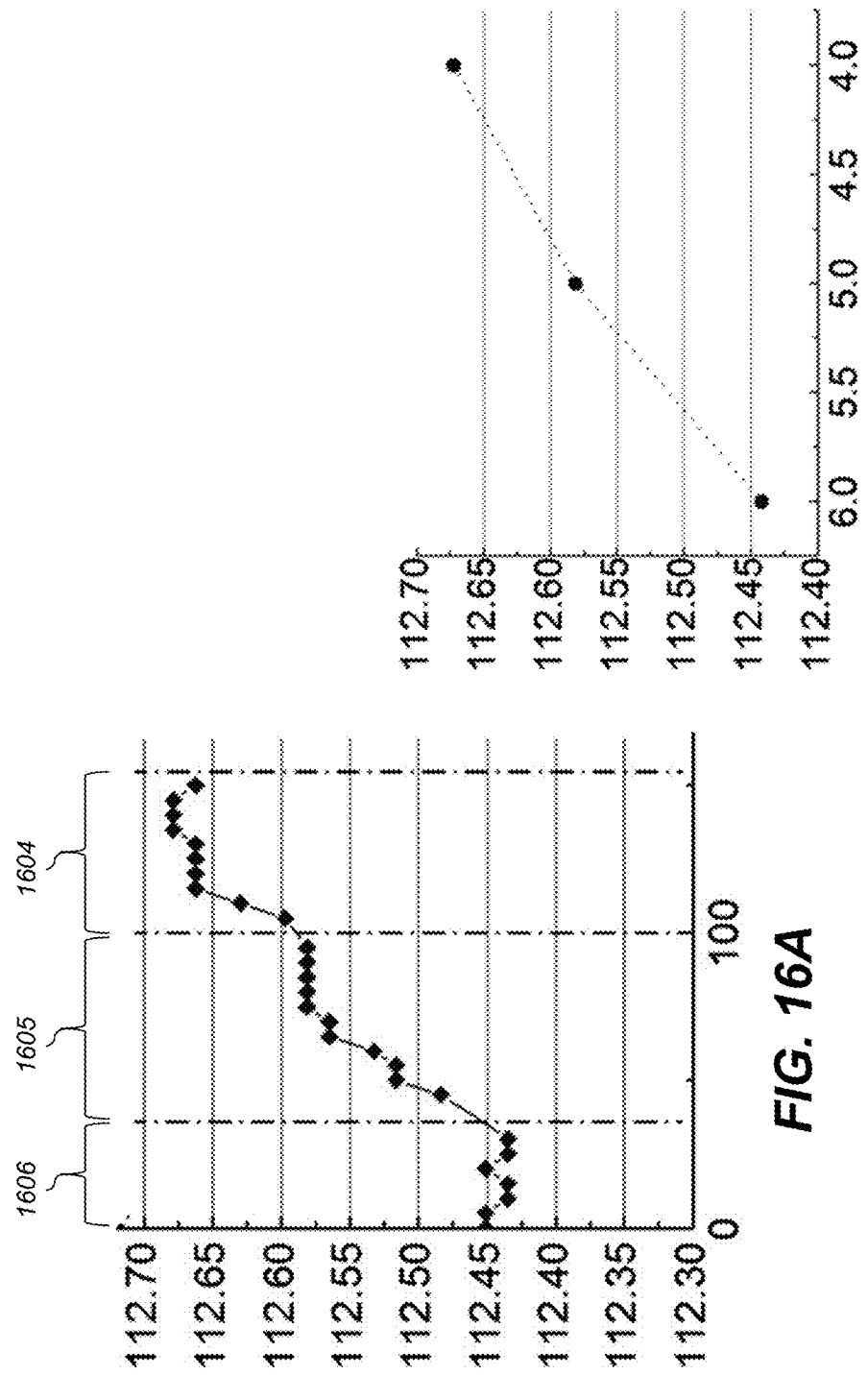

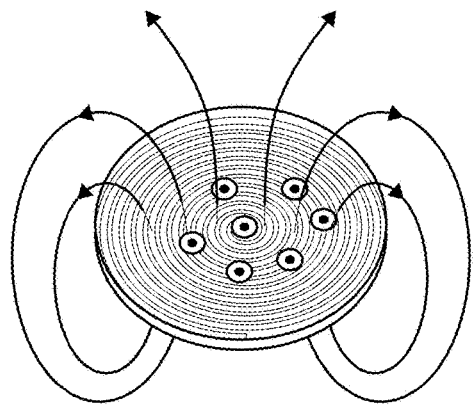
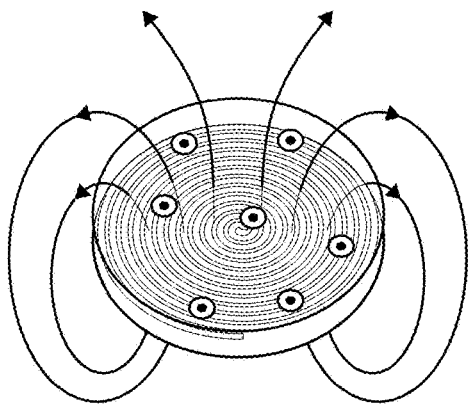
FIG. 17A          FIG. 17B
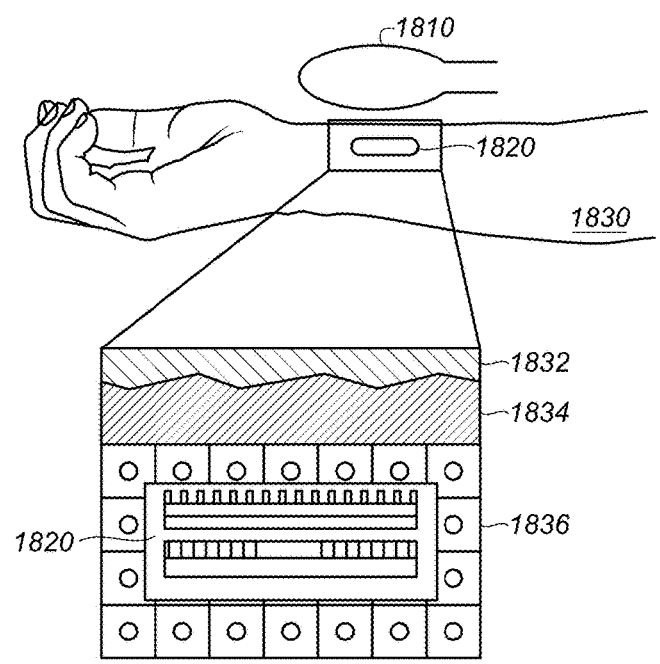
FIG. 18

POROUS MEMBRANE

COPPER

SI

PHOTO RESIST

POLYIMIDE

UV CURABLE GLUE

TRANSPARENCY FILM

GELBOND

FERROGEL

POLYCARBONATE MEMBRANE

GOLD

SI

POLYIMIDE

ALD OXIDE

FERROGEL

LASER-SCRIBED FERROGEL SENSOR WITH MAGNETIC PARTICLES

CROSS-REFERENCE TO RELATED APPLICATIONS

This application is a nonprovisional application of U.S. Provisional Application Ser. No. 61/910,414, filed Dec. 1, 2013 and entitled "Sensor Having Ferrogel Responsive to Changes in Chemical Environment in the Presence of a Magnetic Field," and is a continuation-in-part of U.S. patent application Ser. No. 13/800,860, filed Mar. 13, 2013 and entitled "Sensor having Ferrogel with Magnetic Particles," which is a nonprovisional application of U.S. Provisional Application Ser. No. 61/609,960, filed Mar. 13, 2012 and entitled "Sensor Having Ferrogel Responsive to Changes in Chemical Environment in the Presence of a Magnetic Field," the entirety of each of which is incorporated herein by reference.

STATEMENT OF FEDERALLY SPONSORED RESEARCH OR DEVELOPMENT

This invention was made with government support under Contract No. ECCS-1128169 awarded by the National Science Foundation. The government has certain rights in the invention.

TECHNICAL FIELD

The present disclosure generally relates to sensors, and in particular to a class of sensors responsive to changes in chemical, physical, or biological environment.

BACKGROUND

Environmentally sensitive hydrogels have been the focus of extensive investigation over the past several decades. These hydrogels may comprise crosslinked polymeric systems, and can be engineered to swell and shrink (de-swell) in response to a variety of physical, chemical, and biological stimuli. Hydrogels therefore can operate as transducers without the requirement for an on board power source. Much research and development in this area has been towards actuating systems in which a drug-embedded hydrogel can be directed to swell and release its payload in response to pH, temperature, magnetic field and other stimuli. Recently, environmentally sensitive hydrogels have been integrated with micromachined and MEMS structures in order to expand their capabilities by coupling them to hard inorganic materials. An example is described by Lei et al. in "A Hydrogel Based Implantable Micromachined Transponder for Wireless Glucose Measurement," Diabet. Technol. Therap. 2006; 8:112-22 (hereinafter "Lei"). In Lei, a glucose-sensitive hydrogel was coupled to the plate of a micromachined capacitive sensor. Specifically, swelling of the glucose-sensitive hydrogel described in Lei deflected the moving plate of a MEMS capacitor. The resonant frequency of a parallel LC circuit in which the capacitor was the sensing element thus changed with glucose concentration, permitting remote glucose measurement by monitoring that resonant frequency Such devices, however, require complicated fabrication processes, e.g., snug-filling of a small cavity with hydrogel. Some such sensors require being hermetically sealed against aqueous environments but still providing an electrical feedthrough. Sensors have also been developed that measure the pressure exerted by a hydrogel when it swells. Sensors have also been developed that measure temperature, pH and salt concentration, by combining a suitably sensitive hydrogel with a MEMS capacitor. Actuators have been developed that stimulate a hydrogel electromagnetically. Temperature changes generated inside the hydrogels by the electromagnetic fields, which can, e.g., heat superparamagnetic nanoparticles embedded in the hydrogel, cause swelling and shrinking of the hydrogels.

The past several decades have witnessed marked improvements in the understanding and treatment of diabetes mellitus, a disorder which affects millions in the U.S. and abroad, with increasing incidence nationally and internationally due to lifestyle changes. While acute mortality due to diabetes can be averted by regular paraprandial injections of insulin, long term morbidities due to chronic hyperglycemia (condition caused by high glucose levels) remain a challenge.

Diabetes refers to disorders in glucose homeostasis and hence energy storage and use by the body. There are two major types of diabetes. In Type I or juvenile onset diabetes, pancreatic beta cells, which normally would secrete insulin, a regulator of blood glucose level, are destroyed. Persons with Type I diabetes exhibit wide swings in blood glucose, including episodes of hyperglycemia (blood glucose too high) following meals. Over a life time, hyperglycemia can lead to degeneration of nerve, muscle, and connective tissue, with shortened life span and degraded quality of life. Blindness or loss of extremities can occur in extreme cases. Type I diabetes can be controlled by judicious injection of insulin, either through a syringe or a catheter connected to a wearable pump. Care should be taken, however, that insulin administration does not drive blood sugar level too low (hyperglycemia), as this may lead to disorientation, coma, or death. The Type I diabetic should therefore monitor his or her glucose level frequently to administer the correct amount insulin at the appropriate time.

In Type II or adult onset diabetes, insulin is not utilized properly to regulate blood glucose level. Type II diabetics cannot be treated by insulin alone, and a number of drugs have been developed to improve glucose homeostasis. Incidence of Type II diabetes has sharply increased both in the United States and internationally, primarily due to consumption of unhealthy foods and sedentary lifestyle. Diet and exercise are important regulators of glucose metabolism in treating Type II diabetes, and glucose monitoring may play an increasing role by providing "on-line" feedback to the patient and caregiver regarding these behavioral aspects.

Typically, patients monitor their blood glucose intermittently using a finger stick method. However, finger sticks are uncomfortable and provide time-separated, discrete observations of blood glucose level, which changes continuously as a function of time. Indeed, based on the current method of intermittent monitoring of glucose, some of the fluctuations, including sudden hypoglycemic episodes, can be missed.

Transcutaneous glucose electrodes generally pose challenges such as infection due to the transcutaneous nature of the sensors, enzyme denaturation in enzyme based sensors, degradation, and poisoning. Electrodes that rely on the enzymatic (glucose oxidase) oxidation of glucose and subsequent conversion to electric current, are presently used in commercial sensors, including CGMS Gold™ (Medtronic Minimed™), Seven™ (DexCom™), and Navigator™ (Abbott™/Therasense™), with FDA approval limited to one week use. While some of these challenges can be addressed by incorporating catalase, and while such electrodes represent a step forward in diabetes management, practical challenges remain, including the need for frequent (often daily) calibration against blood glucose obtained by finger-prick procedures.

Continuous Glucose Monitors (CGMs) can provide better management of glucose level. It is important for diabetic patient to identify fluctuations and trends in their glucose levels. This reduces the probability of emergency situations (e.g., hypoglycemic episodes, indicated by shaking, sweating, fast heartbeat, and impaired vision), particularly if monitoring is performed autonomously. However, current continuous glucose monitors have a number of disadvantages. They puncture the skin, need to be periodically replaced (as often as every week) and calibrated (as often as every 12 hours), restrict motion, are not waterproof (some can tolerate water but few or none can survive hot water), and are expensive.

Recently, an implantable glucose oxidase/catalase-based sensor was shown to reliably monitor glucose fluctuations in diabetic pigs for more than one year. In this disk-shaped system (diameter 3.4 cm, thickness 1.5 cm), the enzyme electrode was packaged with a battery and microelectronics for radiotelemetry. The sensor, implanted into tissue, exhibited short, 6-10 min "dynamic delays", i.e. latencies in tracking up- and downswings in blood glucose concentration. Delays were attributed primarily to mass transfer in tissue.

Glucose can be "sampled" by reverse iontophoresis across the skin and analyzed electrochemically. Glucowatch™, a product based on this concept, received FDA approval, but was withdrawn from the market due to skips in intermittent (20 min duty cycle) measurements and the need for daily calibration. Ultrasound followed by vacuum extraction across the skin and electrochemical detection, has also been proposed.

Blood glucose sensing by absorption and reflectance of near- and far-IR radiation, or by surface-enhanced Raman scattering (SERS), is under investigation. These optical techniques, while attractive since electromagnetic (EM) energy can be generated and sensed noninvasively, exhibit difficulties in establishing unambiguous correlation between signal and true blood glucose level due to interfering analytes and scattering by intervening tissues. They also require sophisticated, bulky, and expensive readout instrumentation.

In addition to glucose monitoring, detecting environmental changes, specifically chemical changes, has also received significant attention over the past few decades. Some of the sensors for detecting chemical changes are part of complex industrial systems.

There is, therefore, a continuing need for a simple system that allows detection of chemical environmental changes, and that overcomes challenges accompanied with present systems including the transcutaneous glucose electrodes and other systems described above. Continuous or substantially continuous monitoring can provide data that can be recorded, stored, locally analyzed, communicated over a network, studied for trends over time, and be used in a system with a feedback path to provide corrective actions when needed.

Continuous sensing, in conjunction with predictive algorithms, can improve guidance of these corrective actions to minimize episodes associated with conditions outside of normal ranges. The advantage of continuous monitoring may extend to Type II diabetes. Here, continuous monitoring of glucose concentration in the body can help physicians and patients evaluate pharmacologic and/or behavioral therapies.

BRIEF DESCRIPTION OF DRAWINGS

FIGS. 8A and 8B are embodiments of the implantable device having various coil-hydrogel structures.

FIG. 16A shows a time series of measured resonant frequency.

FIG. 16B shows the measured resonance frequency of the ferrogel sensor in response to step changes in pH.

FIG. 17A shows an example configuration of a ferrogel sensor in a magnetic field.

FIG. 17B shows an example configuration of a ferrogel sensor in a magnetic field.

FIG. 18 shows an example implantable sensor in a patient's arm.

Figure 1A:
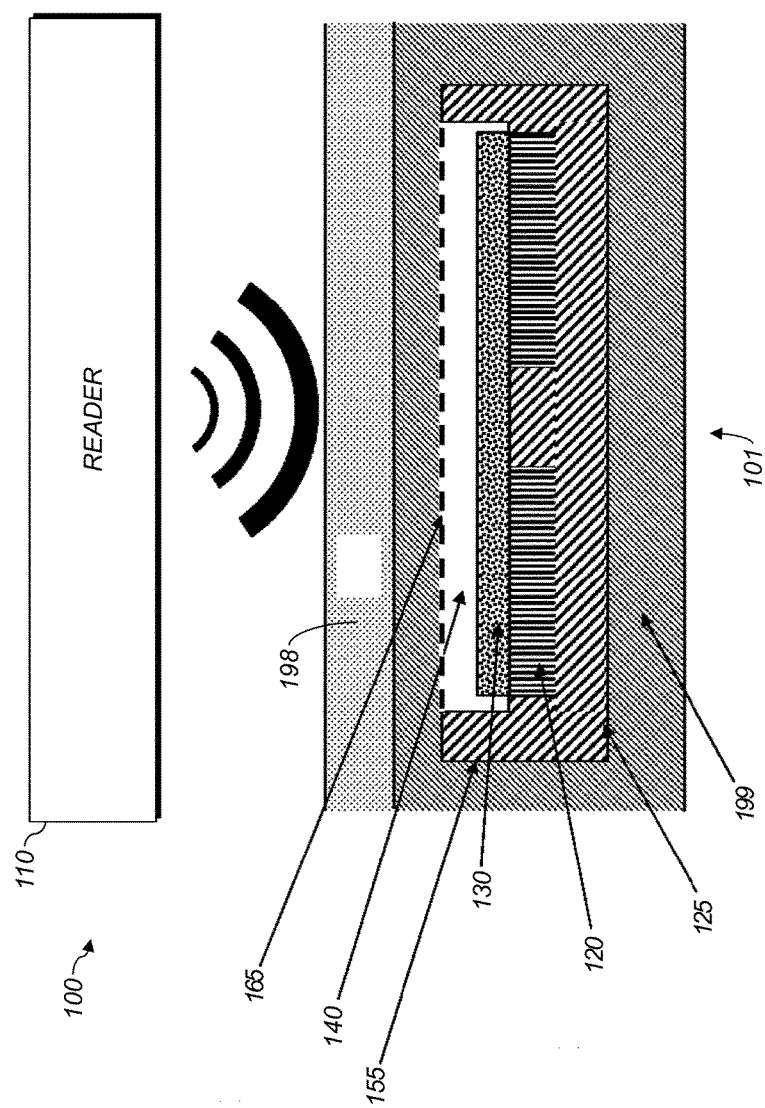
FIG. 1A is a schematic of a system illustrating an external electronic reader (transmitter/receiver) and an implantable device, according to various aspects.

The attached drawings are for purposes of illustration and are not necessarily to scale.

DETAILED DESCRIPTION

For the purposes of promoting an understanding of the principles of the present disclosure, reference will now be made to the embodiments illustrated in the drawings, and specific language will be used to describe the same. It will nevertheless be understood that no limitation of the scope of this disclosure is thereby intended.

A system having an environmental sensor is disclosed. The system includes a sensor assembly including a base. A fluid-swollen crosslinked polymer gel member (a "hydrogel") is positioned over the base and includes magnetic particles. The hydrogel with magnetic particles is also referred to as "ferrohydrogel" or "ferrogel"). A membrane is coupled to the base and positioned over the ferrogel member. References herein to "hydrogel" in the context of electrical or magnetic properties refer to ferrogels.

Some sensors described herein include an embedded conductive coil or "device coil" positioned adjacent the ferrogel member. The membrane is configured to allow passage of fluid across the membrane and into contact with the ferrogel member and to block particles of a predetermined size or electrical charge, e.g., proteins and cells, suspended in the fluid. The ferrogel member is configured to swell and shrink when the ferrogel is in contact with the fluid, responsive to physical or chemical changes in the fluid. Swelling and deswelling alters the magnetic permeability of the hydrogel, or other magnetic properties thereof, by changing the density of the magnetic particles therein. This change in permeability can be remotely detected in various ways. In various embodiments, the magnetic permeability of the ferrogel is detected using the Hall effect. In other embodiments, the magnetic-permeability change of the ferrogel is detected using a superconducting quantum interference detector (SQUID). In other embodiments, the ferrogel is configured to modulate inductance and self-resonant frequency of a combination of the device coil and the ferrogel as the gel swells and shrinks. In some such embodiments the system further includes an external coil configured to excite the device coil. Systems according to various aspects are configured to detect changes in at least one of temperature, glucose, pH, concentration of urea, sugars, metal ions, concentration of salts, or concentrations of other chemicals.

A physical or chemical monitoring system is disclosed. The system includes an external electronic reader (transmitter/receiver) and a sensor. The sensor includes a ferrogel configured to change one of thickness and volume, or both, in response to changes in physical variables such as temperature, or in concentrations of chemicals in the environment of the sensor. The external reader is configured to communicate with an electronic reader to determine inductance and capacitance of the sensor.

A sensor that can provide continuous readout of temperature or chemical concentration is disclosed herein. A wireless chemical environment monitoring system to continuously monitor chemical levels in a subcutaneous space is disclosed herein. Various sensors herein include a hydrogel.

Example hydrogels include a water swollen polymer network containing chemical groups that are sensitive to an environmental stimulus. When the stimulus is physical, e.g., a change in temperature, the polymer interacts with water such that the hydrogel swells or shrinks Swelling and shrinking can also result from a chemical interaction between an analyte of interest and a moiety that is incorporated within the polymer network. In either case, volume change can be regarded as a signal transduction, or in some cases, as an amplification.

As used herein, the term "condition" refers generally to something that can be measured or transduced with a hydrogel. Examples of conditions include physical properties such as temperature or pH and presence or absence of an analyte, either chemical or biochemical. Conditions can be discrete-valued (e.g., is a certain level of glucose present or not?) or analog (e.g., what is the pH?).

Since hydrogels typically are highly hydrated, they provide an essentially aqueous environment allowing ready access of analyte to the sensing moiety. In various aspects a particular type of hydrogel, which includes co-immobilized molecules and/or nano-objects designed to assist in reporting the presence of the analyte, is used. Changes in the characteristics of the hydrogel due to stimuli, e.g., changes in thermal or chemical environment, can be detected by monitoring the hydrogel. Application of a magnetic field to a sensor including the hydrogel can be used to ascertain changes in the hydrogel.

Devices and systems disclosed herein can be used to provide a wireless and battery-less biomedical sensor and accompanying system that can monitor physiological variables such as pH and glucose concentration. These targets are relevant to diabetes. Various aspects can be used for pH or glucose sensing and monitoring. Other aspects of systems and sensors herein are general platforms for detection of other analytes, physiological or otherwise, and other chemical or thermal environments.

The sensor can be microfabricated to have area less than about 1 cm$^2$ and a thickness less than about 1 mm. The sensor can be implanted, e.g., in an outpatient clinic, and following healing it can be configured to function for months or years without a need for replacement.

Various aspects provide an implantable wireless glucose sensor. This is a small wireless sensor implanted under the skin with an external system to readout results. This can advantageously significantly reduce the risk of infection due to skin puncture. In an example, a wireless reader is incorporated in a watch and a ferrogel sensor is implanted into the user's arm under the wrist. Wearing the watch therefore is all that is required to perform continuous glucose monitoring.

Compared to existing CGM sensors (~25 mm×~50 mm), various aspects are as small as 2 mm×2 mm×200 µm, and are suitable for implantation. Various aspects have long working lifetimes and so do not need to be replaced weekly. Once implanted, the sensor does not move, unlike some prior sensors in which movement of the sensor due to body motion compromises the integrity of the measurements.

In various aspects, a wireless transponder for measurement of glucose in biological milieus includes a planar inductor or coil fabricated on a substrate. A glucose sensitive ferrogel (hydrogel plus magnetic micro- or nano-particles) is immobilized and patterned on top of the inductor. The inductor and ferrogel are packaged inside a hard-shell container and separated from body fluids by a nanoporous membrane. In various aspects, the swelling and shrinking of the ferrogel result in a change in inductance which can be measured from outside the body using an interrogator ("reader"). In various aspects, the inductor (coil) is patterned on a polymer, metallic, or ceramic substrate. In various aspects, the container includes polymer, metal, or ceramic. In various aspects, the ferrogel is patterned in various shapes using micro-fabrication methods in order to improve its performance.

FIG. 1A shows a schematic for a system according to various aspects. Various aspects operate with electromagnetic fields in the radio-frequency (RF) range. The system 100 includes an external electronic reader 110 and a microsensor 101 including a microresonator circuit (including coil 120 and hydrogel 130, discussed below). The external electronic reader 110 can be a receiver or a transmitter/receiver (transceiver). In addition, the external reader 110 can be coupled to the microsensor 101 via a wire, or utilize a wireless configuration.

The microresonator circuit includes device coil(s) 120 embedded in a substrate 125, covered by a chemical environmentally sensitive, swellable ferrogel 130. The hydrogel 130 is of a type that includes paramagnetic or superparamagnetic nanoparticles ("SPNs"). This circuit has a substantially constant capacitance, C. The capacitance is a function of coil 120 geometry and properties of the substrate 125. The inductance, L, of the device coil depends on coil(s) 120 geometry (e.g. number of turns). The inductance also depends on the swelling of the hydrogel 130, since the ferrite nanoparticle density and ferrogel thickness governs the magnetic permeability. Hence, the resonant frequency depends on temperature and/or concentration of a chemical:

$$f_{res} = \frac{1}{2\pi\sqrt{LC}} \tag{1}$$

where $f_{res}$ is the resonant frequency, L is the inductance, and C is the capacitance. L, C, and $f_{res}$ are examples of electrical properties of the microsensor 101.

Resonant frequency can be detected by detecting a dip in impedance to radio frequency (RF) energy provided by an external coil 111 coupled to a frequency analyzer in reader 110 (FIG. 1b), or by using a phase lock-in circuit connected to the external coil 111 to lock in to the resonant frequency. It should be appreciated that the external electronic reader 110 depicted in FIG. 1A represents either of these approaches, which are referred to generically as "resonance detectors." The implantable device 101 according to various aspects requires no internal power source, battery, or internal data processing circuit. As a result, packaging of the implantable device is simplified.

Figure 12:
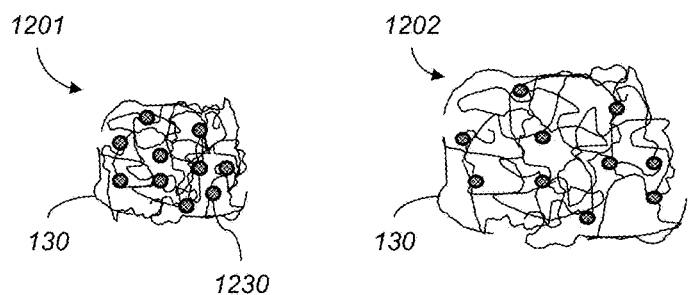
FIG. 12 shows an example of internal structure of a ferrogel.

FIG. 12 shows an example of internal structure of a ferrogel. The ferrogel 130 is prepared by randomly dispersing superparamagnetic ferroparticle-embedded polystyrene beads throughout the network before polymerization. The ferroparticles are thus physically trapped in the polymer network. Poly (methacrylic acid-co-acrylamide) (MAA-co-AAm) pH-sensitive hydrogels can be used. In this example, an increase in pH drives the ferrogel towards state 1202, and a decrease in pH drives the ferrogel towards state 1201.

In various aspects, the inductance of the sensor (e.g., microsensor 101, FIG. 1A) is altered by two competing mechanisms. As the ferrogel expands, the density of SPNs 1230 reduces, while the length of magnetic flux lines passing through the ferrogel sheet increases. Overall, the effect of longer magnetic flux pathway coupled with the SPNs prevails over lower SPN density, and the inductance of the sensor increases as the ferrogel swells. This increased inductance results in a lower resonant frequency of the sensor.

In FIG. 1A, a cross sectional view of the inductor (coil 12) is depicted. The inductor is a planar device coil, best depicted in FIG. 2D as described below, with terminals positioned outside and inside the device coil. The device coil can be an inductor in a microchip or an inductor printed on a plastic substrate.

Figure 1B:
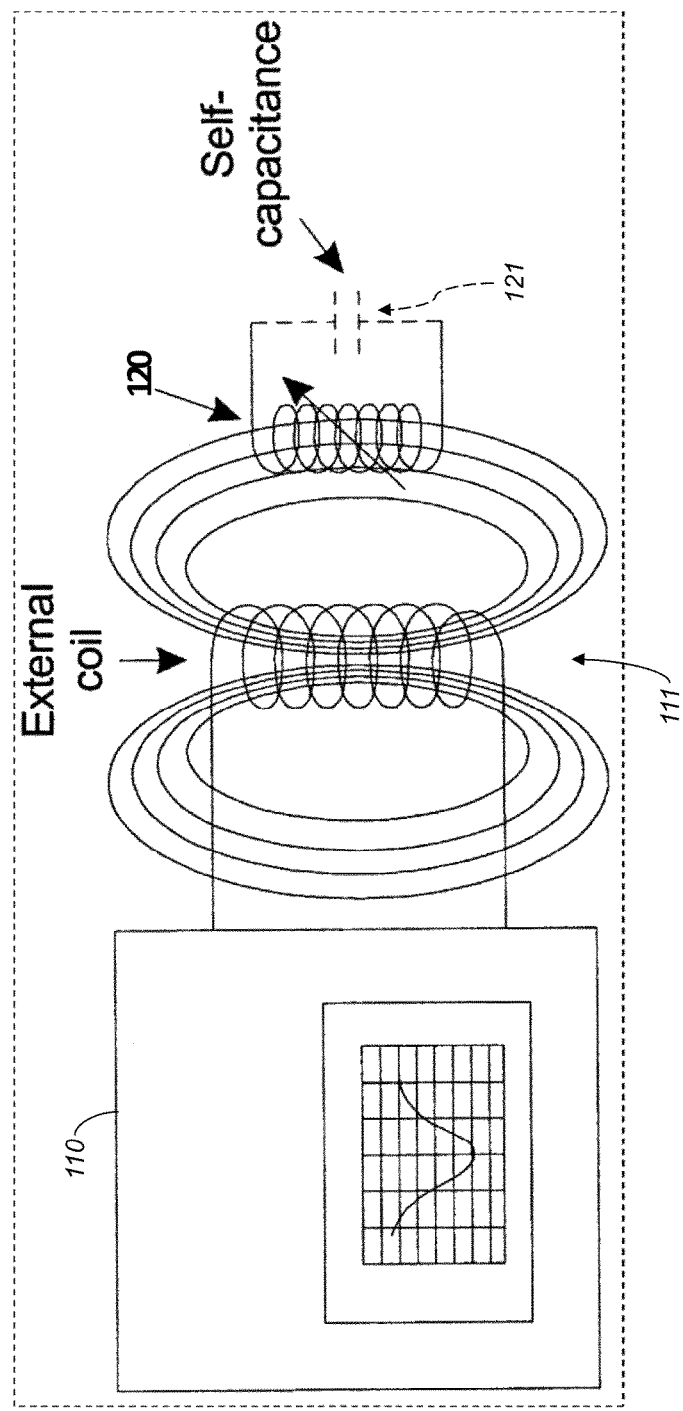
FIG. 1B is an electrical-magnetic schematic of the system of FIG. 1A.

The concept of energizing the microresonator circuit which includes a coil or coils 120 (L) and a capacitance 121 (C) is demonstrated in FIG. 1B. Radio frequency (RF) energy supplied by a power source (e.g., as discussed below with reference to FIG. 1C) in the electronic reader via the external coil, as shown, excites the microresonator circuit.

As depicted in FIG. 1B, the external coil can be configured to broadcast a signal. The signal is picked up by the device coil(s) of the implantable device. The impedance of the implantable device, partially defined by the L and the C, affects the broadcast signal and the effect is picked up by the impedance analyzer or the phase lock-in circuit described above (which would be part of the external electronic reader shown in FIG. 1A). The device coil(s) in the implantable device magnetically couples to the external coil and becomes part of the circuit which includes the external coil.

Figure 1C:
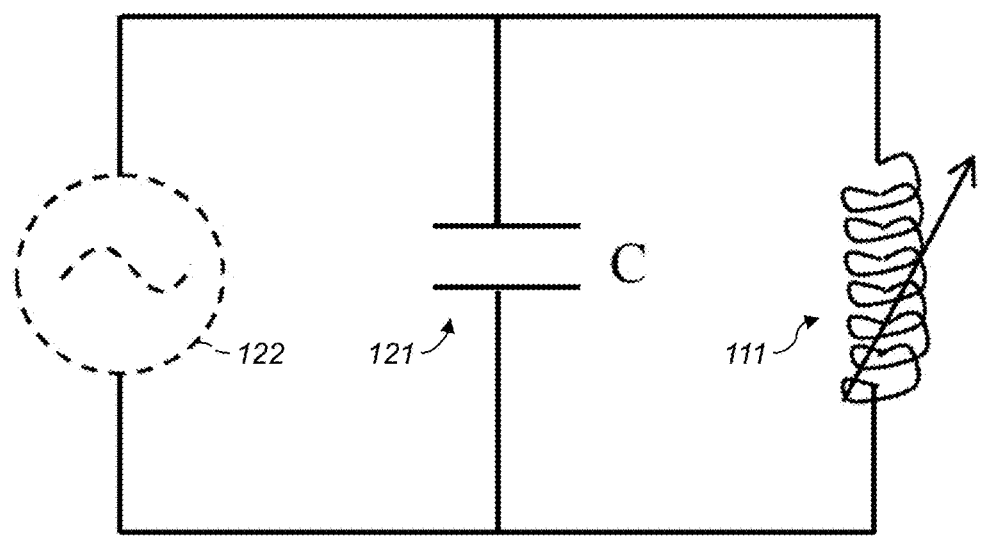
FIG. 1C is an electrical schematic showing a model of the implantable device depicted in FIG. 1A.

Referring to FIG. 1C an electrical model is presented. It should be noted that while there may be electrical resistance between various components, such resistance is not shown in FIG. 1C. The model includes a power source 122 that can be used to excite the passive elements of the implantable device. The source is shown in phantom since it is possible to have a system that does not include a source where a Hall-effect type sensor is used to sense movement of magnetic particles embedded in the hydrogel when the hydrogel swells and shrinks, as described further below. The capacitor 121 can be the parasitic capacitance of the structure depicted in FIG. 1A or an actual capacitor (not shown) coupled to the device coils. The variable inductance of external coil 111 includes device coils 120 and the hydrogel 130 with ferromagnetic particles embedded therein. On the one hand the ferromagnetic particles may be non-magnetized (i.e., the particles do not generate a magnetic field without being excited, thereby requiring the source shown in phantom) or magnetized (i.e., the particles generate a magnetic field without being excited, used with a Hall-effect type sensor or SQUID). Changes in glucose or other chemical environment can result in changes in the hydrogel 130 height which can result in changes in the inductance (i.e., lumped inductance resulting from the device coils 120 and the hydrogel 130 with embedded ferromagnetic particles), resulting in changes in natural (resonant) frequency of the implantable device. In summary, this is $\Delta$Glucose$\rightarrow\Delta$h$\rightarrow\Delta$L$\rightarrow\Delta f_{res}$. Thermally sensitive devices work in a similar manner, but with a temperature-sensitive hydrogel in place of the chemically-sensitive hydrogel.

The changes in the natural frequency can be detected using an electronic reader. Various schemes can be used to detect changes in the natural frequency of the implantable device. One method can be based on a phase dip measured at the input terminals of the external coil as a function of frequency occurring at the natural frequency of the implantable device. Another method can be based on a phase-lock scheme, where an external transceiver transmits a pulse near the natural frequency of the implantable device, and examines a reflected pulse from the implantable device. Measuring phase shift in the reflected signal can provide information about the natural frequency.

The implantable (subcutaneous or intraperitoneal) microsensor which can operate without internal batteries or data processing circuitry, as depicted in FIG. 1A, is now described. The device includes a PBA-based ferrogel and does not involve enzymes or electrochemical reactions, so its mechanism of action is inert to surrounding tissues. Once implanted, chemical concentration dependent swelling of the ferrogel can be interrogated continuously and wirelessly. The combination of small size and wireless operation provides advantages over sensors that are commercially available or are under research and development. Various aspects advantageously operate in the absence of enzyme-mediated bioelectrochemistry, permitting them to be used in a wider range of settings than other sensors. In various aspects, enzymes are incorporated into the device, providing a mechanism for chemical to mechanical transduction. Various aspects are inert to surrounding tissues and have long-term stability of sensitivity.

In the microsensor of FIG. 1A, inductance (L) varies due to swelling and shrinking of the chemical concentration sensitive ferrogel, which alters magnetic permeability just above the device coil and distorts magnetic flux lines. The capacitance (C) is set by electrical polarizability (characterized by dielectric constant) between device coil turns, and between the device coil and the substrate. Device coil geometry, e.g. distance between turns will also affect capacitance. Capacitance can be substantially unaffected by the ferrogel, and can be assumed constant provided fluid does not substantially invade the substrate and device coil volumes.

In the microsensor depicted in FIG. 1A, the hydrogel 130 is bonded on one end to the substrate, it is therefore configured to swell freely in the "vertical" direction, and not completely filling fluid space 140 (or other cavity), as depicted in the figure. Substantially none of the solid state elements of the sensor are deflected by hydrogel swelling, so considerations of mechanical strength are less important in the microsensor depicted in FIG. 1A. Also depicted is a ring 155 that is coupled to the substrate 125, e.g., continuously or by welding, which is used to support and hold a membrane 165. The microsensor is placed in the testing environment 199, e.g., under the skin 198 in contact with the intercellular fluid. The ring defines a fluid space 140 between the membrane 165 and the substrate 125. Within the fluid space, the hydrogel is free to swell and shrink when it comes in contact with chemical stimuli of varying concentrations.

Figure 2A:
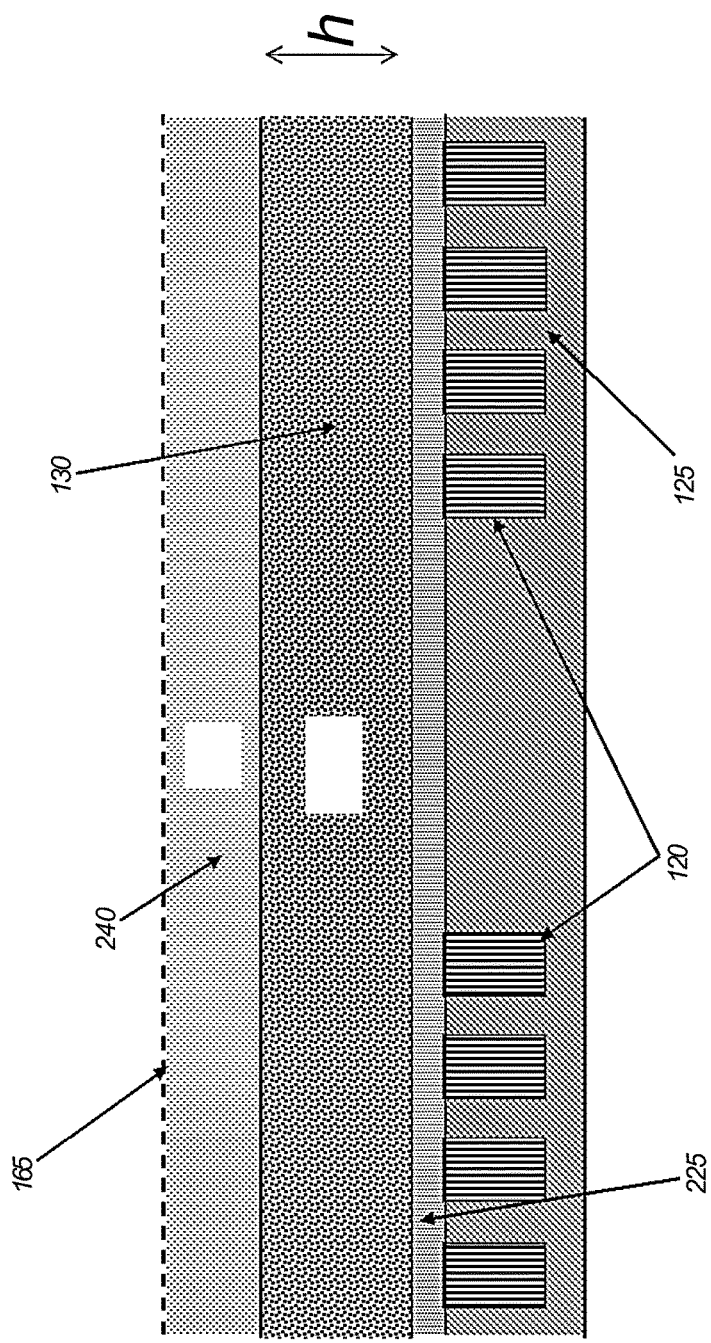
FIG. 2A is a cross-sectional schematic view of the implantable device of FIG. 1A, depicted in a first state responsive to a first concentration of a chemical environment.
Figure 2B:
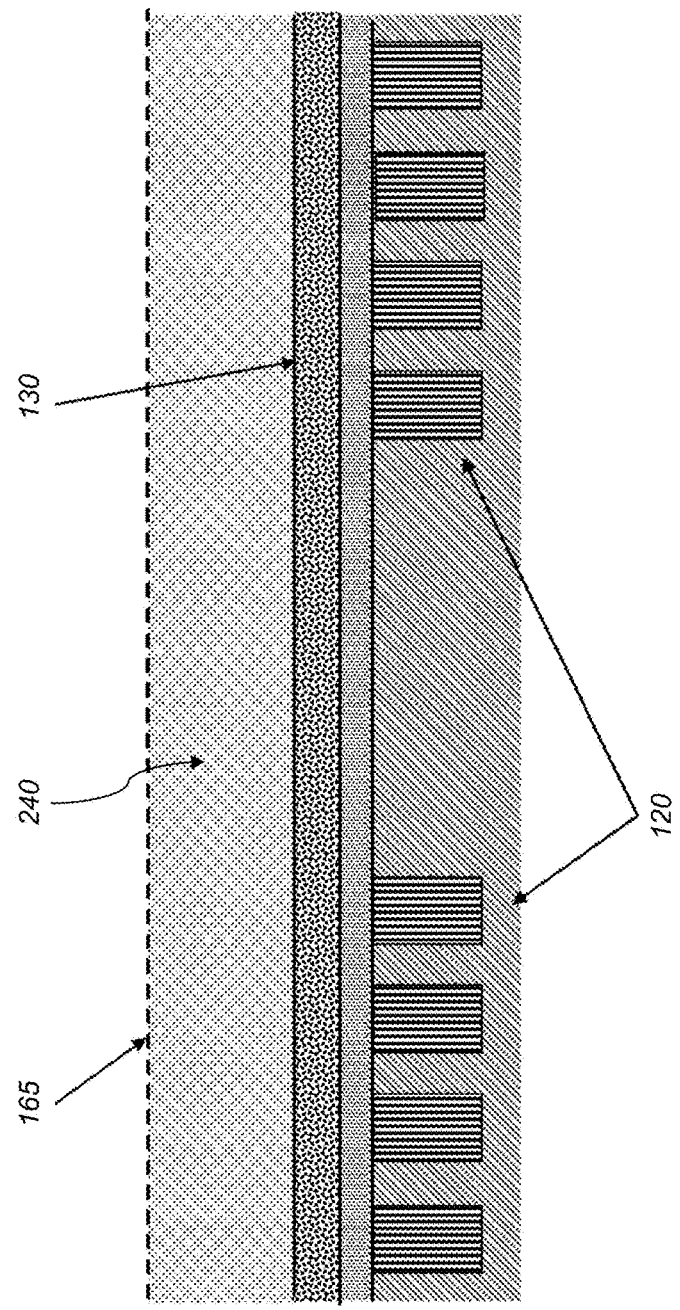
FIG. 2B is a cross-sectional schematic view of the implantable device of FIG. 1A, depicted in a second state responsive to a second concentration of the chemical environment.

FIG. 2A is a cross sectional schematic of the microsensor of FIG. 1A, further depicting the substrate 125, the device coil 120, and the hydrogel 130. The device coil 120 includes conductive material (e.g., metal) embedded in an insulating dielectric substrate 125, and is coated on top with a thin, waterproof insulating layer 225 (e.g., polyimide). The hydrogel 130 is bonded on top of the waterproof insulating layer 225 (or other coating) and extends into a fluid space 140 (FIG. 1A) below the membrane 165. Because of bonding, changes in hydrogel swelling are manifested by a change in hydrogel thickness, h, from an initial "reference" thickness, $H_0$. The hydrogel contains immobilized $Fe_3O_4$ nanoparticles, hence the term "ferrogel". Because the ferroparticles are para- or superparamagnetic, the magnetic permeability, g, of the ferrogel varies according to a function $\mu(h)=\mu_0+\Delta\mu(\theta_0 h_0/h)$, where $\theta_0$ is the loading (v/v) of ferroparticles in the initial hydrogel configuration, and $\mu_0$ is the permeability of free space, which also applies to the non-magnetic structures above and below the ferrogel. The inductance of the whole system, and hence and resonant frequency, will depend on h, $\mu(h)$, and the geometry and number of coil windings. Thus when the hydrogel swells or shrinks in response to a change in chemical concentration, thereby altering $\mu$, h, and L, (the effect as depicted FIG. 2B—hydrogel 130 is much thinner than in FIG. 2A), and resonant frequency ($f_{res}$) changes in response thereto.

Figure 2C:
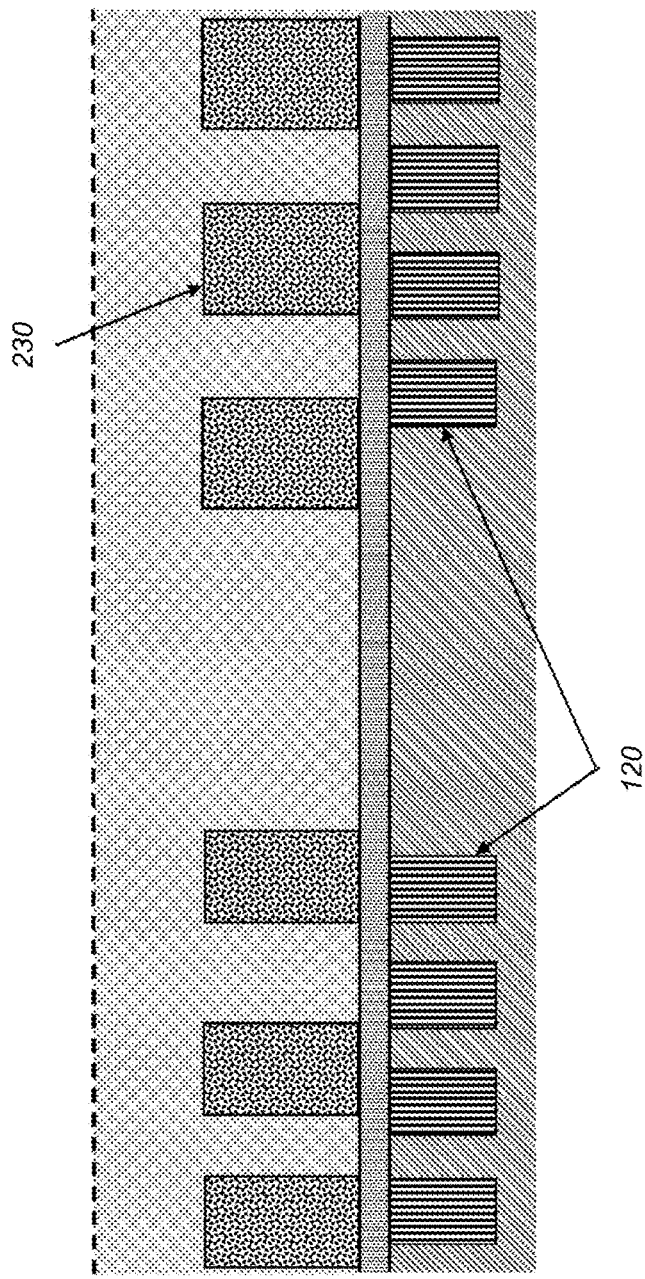
FIG. 2C is a cross-sectional schematic view of an alternative embodiment of the implantable device of FIG. 1A.

Referring to FIG. 2C, this changing-frequency effect also occurs if the ferrogel 230 is patterned on the surface as an array of narrow columns, which can swell/shrink more rapidly than a flat sheet hydrogel of equal thickness (as depicted in FIG. 2C) would be able to. Hydrogels can also be made highly porous, thereby increasing mass transfer and hence speed of response. Thin cylindrical hydrogel columns are likely to swell and shrink more rapidly, as are porous hydrogels. Device coils 120 are as shown in FIG. 1A.

Figure 2D:
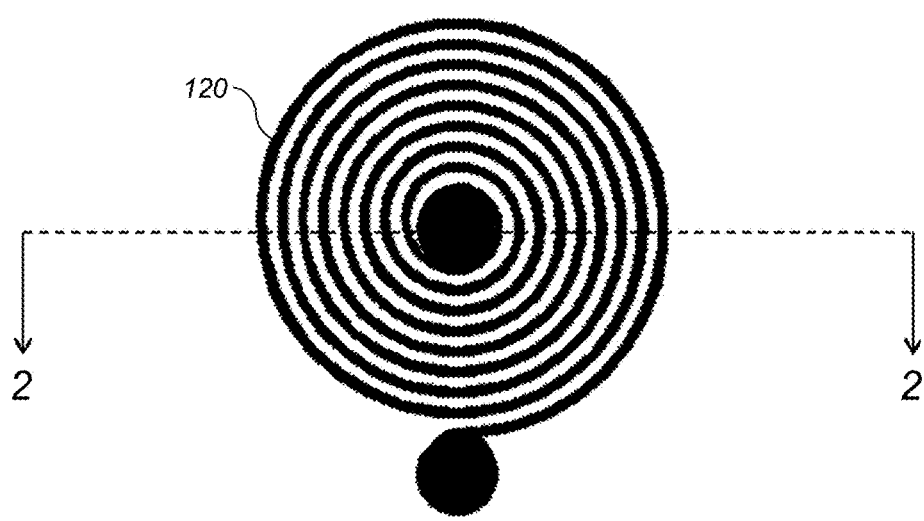
FIG. 2D is a top view of a device coil, a cross sectional view of which is depicted in FIG. 1A.

Referring to FIG. 2D, a top view of the device coils shown in previous schematics is provided. The reader should appreciate that the previous schematics, e.g., FIG. 1A, depict the device coil in a cross sectional view along line 2-2 shown in FIG. 2D. As shown in FIG. 2D, the terminals 220 of the device coil 120 are open (not mechanically connected to other components). The capacitance of the self-resonant circuit is the parasitic capacitance of the inductor coils themselves, as described above with respect to FIG. 1C, forming a parallel-resonant structure.

Magnetic permeabilities above and below the ferrogel (as depicted in FIG. 2A) will be substantially constant and equal to permeability of free space, $\mu_0$. Magnetic permeability $\mu$ of the ferrogel depends on volume fraction of inclusions, which decreases inversely with increasing h. Inductance L and hence resonant frequency are determined by $\mu$ and h.

The effects of h and $\mu(h)$ on L are due to magnetic polarization of the ferroparticles, which distorts the magnetic flux lines generated by the impinging electromagnetic field. Flux lines, currents, and inductances can be predicted, as a function of relevant parameters, using finite element multiphysics programs such as COMSOL™. Measured magnetic permeability of the ferrogels at different swelling degrees can also be modeled by, for example, the Bruggeman effective medium equation.

Figure 3A:
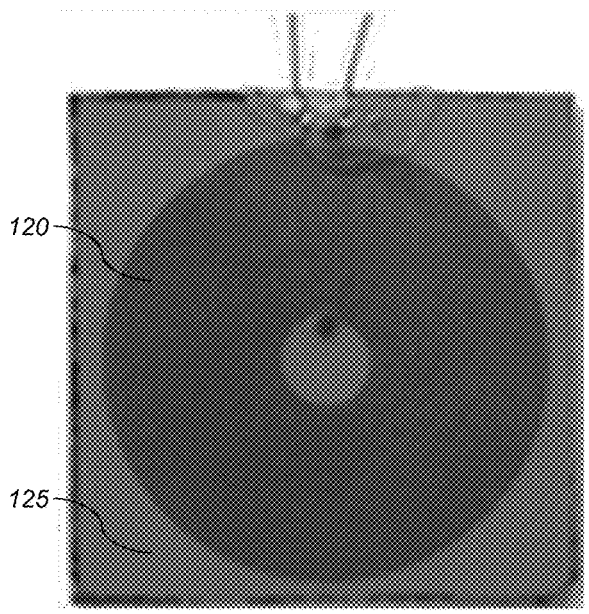
FIG. 3A is a representation of a photograph of a planar copper coil imbedded in insulating polyimide (PI) formed as a substrate.
Figure 3B:
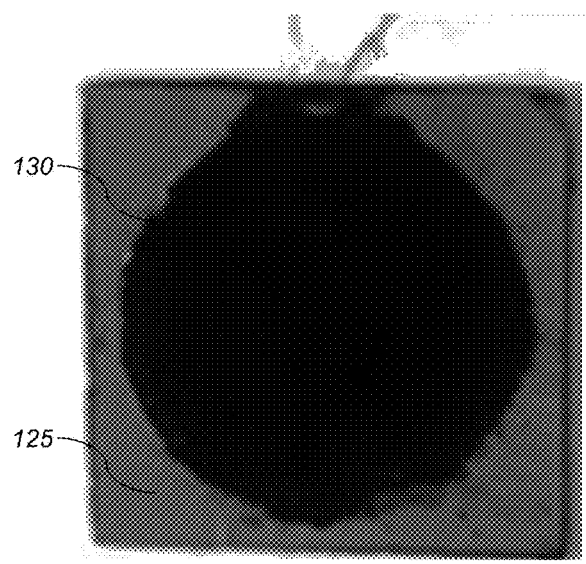
FIG. 3B is representation of a photograph of a ferrogel layer bonded to the planar copper coil of FIG. 3A.

FIG. 3A shows a device coil 120 on a substrate 125. In a simple preliminary experiment, a planar copper coil imbedded in insulating polyimide (PI) formed the substrate (as depicted in FIG. 3A). FIG. 3B shows the ferrogel 130 cured on top of the substrate 125. The ferrogel included poly (methacrylic acid-co-acrylamide) (MAA/AAm, 10 mol % MAA) loaded with surfactant-coated 10 nm ferroparticles at 5% volume concentration. Thickness of the ferrogel was controlled by applying weight on top during polymerization. Ferrogel was initially dried to ~50 µm thickness, and water was added on top in steps of 2 µl, causing stepwise swelling and increase in hydrogel thickness by ~6.5 µm/drop. Resonant frequency of the coil was recorded using an impedance analyzer.

Figure 3C:
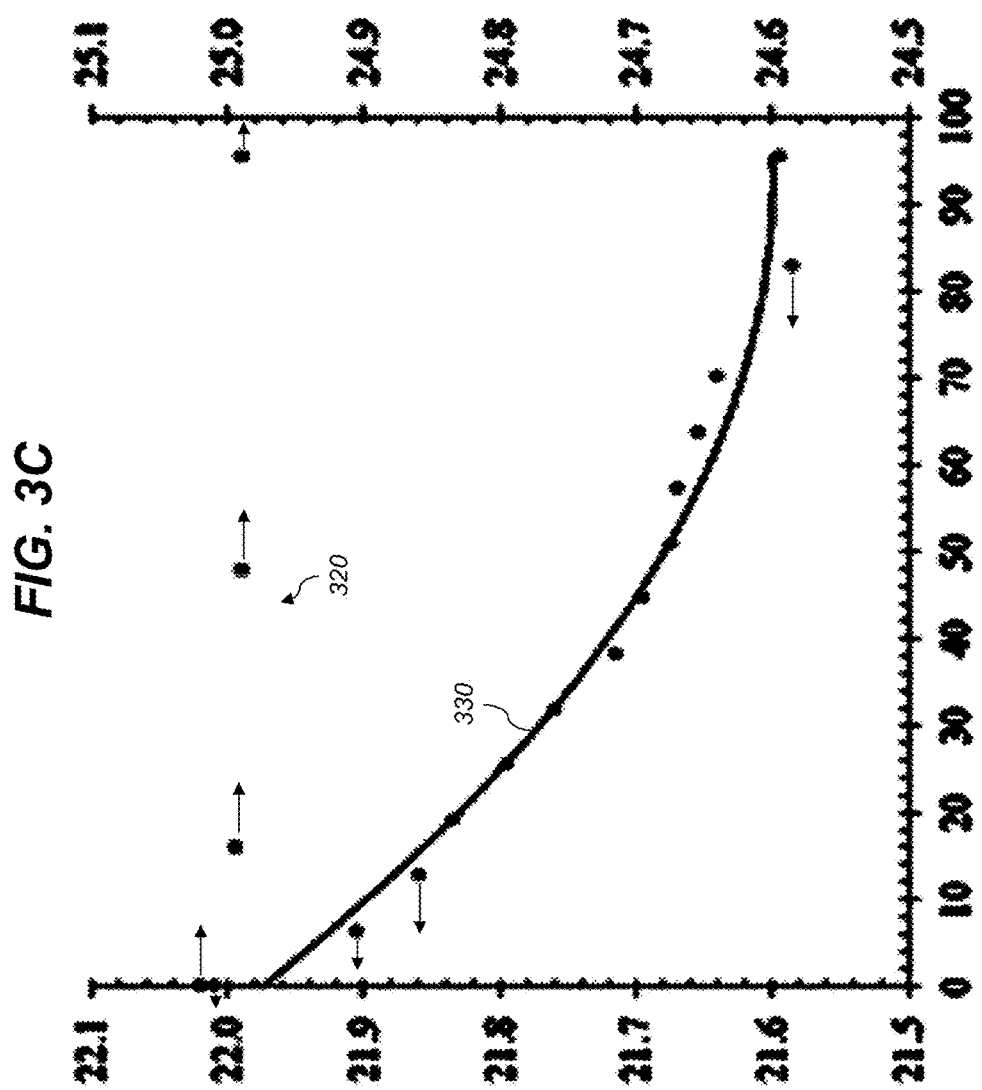
FIG. 3C is a graph of resonant frequency versus increase in thickness of the ferrogel over the coil assembly depicted in FIGS. 3A and 3B, and comparative data for a non-magnetically active hydrogel.

FIG. 3C shows the recorded $f_{res}$ plotted against estimated thickness of the gel. The abscissa is increase in thickness in µm. Each ordinate is resonant frequency in MHz. For the initial 50 µm thickness change, the sensitivity is about 5.6 kHz/µm, which can be detected by an impedance analyzer. The solid curve 330 represents a quadratic fit through the corresponding data points. Curve 330 and its data points correspond to the left ordinate (as indicated by the short arrows). A control hydrogel without ferroparticles did not exhibit any change in resonant frequency with swelling. This is shown by points 320, corresponding to the right ordinate (as indicated by the short arrows).

In a second experiment, latex beads including $Fe_3O_4$ superparamagnetic nanoparticles, dispersed in a polystyrene matrix and coated with surfactant (ProMag™, Bangs Laboratories: 1 µm diameter), were suspended in an aqueous pregel solution containing poly (methacrylic acid-co-acrylamide) (MAA/AAm, 5 mol % MAA), crosslinker and initiator. The suspension was polymerized onto the substrate, producing a ferrogel that completely covered the coil film, and bonded covalently to a GelBond® PAG sheet, trapping the coil. The ferrogel was dried and determined to be approximately 20 µm thick in its dry state.

Following rehydration of the hydrogel, this construct was tested in aqueous buffers at varying pH values. Starting from "rest" at pH 4, where the charge density of the ferrogel was low, the devices were exposed to solutions of progressively higher pH, charging the ferrogel and causing it to swell. The following shifts (as depicted in FIG. 3D) in resonant frequency were observed after exposure for 10 minutes: pH 5, $\Delta f_{res}$=0.05 MHz; pH 6, $\Delta f_{res}$=0.07 MHz; pH 7, $\Delta f_{res}$=0.10 MHz; pH 12, $\Delta f_{res}$=0.186 MHz.

Figure 3D:
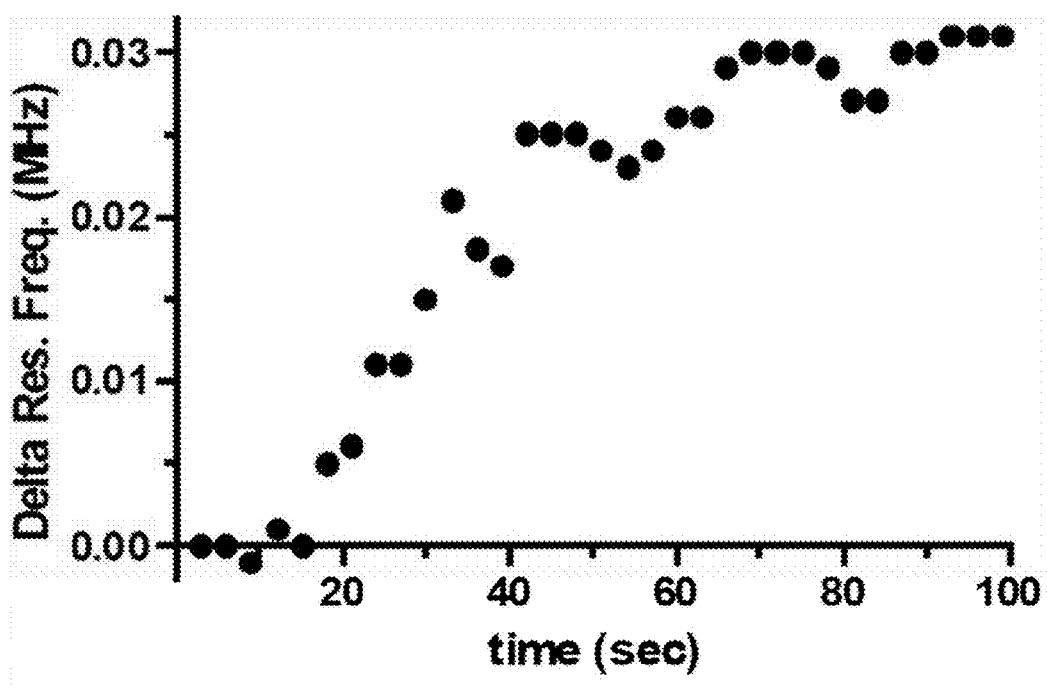
FIG. 3D is graph of change in natural frequency $\Delta f_{res}$ as a function of time.

FIG. 3D demonstrates rapid response, complete within ~70 sec, when the aqueous medium was step changed from pH 4 to pH 9. An initial "dead time" of 20 sec was observed. With increasing pH, the hydrogel swells, reducing the density of SPNs near the coil and hence magnetic permeability. Consequently, inductance decreases and resonant frequency increases. These results suggest that with further development, useful sensors can be produced using to SPN/hydrogel/microresonator approach.

The microsensor device depicted in FIGS. 1A and 2A includes a substrate that can be a commercially available plastic material such as polystyrene (PS), polymethylmethacrylate (PMMA), or polyimide (PI). PS is an attractive starting point since its glass transition temperature, $T_g$, is relatively low (~70° C.), enabling pressing operations with mild heating and cooling. A simple, batch preparation scheme carried out on a 4" diameter, 300-500 µm thick commercial polystyrene wafer, permits the fabrication of numerous devices in parallel, each of which can be about 1 $cm^2$ in diameter.

The process to fabricate the microsensor devices depicted in FIGS. 1A and 2A may include steps of patterning and electroplating gold (10-15 µm thick) device coils on the wafer surface, spin coating a 20 µm thick polystyrene layer on top, and covering the gold device coils to generate the sensor "base". An array of devices can be fabricated in parallel using common micro fabrication techniques.

Following the generation of the base, under a suitable pattern mask, plasma-treated PS coating can be applied followed by creating free radicals on non-masked parts of the surface. Under the same mask, by photopolymerization, a thin (~50 µm thick) ferrogel layer on activated surface can be generated. The recipe for the ferrogel can be varied, by altering magnetic nanoparticle inclusion loading, monomers used, monomer concentrations, and crosslinker concentrations. Following polymerization, the hydrogel is temporarily dried down onto the base.

The next step is separating parallel devices by laser cutting. Then for each device, a laser-cut washer (W) of PS of, e.g., 100 µm thickness can serve as a "frame," which is heat pressed onto the base. A suitable membrane (M), such as Anopore™, is then cut and heat pressed on top of the frame. Finally, the device is moved into a vacuum chamber and the hydrogel chamber is filled with water by gravity feed though the top membrane.

A proof-of-concept microsensor can be generated which can involve thermo- and pH-sensitive hydrogels, such as poly(N-isopropylacrylamide) and poly(acrylamide-co-methacrylic acid), respectively. $Fe_3O_4$ nanoparticles can be incorporated either by covalently linking to the network through vinylized surfactant coatings, or suspended in latex beads that are physically entrapped in the hydrogel network, as described above. Structure of the ferronanoparticle/hydrogel composite can be determined by a transmission electron microscope (TEM).

Thin hydrogels can be synthesized anchored to the resonator, on the plasma activated surface, as described above. Swelling ($h/h_0$) of the hydrogels as a function of stimulus (temperature, T, or pH) can be monitored by profilometry and edge-on photography. At the same time, the RF impedance spectrum can be measured and $f_{res}$ can be determined. After a static correlation between $f_{res}$ and the established stimulus, kinetics of swelling and deswelling can be measured given repeated step changes in stimulus in both directions (increase and decrease in T or pH). With these experiments, effects of ferrogel structure and geometry (thickness and surface patterning) on response time can be determined. For comparison, free swelling measurements can be carried out with bulk, unanchored ferrogels. Completed devices, including the membrane, can then be assembled and the dynamic responses to changes in the external environment measured.

Following the steps that generated the base, the inductance, L, of the device coil and capacitance, C, of the base can be determined using a frequency analyzer and an external coil 111 (as depicted in FIG. 1B). Inductance and capacitance can be extracted from the high and low frequency parts of the impedance spectrum. In addition, internal resistance (R) can be determined from the quality factor, Q, of the resonance, defined as the ratio between resonant frequency of the device coil, $f_{res,coil}$, and the bandwidth of the resonance peak.

Figure 4A:
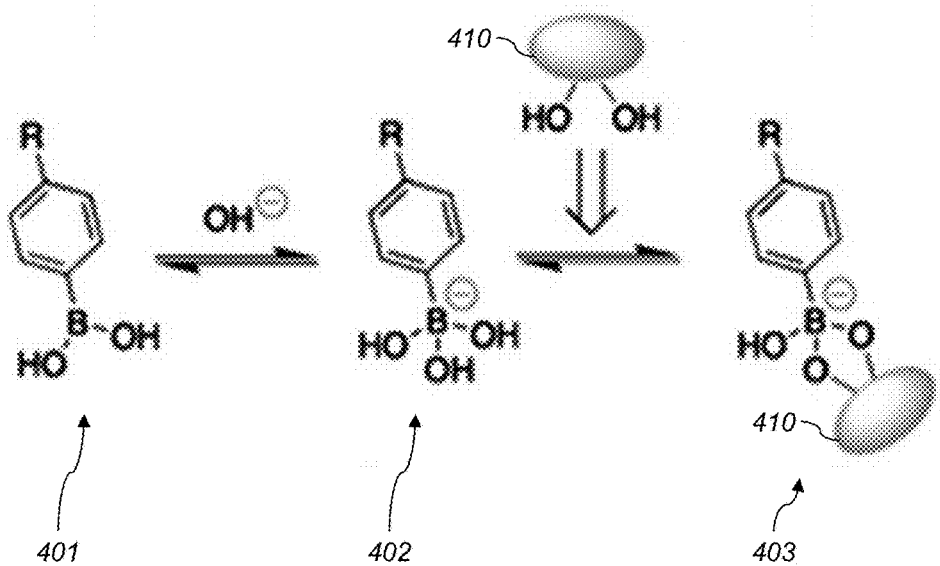
FIG. 4A depicts a mechanism by which a chemical environment forms a stable charged complex with phenylboronic acids (PBA).

Glucose concentration-sensitive sensors can be produced using glucose concentration-sensitive phenylboronic acid (PBA)-based ferrogels. With respect to glucose sensing, some PBA-hydrogel systems advantageously do not use glucose oxidase. Other glucose-sensing hydrogel systems can use glucose oxidase. Different PBA derivatives can be generated and used in order to increase specificity of response to glucose. Copolymer hydrogels containing acrylamide (AAm) and methacrylamidophenylboronic acid (MPBA), at mole ratio 20/80 MBPA/AAm can be used. One role of AAm is to provide sufficient hydrophilicity to ensure swelling, while MPBA is the glucose sensitive moiety. MBPA, a Lewis acid, is ionized by complexation with $OH^-$, and the ionic form is stabilized in the presence of cis-diol containing molecules such as glucose (see FIG. 4A, mechanism by which glucose forms a stable charged complex with phenylboronic acids (PBA); here "R" refers to the copolymer chain to which PBA is attached). In its neutral, uncharged form 401, the hydroxyls around the boron atom are in a trigonal configuration, with very low binding affinity to sugars such as glucose. Upon binding an $OH^-$ ion ($pK_0=8.86$), PBA is converted to a charged form 402, with the OH groups in a tetragonal configuration. In this configuration, the boronate ion can form a bidentate condensation complex with the sugar molecule 410 through the latter's cis-diol. Complex formation is reversible. At pH 7.4 PBA is mostly uncharged, at low sugar concentrations. With increasing sugar concentration, however, the reaction is shifted to the right, and complexation stabilizes the charged configuration in charged form 403. This mechanism implies a sugar concentration-dependent change in acid-base properties, with apparent $pK_a=pK_0-\log_{10}(1+c_{sug}/K_{sug})$, where $c_{sug}$ is sugar concentration and $K_{sug}$ is the dissociation constant of the sugar with the charged boronate. Thus PBA is mostly uncharged at physiologic pH, but becomes more ionized with increasing sugar concentration.

Another consideration is the effect of pH on sensing (mechanism depicted in FIG. 4A), since diabetic individuals are prone to swings in blood pH, especially acidosis. The relative effects of pH or chemical concentration can be estimated in terms of the change in concentration needed to offset a change in pH, keeping the fraction ionized PBA, f, constant. A modified Henderson-Hasselbalch equation, $pH=pK_0-\log_{10}(1+c_{sug}/K_{sug})+\log_{10} f/(1-f)$, applies here: Setting $df=dpH+d\log_{10}(1+c_{sug}/K_{sug})=0$ it can be shown that $dc_g=-2.303(K_{sug}+c_{sug})dpH$. A shift of $-0.1$ pH units therefore offsets a $\sim 3.2$ mM increase in glucose concentration in the normoglycemic range. Accordingly, an independent means for tracking pH is needed with this sensing mechanism, which can be provided by a dual pH/glucose sensor, as described herein.

When the PBA moiety is incorporated into a polymer hydrogel, ionization leads to osmotic swelling forces. Under free swelling conditions, these forces can lead to substantial changes in hydrogel volume, which proceed until ionic swelling pressure is equalized by retractive pressures due to polymer elasticity and hydrophobic interactions between the hydrogel and the solvent. The balance of swelling forces is normally accounted for by Flory-Rehner-Donnan-Langmuir (FRDL) theory, which under free swelling conditions predicts $$\ln(1-\varphi)+\varphi+\chi\varphi^2+\rho_0\bar{v}_w[(\varphi/\varphi_0)^{1/3}-(\varphi/2\varphi_0)]-\bar{v}_w c_s(\lambda+1/\lambda-2)=0$$

where $\varphi$ is the volume fraction of polymer at equilibrium, $\varphi_0$ is the volume fraction of polymer at synthesis, $\rho_0$ is proportional to the crosslink density at synthesis, $\bar{v}_w$ is the partial molar volume of water (0.018 L/mol), $c_s$ is the salt concentration in the external solution (typically 0.155 mM), and $\chi$ is the Flory interaction parameter. The swelling ratio relative to synthesis is given by $Q=\varphi_0/\varphi$. The term $\lambda$ is the Donnan ratio, determined by properly assuming electroneutrality in the hydrogel:

$$(1-\varphi)c_s(\lambda-1/\lambda)-f\sigma_0(\varphi/\varphi_0)=0$$

where $\sigma$ is the density (mol/volume of hydrogel) of ionizable PBA units at synthesis, and f is the fraction of these units that are ionized at a given pH and fructose concentration. Taking into account that pH inside the hydrogel differs from that in the external solution, the Donnan ratio is used in the expression for f according to $$f = \frac{1}{1+\lambda 10^{-(pH-pK_0)}/(1+c_{sug}/K_{sug})}$$

Combining the above equations enables prediction of swelling pressure under confinement, or degree of free swelling when the hydrogel is unconfined and $\Delta P=0$.

Free swelling experiments have been undertaken to ascertain the validity of the FRDL theory and to obtain parameter estimates. To this end, hydrogels were synthesized from a pregel solution containing 20 mol % MPBA and 80 mol % AAm, crosslinked with 10 mg N, N-methylene-bisacylamide (BIS), all dissolved in 1 mL of 1N NaOH along with ammonium persulfate (initiator) and N,N,N,N-tetramethylethylenediamine (TEMED, accelerator). Copolymerization with AAm was undertaken since MPBA is intrinsically hydrophobic.

Figure 4B:
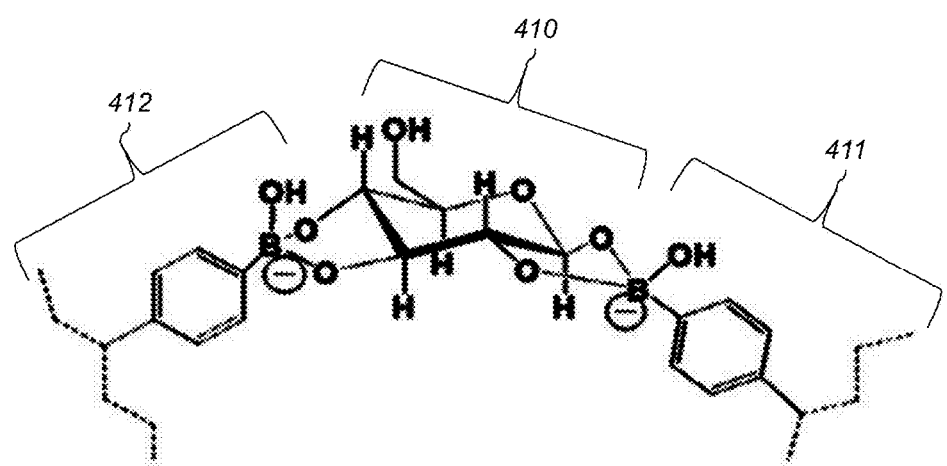
FIG. 4B is a diagram of when PBA moieties are highly charged, where a single glucose molecule can complex with two PBAs, forming transient crosslinks between host polymer chains.

Fructose responsive swelling was first studied since it is simpler than glucose responsive swelling. FIG. 4D displays free swelling equilibria in buffered saline solutions ($c_s=0.155$ mM) over an extensive pH range and for fructose concentrations 0, 0.5, 2, 7, and 20 mM. The abscissa is pH and the ordinate is gel thickness in mm. Swelling increases sigmoidally with pH, and exhibits shifts in the acid direction with increasing fructose concentration. Curves are fits of FRDL theory (free swelling: $\Delta P=0$), based on $\chi=(1-f)\chi_u+f\chi_c$, where "u" and "c" refer to the uncharged and uncharged forms of MPBA, respectively. A potential rationale for ionization-dependent $\chi$ lies in the change in polarity and hence hydrophilicity of the PBA moiety when it is charged.23 The parameters $\rho_0$ and $\sigma_0$ were fixed at synthesis, and least squares fitting yielded the parameter estimates $\chi_u=0.61$, $\chi_c=0.35$, $\rho_0=0.028$, and $K_f=0.10$ mM. The difference between $\chi_u$ and $\chi_c$ is large; these values bracket $\chi=0.5$, the critical value demarcating the transition between hydrophilicity and hydrophobicity.

In contrast to fructose, glucose contains two cis-diols, and when the hydrogel is sufficiently ionized at high pH, glucose forms transient bridges, or crosslinks between MPBA's on separate polymer chains (see FIG. 4B, when PBA moieties are highly charged, a single glucose molecule 410 can complex with two PBAs 411, 412, forming transient crosslinks between host polymer chains), causing the hydrogel to shrink. These two opposing effects are manifested in the joint pH-glucose swelling characteristic illustrated in FIG. 4C (graph of hydrogel diameter (ordinate, mm) versus pH (abscissa) depicting joint effect of pH and glucose concentration $C_G$ on hydrogel swelling, reflecting these effects). Below about pH 8.6, increased glucose concentration leads to increased swelling, while above about pH 8.6, increased glucose concentration causes the hydrogel to shrink.

Figure 4C:
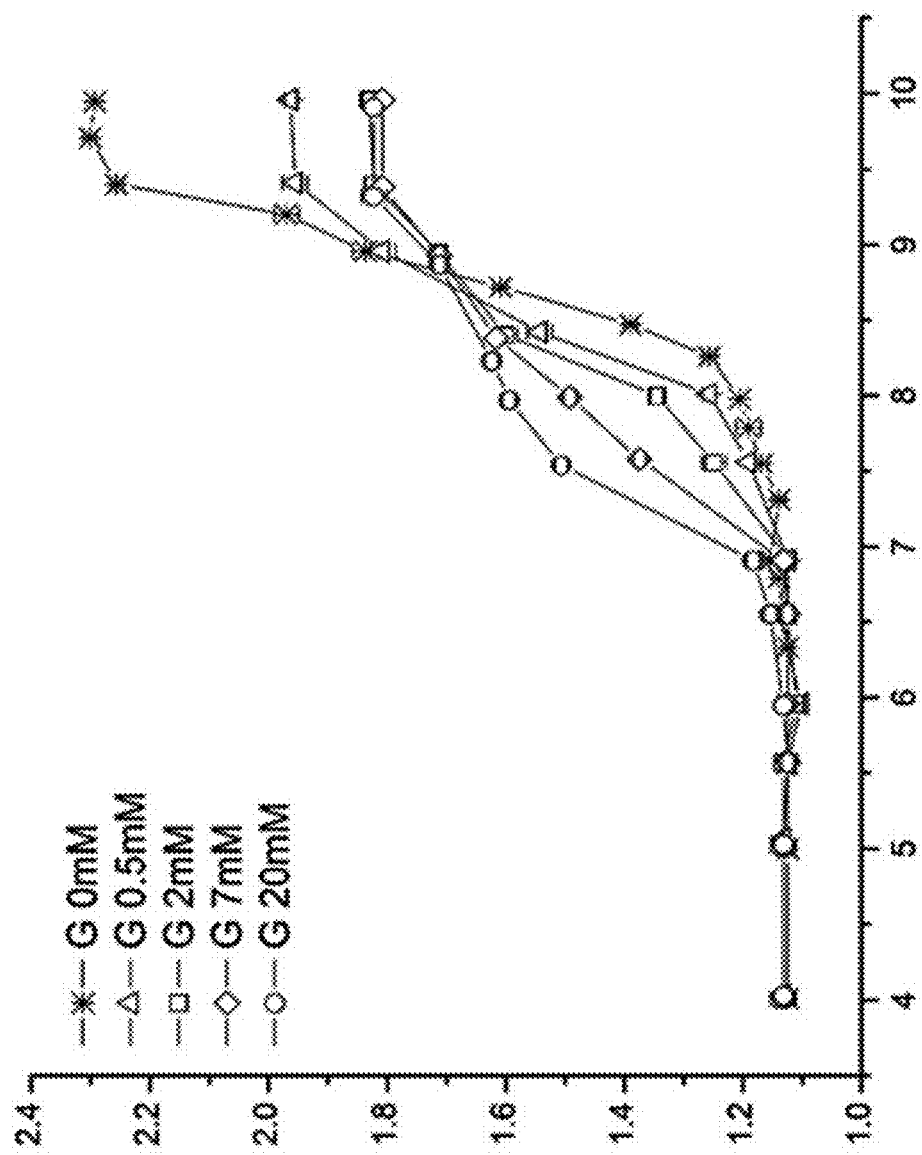
FIG. 4C is a diagram of effect of pH and glucose concentration on ferrogel swelling expressed as ferrogel diameter in mm versus pH.
Figure 4D:
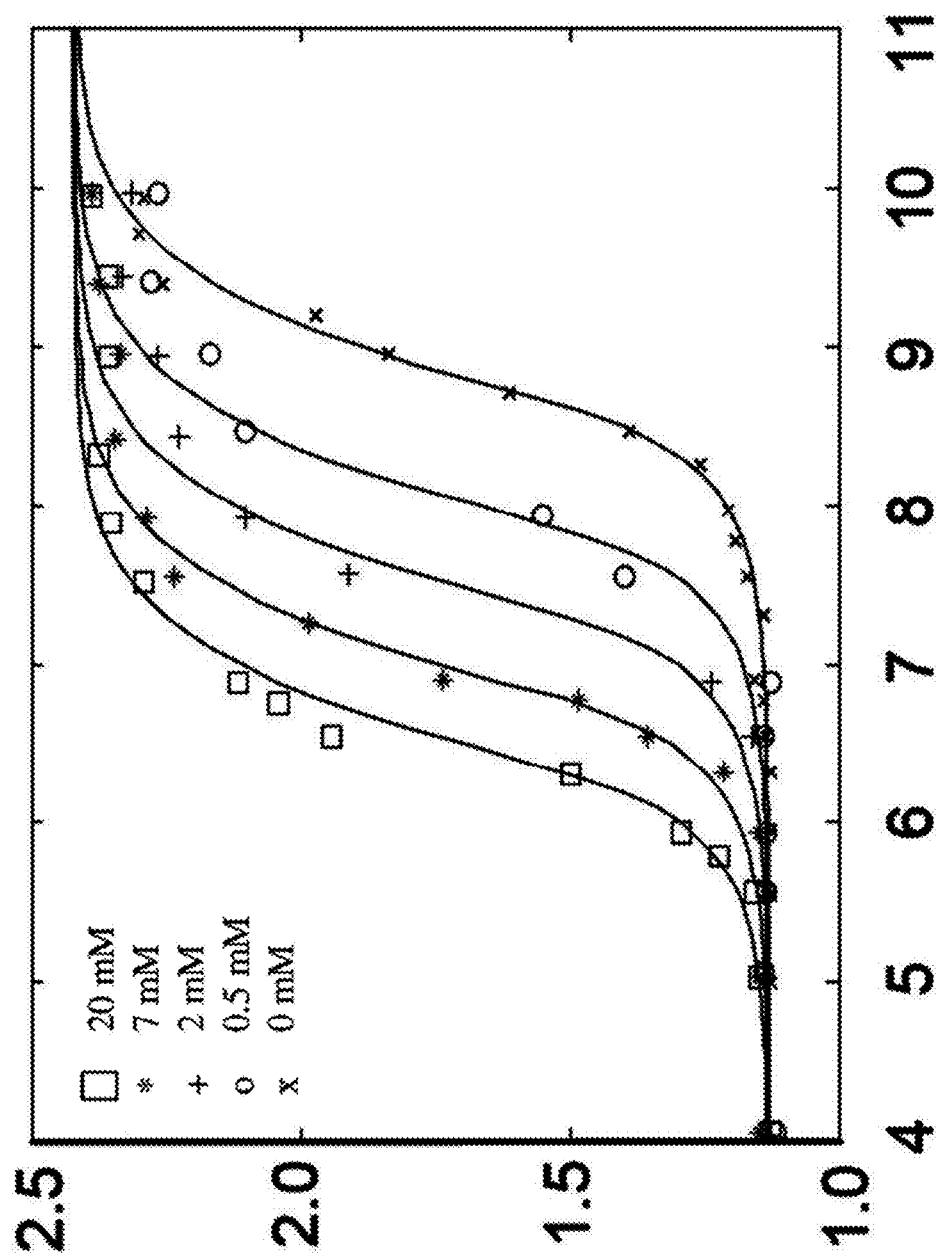
FIG. 4D is a graph of swelling diameter as a function of pH for various fructose concentrations.
Figure 5:
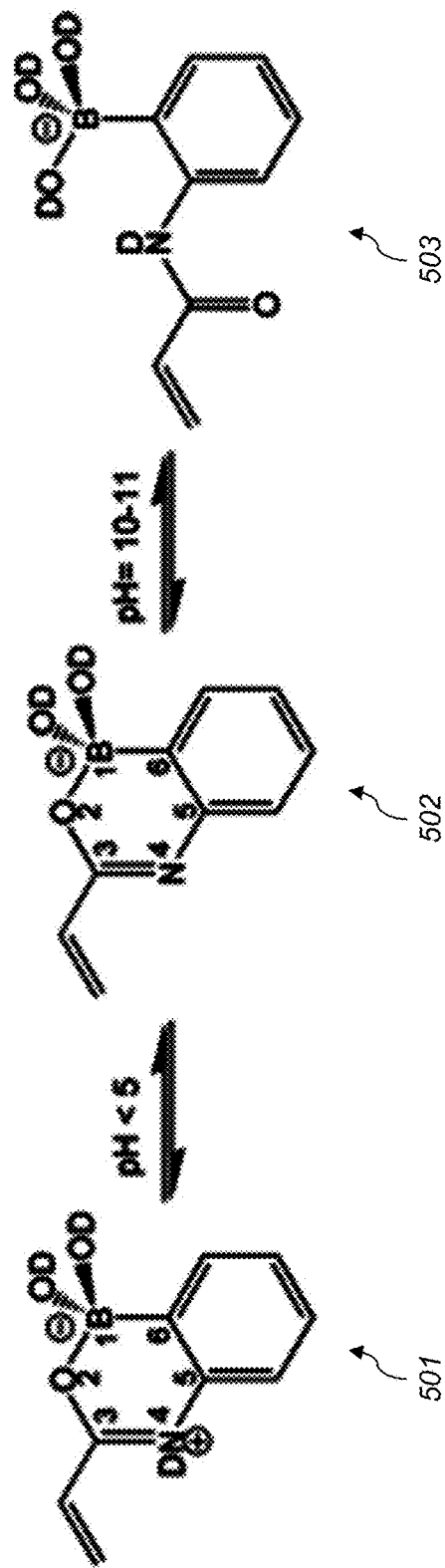
FIG. 5 is a diagram of structure and acid-base properties of the monomer 2-acrylamidophenylboronate (2-APB).

It is apparent from FIG. 4C that swelling is sensitive to pH near pH 7.4, which is a disadvantage, particularly given the tendency towards acidosis and alkalosis in diabetes. It has been demonstrated that shrinking near pH 7.4 is partially, but not completely eliminated by co-incorporating dimethylaminopropyl-methacrylamide (DMP), at equimolar amounts with MPBA, in the hydrogel. DMP is a Lewis base which replaces $OH^-$ in the reaction scheme of FIG. 4A.

pH-sensitivity can be effectively eliminated by repositioning the boronate on the phenyl ring, converting MPBA to another glucose sensitive monomer, 2-acrylamidophenylboronate (2-APB). The structure of this monomer and its acid-base reactions are shown in FIG. 5. For pH 5-9, the dominant form 502 contains an intramolecular Lewis acid-base complex, with essentially pH-independent shrinking as a function of glucose concentration, along with effective specificity against potentially interfering species, e.g., lactate. Below pH 5, the nitrogen atom in 2-APB is ionized by binding of a free proton (shown as a deuteron, D, in form 501) while at pH>10 the boron atom, B, in 2-APB is complexed with hydryoxide ion (shown as OD in form 503), and the intramolecular ring containing boron is broken. The forms and reactions described in this paragraph are commonly known in the art.

To synthesize chemically sensitive PBA-based hydrogels, first ferrogels can be synthesized and their chemical concentration dependent swelling properties measured. The concentration dependent swelling properties can be based on changes in glucose, pH, and other chemical environments as discussed herein. Next, 2-APB/AAm hydrogels can be synthesized and characterized, measuring the concentration-dependent swelling equilibria and kinetics, first without and then with the ferromagnetic nanoparticles. Swelling or shrinking kinetics can be measured at 20° C. (room temperature) and 37° C., since the latter is body temperature, and since others have demonstrated a strong accelerating temperature effect on binding/dissociation kinetics of PBA with glucose.

Next, devices containing hydrogels sensitive to glucose or other chemicals can be assembled and tested, combining methods already outlined above. Device response kinetics can be tested with step changes in glucose concentration at relevant levels at over the pH range 7.1-7.5, relevant to acidosis and alkalosis, and can also check sensitivity to glucose over interfering species such as fructose and lactate.

In a situation where the function of pancreatic β-cells is to be provided, as well as many other situations, blood glucose level may need to be sensed on a continuous basis so that insulin can then be delivered when the patient is hyperglycemic. In addition, low basal insulin can be delivered during normoglycemic periods. In various examples of insulin pumps and glucose monitors, when the device senses a glucose level nearing hypoglycemia, it can either signal a temporary halt to insulin delivery, or suggest the patient restore normoglycemia by ingesting carbohydrates. An example of a continuous glucose monitoring system with insulin pump is the MEDTRONIC MINIMED PARADIGM REAL-TIME REVEL System. However, this system requires a sensor that extends on both sides of the skin for monitoring. Various aspects described herein provide improved blood glucose sensors that can provide accurate measurements and do not require leaving a needle through the skin for extended periods of time.

Figure 6A:
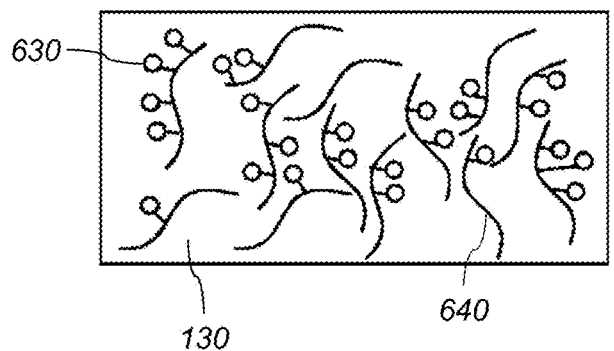
FIGS. 6A, 6B, and 6C are diagrams of various hydrogel structures, each having a different type of ferromagnetic particle structure embedded therein.
Figure 6B:
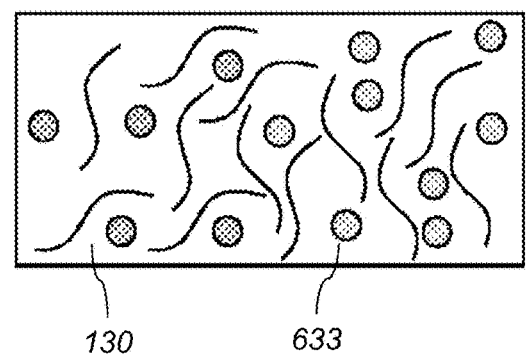
Figure 6C:
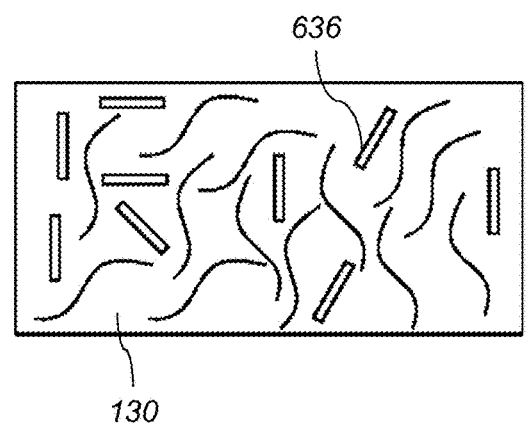

Referring to FIGS. 6A through 6C, various embodiments for embedding ferromagnetic particles and structures in the hydrogel 130, as discussed herein, are provided. For example, in FIG. 6A, ferromagnetic nanoparticles 630 are bonded to polymer chains 640 that form the hydrogel. As discussed above, the polymer chains 640 can be crosslinked to form a mesh or other crosslinked configuration. In FIG. 6B, micron-sized structures 633 filled with ferromagnetic nanoparticles can be dispersed within the hydrogel 130. In FIG. 6C, ferromagnetic particles 636 in the form of plates, bars, or flakes can be distributed throughout the hydrogel 130. It should be appreciated that ferromagnetic particles discussed herein can be magnetic, ferromagnetic, paramagnetic, or superparamagnetic.

Figure 7:
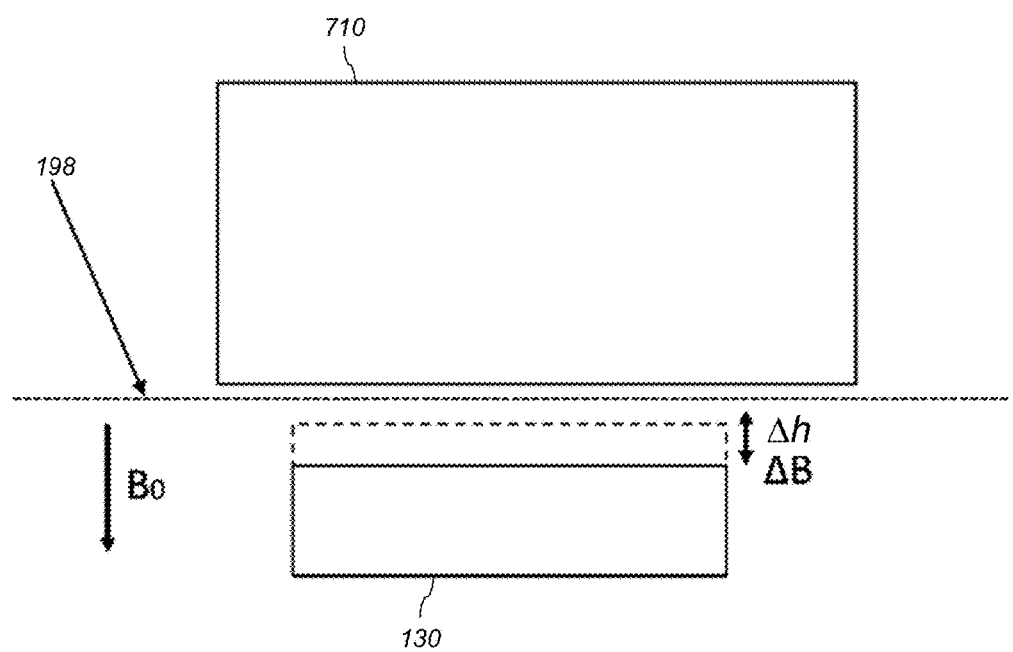
FIG. 7 is an embodiment of a sensing system using a Hall-effect type sensor.

Referring to FIG. 7, an alternative embodiment is depicted, as described above, where a Hall-effect type sensor 710 is used in association with an implantable device having magnetic nanoparticles. In this embodiment, a sensitive magnetic sensor can be used to establish a bias field $B_0$. Changes in the height of the hydrogel layer can result in changes in the magnetic field identified as $\Delta B$. Total field (B) is then $B_0+\Delta B$. By sensing the overall field (B), changes in the field (i.e., $\Delta B$) can be measured. The magnitude of $\Delta B$ can then be correlated to changes in the height of the hydrogel which can then be correlated to the concentration of chemicals for which the hydrogel is provided. As shown in FIG. 7, the magnetic-field sensor 710 can be spaced apart from the hydrogel 130, e.g., outside the skin when the hydrogel is implanted in the body. The magnetic field sensor is also referred to as a "magnetic-field detector" to differentiate it from the implantable device, which is sometimes referred to herein as a "sensor" since it senses the condition. In other examples, a SQUID can be used as the magnetic-field detector. SQUID detectors measure electrical properties resulting from the effects of magnetic fields on currents through Josephson junctions.

Figure 8B:
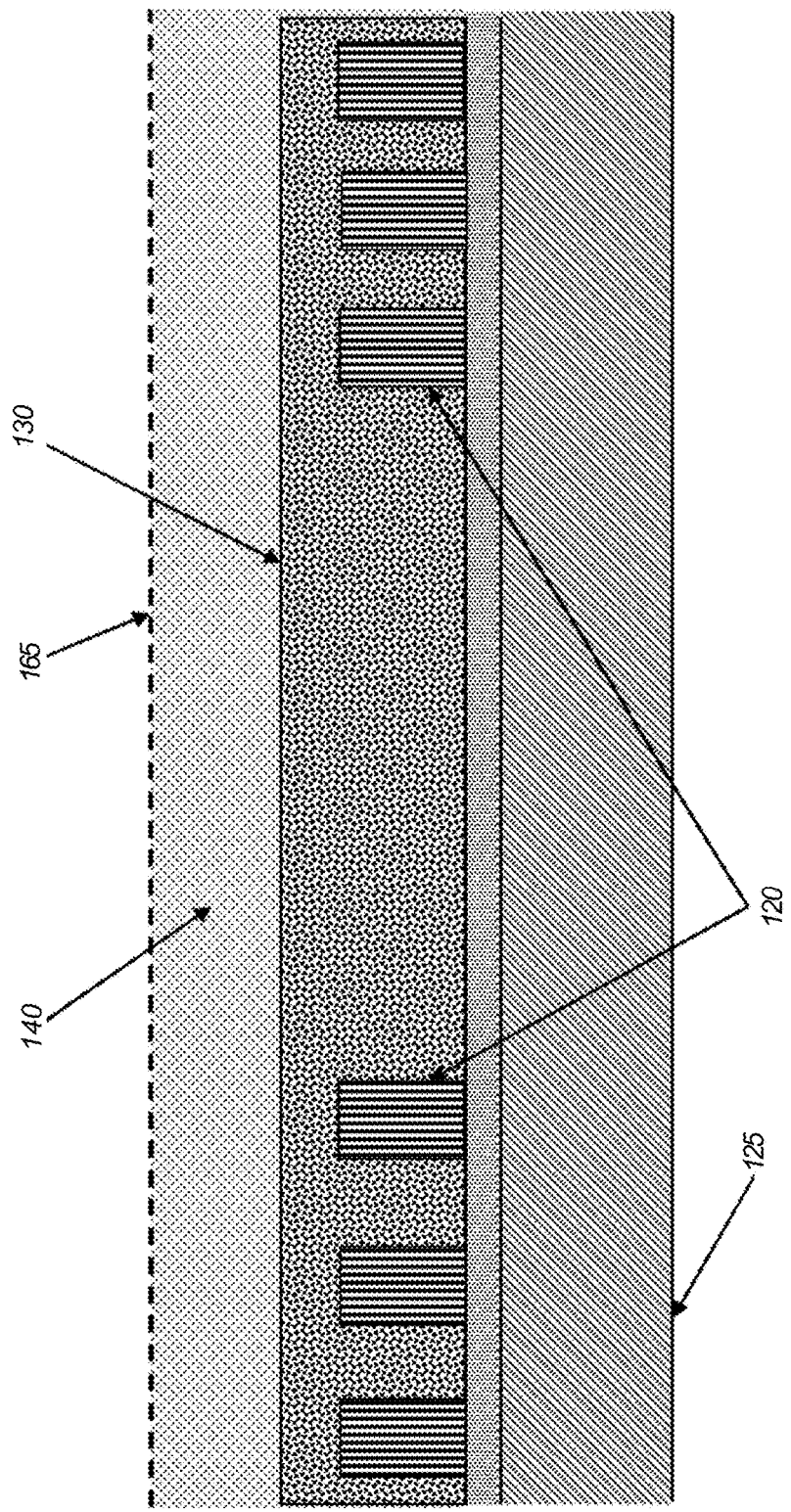

Referring to FIGS. 8A and 8B, various embodiments similar to that depicted in FIG. 1 are provided. In FIG. 8A, device coils 120 are depicted as being positioned above the substrate 125 and inside the fluid space 140 (i.e., the space defined by the membrane 165 which selectively allows passage of fluid, e.g., intercellular fluid, and prevents passage of particles of predetermined sizes, e.g., cells). Also depicted are patterns of the hydrogel 130. In this embodiment, the device coils are electrically insulated from the surrounding to prevent electrical shorting. In FIG. 8B, similar to FIG. 8A, the insulated device coils 120 are positioned above the substrate 125, however, the device coils are positioned inside the hydrogel 130.

Figure 9A:
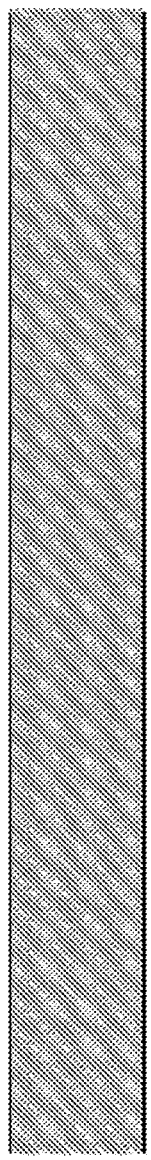
FIGS. 9A, 9B, and 9C are diagrams showing various fabrication steps according to various aspects.
Figure 9B:
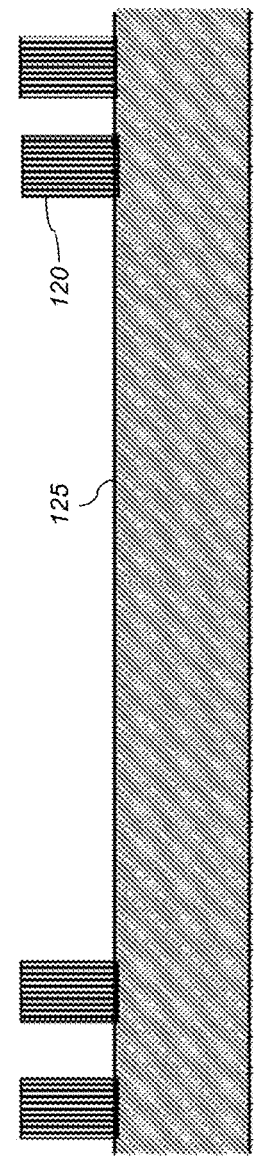
Figure 9C:
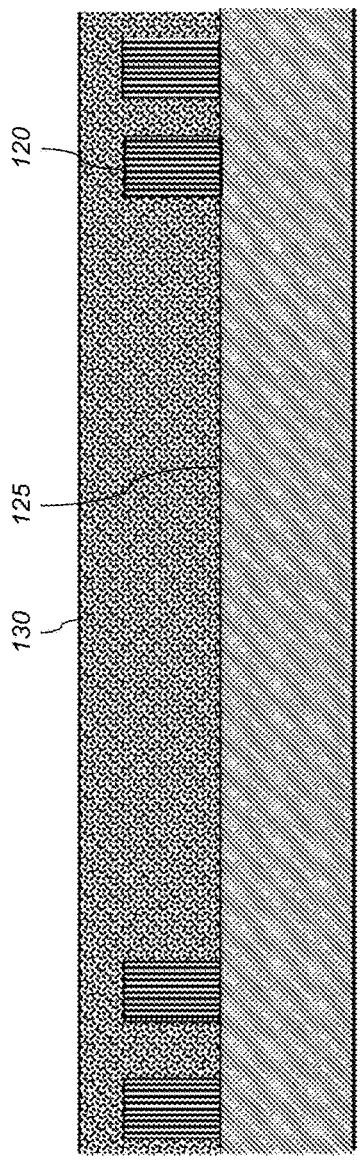

Referring to FIGS. 9A through 9C, process steps are presented for fabricating various embodiments of the microsensor according to the various aspects. FIG. 9A depicts a starting substrate, e.g., silicon, glass, plastic, insulated metal layer, or other commonly used substrates in the field of semiconductors. FIG. 9B depicts formation of device coils 120 over the substrate 125 using metal deposition, patterning, and electroplating. FIG. 9C depicts formation of the hydrogel 130 over the substrate 125 after the surfaces are treated with adhesion promoters. The hydrogel can be cast-formed.

Figure 10:
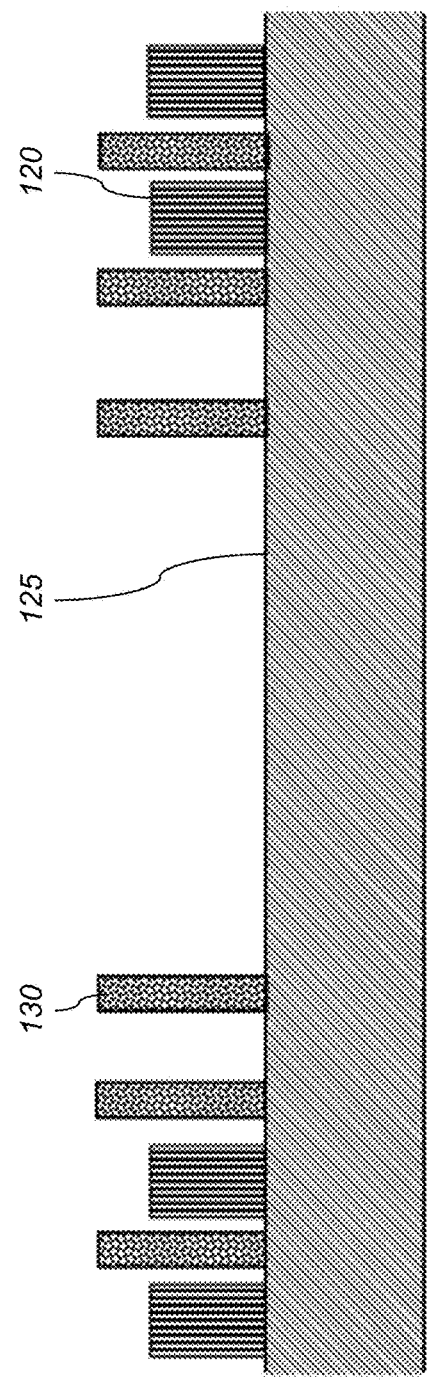
FIG. 10 shows various embodiments of hydrogel structures.

FIG. 10 depicts various patterns of the hydrogel 130 formed about the device coils 120. These patterns can be formed individually, or formed by a masking process after formation according to FIG. 9C. Other approaches (not shown) include formation of the device coils inside of the substrate followed by formation of the hydrogel over the substrate are also envisioned. The ring 155 shown in FIG. 1A can be made from the same material as the substrate and bonded thereto. Alternatively, the ring can be made as an integral part of the substrate.

Figure 11:
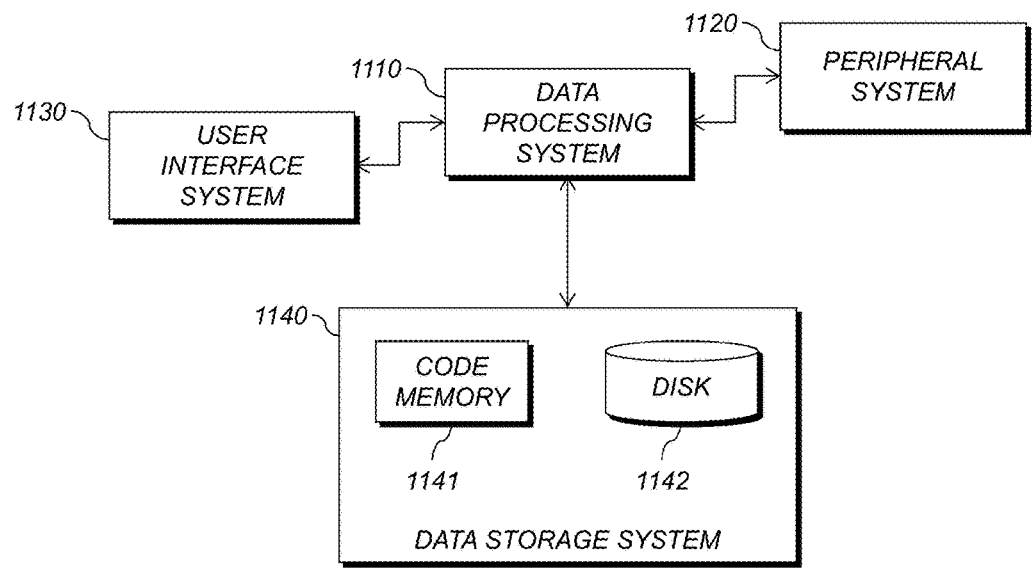
FIG. 11 is a high-level diagram showing the components of a data-processing system.

FIG. 11 is a high-level diagram showing the components of a data-processing system for analyzing data and performing other analyses described herein, e.g., detecting resonance frequencies. The system includes a data processing system 1110, a peripheral system 1120, a user interface system 1130, and a data storage system 1140. The peripheral system 1120, the user interface system 1130 and the data storage system 1140 are communicatively connected to the data processing system 1110. Data processing system 1110 can be communicatively connected to a network, e.g., the Internet or an X.25 network.

The data processing system 1110 includes one or more data processor(s) that implement processes of various aspects described herein. A "data processor" is a device for automatically operating on data and can include a central processing unit (CPU), a desktop computer, a laptop computer, a mainframe computer, a personal digital assistant, a digital camera, a cellular phone, a smartphone, or any other device for processing data, managing data, or handling data, whether implemented with electrical, magnetic, optical, biological components, or otherwise.

The phrase "communicatively connected" includes any type of connection, wired or wireless, between devices, data processors, or programs in which data can be communicated. Subsystems such as peripheral system 1120, user interface system 1130, and data storage system 1140 are shown separately from the data processing system 1110 but can be stored completely or partially within the data processing system 1110.

The data storage system 1140 includes or is communicatively connected with one or more tangible non-transitory computer-readable storage medium(s) configured to store information, including the information needed to execute processes according to various aspects. A "tangible non-transitory computer-readable storage medium" as used herein refers to any non-transitory device or article of manufacture that participates in storing instructions which may be provided to data processing system 1110 for execution. Such a non-transitory medium can be non-volatile or volatile. Examples of non-volatile media include floppy disks, flexible disks, or other portable computer diskettes, hard disks, magnetic tape or other magnetic media, Compact Discs and compact-disc read-only memory (CD-ROM), DVDs, BLU-RAY disks, HD-DVD disks, other optical storage media, Flash memories, read-only memories (ROM), and erasable programmable read-only memories (EPROM or EEPROM). Examples of volatile media include dynamic memory, such as registers and random access memories (RAM). Storage media can store data electronically, magnetically, optically, chemically, mechanically, or otherwise, and can include electronic, magnetic, optical, electromagnetic, infrared, or semiconductor components.

Aspects described herein can take the form of a computer program product embodied in one or more tangible non-transitory computer readable medium(s) having computer readable program code embodied thereon. Such medium(s) can be manufactured as is conventional for such articles, e.g., by pressing a CD-ROM. The program embodied in the medium(s) includes computer program instructions that can direct data processing system 1110 to perform a particular series of operational steps when loaded, thereby implementing functions or acts specified herein.

In an example, data storage system 1140 includes code memory 1141, e.g., a random-access memory, and disk 1142, e.g., a tangible computer-readable rotational storage device such as a hard drive. Computer program instructions are read into code memory 1141 from disk 1142, or a wireless, wired, optical fiber, or other connection. Data processing system 1110 then executes one or more sequences of the computer program instructions loaded into code memory 1141, as a result performing process steps described herein. In this way, data processing system 1110 carries out a computer implemented process. For example, blocks of the flowchart illustrations or block diagrams herein, and combinations of those, can be implemented by computer program instructions.

Computer program code can be written in any combination of one or more programming languages, e.g., Java, Smalltalk, C++, C, or an appropriate assembly language. Program code to carry out methods described herein can execute entirely on a single data processing system 1110 or on multiple communicatively-connected data processing systems 1110. For example, code can execute wholly or partly on a user's computer and wholly or partly on a remote computer, e.g., a server. The remote computer can be connected to the user's computer through a network. The user's computer or the remote computer can be non-portable computers, such as conventional desktop personal computers (PCs), or can be portable computers such as tablets, cellular telephones, smartphones, or laptops.

The peripheral system 1120 can include one or more devices configured to provide data to the data processing system 1110. For example, the peripheral system 1120 can include a reader, e.g., as shown in FIGS. 1A and 1B. The data processing system 1110, upon receipt of data from a device in the peripheral system 1120, can store such data in the data storage system 1140.

The user interface system 1130 can include a mouse, a keyboard, another computer (connected, e.g., via a network or a null-modem cable), or any device or combination of devices from which data is input to the data processing system 1110. In this regard, although the peripheral system 1120 is shown separately from the user interface system 1130, the peripheral system 1120 can be included as part of the user interface system 1130.

The user interface system 1130 also can include a display device, a processor-accessible memory, or any device or combination of devices to which data is output by the data processing system 1110. In this regard, if the user interface system 1130 includes a processor-accessible memory, such memory can be part of the data storage system 1140 even though the user interface system 1130 and the data storage system 1140 are shown separately in FIG. 11.

In view of the foregoing, various embodiments measure the magnetic properties of sensors. A technical effect is to determine, e.g., the resonant frequency of a hydrogel-device coil sensor. In an example, reader 110 (FIG. 1A) includes a data processing system 1110 and other components shown in FIG. 11, and data processing system 1110 executes stored program code to cause interrogation of the microsensor and determination of its resonant frequency or other electrical characteristics, as described herein.

Figure 13:
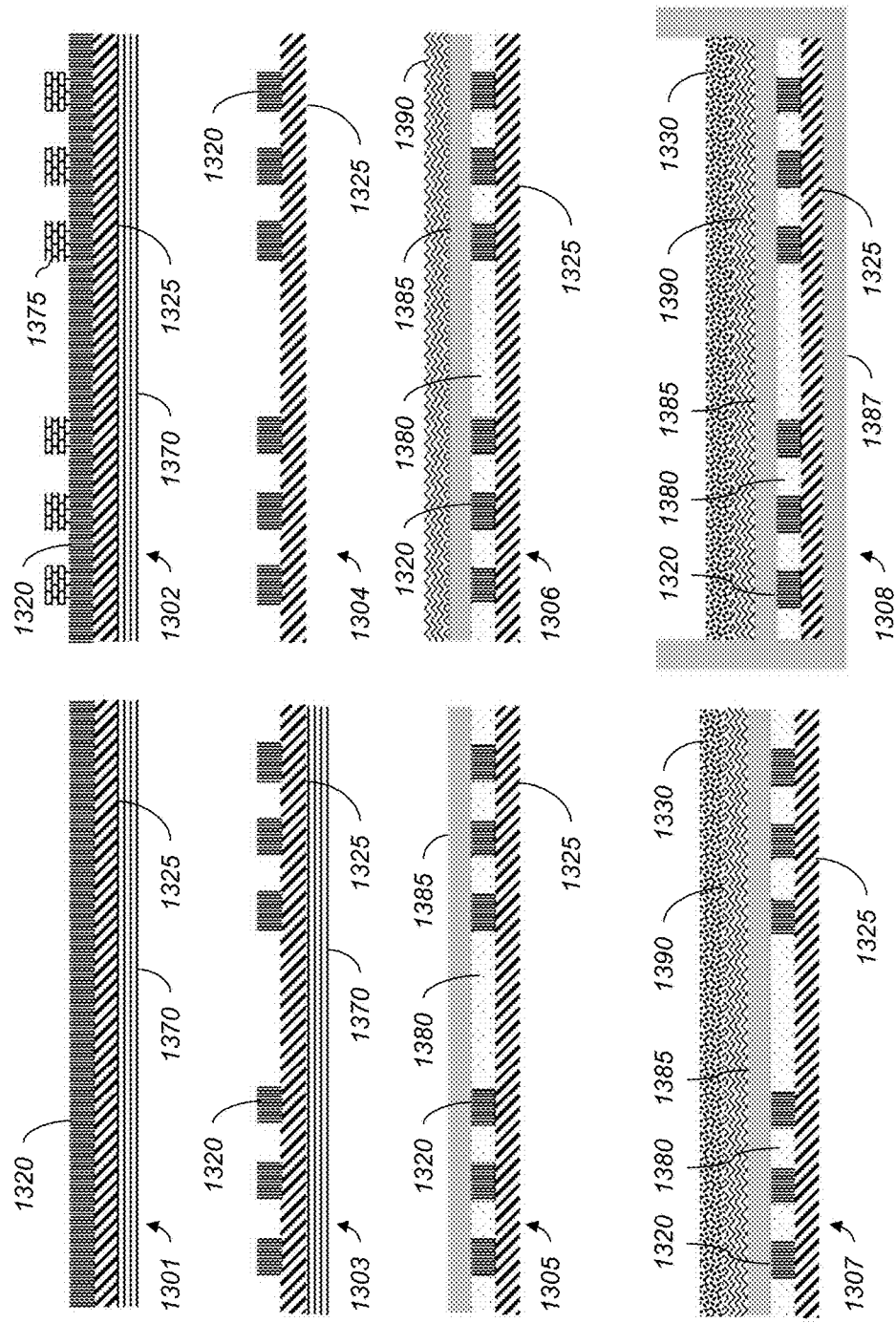
FIG. 13 shows steps in an exemplary fabrication process for ferrogel sensors.

FIG. 13 shows steps in an exemplary fabrication process for ferrogel sensors. In view 1301, copper 1320 is deposited over polyimide 1325 on a silicon backer 1370. In view 1302, photoresist 1375 is deposited on copper 1320. After etching copper 1320 and removing photoresist 1375, the result is a device coil in copper 1320, shown in view 1303. View 1304 shows the silicon backer having been removed. In an example, a planar coil (L=2.1 µH, outer diameter=10 mm, 20 turns) was patterned on a polyimide copper-clad laminate sheet. In view 1305, ultraviolet-curable epoxy 1380 is applied to the polyimide 1325 to attach transparency film 1385 to the top of the coil in the copper 1320. This provides electrical passivation. View 1306 shows gel-support layer 1390, e.g., GELBOND, applied over transparency film 1385. View 1307 shows hydrogel 1330 cast on gel-support layer 1390. In order to form the pH-sensitive poly (MAA-co-AAm) ferrogel, SPNs in PS beads of 1 µm diameter were sonicated at 3 vol % for 1 hr in an aqueous pregel solution containing MAA, AAm, methylenebisacrylamide (crosslinker) and tetraethylmethylenediamine (accelerator). The initiator, ammonium persulfate, was then added and the mixture was cast (20 µm thick) on a bonding layer (GELBOND). The result was a ferrogel pH sensor, with dimension 1.5 cm×1.5 cm×0.5 mm. View 1308 shows the sensor attached into a chamber made out of a laser machined polymeric film 1387, which can be the same polymer as film 1385.

Figure 14:
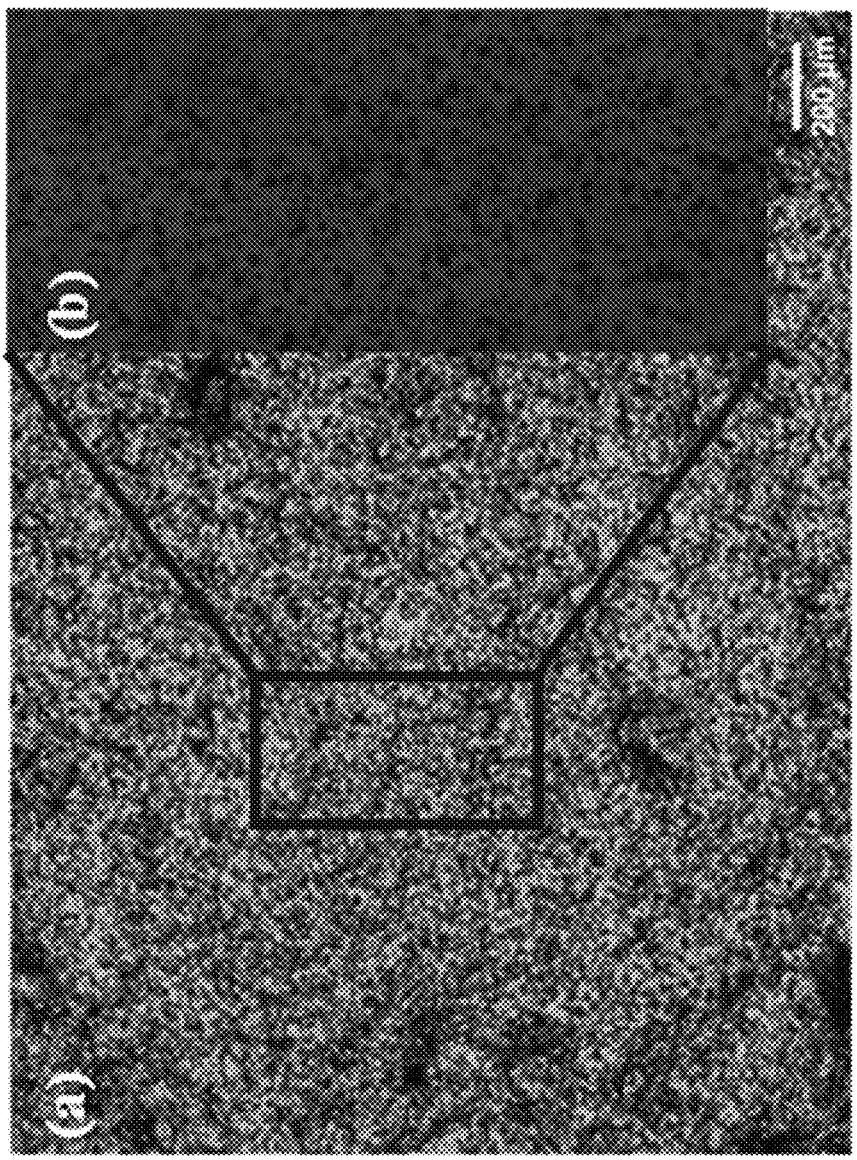
FIG. 14 is a representation of a micrograph of dispersed ferroparticles trapped inside the hydrogel network.

FIG. 14 is a representation of a micrograph of dispersed ferroparticles trapped inside the hydrogel network.

Figure 15:
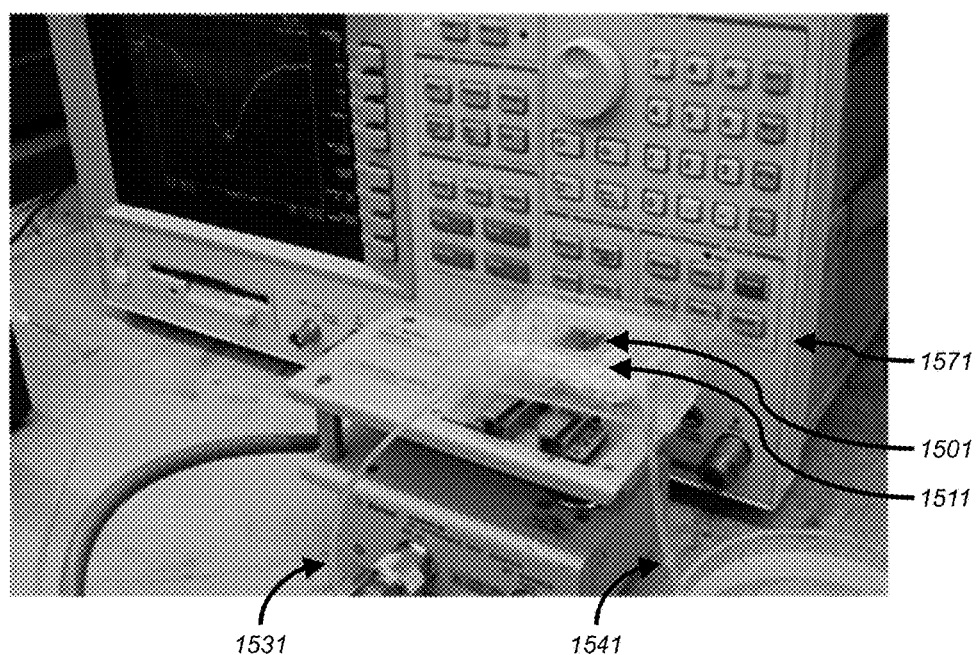
FIG. 15 is a graphical representation of a photograph of a characterization setup for measuring properties of a ferrogel sensor.

FIG. 15 shows a characterization setup for measuring properties of sensor 1501. Readout coil 1511 is placed just below ferrogel sensor 1501. Experiments were conducted in a laser-machined acrylic chamber flow system. Three pH buffer solutions (pH4, pH5, and pH6) were prepared and successively injected into the chamber by a syringe pump at a constant flow rate of 0.3 ml/min through inlet 1531 and outlet 1541. The chamber was located over a readout coil connected to an impedance analyzer 1571 for resonance frequency readout (resolution: 16.23 kHz).

FIG. 16A shows a time series of measured resonant frequency. The abscissa is time in minutes and the ordinate is $f_{res}$ in MHz. In region 1606, the pH was 6; in region 1605, the pH was 5; and in region 1604, the pH was 4.

FIG. 16B shows the measured resonance frequency of the ferrogel sensor in response to step changes in pH (MHz vs. pH). As pH increases, the ferrogel swells, resulting in a lower resonance frequency. The measured parameters of the ferrogel sensor were overall dimension 1.5 cm×1.5 cm×463 µm; response time of the sensor 40 min; sensitivity 110 kHz/pH; and resolution 0.15 pH.

In the present disclosure, there is introduced a wireless chemical sensor based on a magnetically functionalized hydrogels (ferrogels). By embedding superparamagnetic nanoparticles into the hydrogel network and laminating the hydrogel on a planar coil, the swelling state of the hydrogel, which depends on the chemical environment, can be interrogated by measuring its magnetic permeability. To validate the chemical sensing principle, a pH sensor is fabricated using a poly(methacrylic acid-co-acrylamide) pH sensitive hydrogel, and repeatable, reversible responses are obtained to pH changes, which are easily discriminated down to 0.1 pH unit. It is anticipated that the same scheme can be applied to hydrogels sensitive to different stimuli (e.g., glucose, specific ions, antigens, temperature, etc.), and that this sensor can be configured for implantation and wireless monitoring.

Environmentally sensitive hydrogels can exhibit reversible volume and shape responses to a variety of chemical and physical stimuli such as temperature, pH, specific ions, antigens, polynucleotides, glucose, etc. These responses have been utilized to fabricate a variety of chemomechanical sensors, actuators, and intelligent drug delivery platforms. Various optical, conductive, capacitive, gravimetric, magnetic and piezoresistive transduction schemes have been used to interrogate the hydrogel volumetric response.

Hydrogels are particularly attractive materials for implantable wireless sensors since they do not require an onboard power source, enabling smaller device dimensions and reduced system complexity. Various aspects herein do not require complicated fabrication processes such as those used to produce hermetically sealed MEMS capacitor pressure sensors, do not require snug-filling a small cavity with hydrogel, and provide a much shorter response time than prior schemes.

Various aspects use magnetically functionalized hydrogels, or "ferrogels," which are fabricated with superparamagnetic nanoparticles (SPNs) physically trapped inside the polymer network. Incorporation of SPNs into the hydrogel results in a material whose magnetic permeability is altered by changes in its volume and shape. When laminated and bonded on a planar inductor coil substrate, as shown in FIGS. 17A and 17B, the ferrogel modulates the inductance of the planar inductor coil, which is now sensitive to the ferrogel's thickness, which is in turn dependent on the concentration of the external analyte. Swelling and shrinking of the hydrogel are constrained only by its bond to the substrate, reducing difficulties associated with confinement. Fabrication can be carried out without resorting to exacting MEMS processing techniques.

FIG. 17A shows a configuration in which a thin ferrogel with more tightly packed nanoparticles (bull's-eye symbols) has relatively high permeability and relatively low magnetic coupled flux (curved arrows).

FIG. 17B shows a configuration in which, as a result of the presence of a stimulus or other signal of interest, the hydrogel has changed volume. The hydrogel is thicker and the nanoparticles are more widely spaced. The permeability is relatively low and the coupled magnetic flux relatively high compared to FIG. 17A.

FIG. 18 shows a ferrogel/planar inductor sensor 1820 implanted in the subcutaneous tissue 1836 under skin 1830. Skin 1830 includes epidermis 1832, dermis 1834, and subcutaneous tissue 1836. A nanoporous membrane separates the hydrogel from proteins and cells, but does not impair its swelling. Small analytes and ions in the fluid diffuse through the membrane and trigger a volume and shape response in the hydrogel, altering the inductance, L, and self-resonant frequency of the sensor, $f_r = 1/2\pi\sqrt{LC}$, where C is the (constant) capacitance due either to a capacitor that is integrated with the coil, or due to the stray capacitance of the coil. The resonant frequency is tracked wirelessly via an external readout coil. By this means, the biochemical analyte is tracked continuously. Various aspects sense physiological analytes such as glucose. Various aspects are sensitive to pH. Reader coil 1810 may be arranged to measure the resonant frequency of sensor 1820 without breaching skin 1830.

Figure 19A:
FIGS. 19A-19H show fabrication steps in a process for making sensors.
Figure 19B:
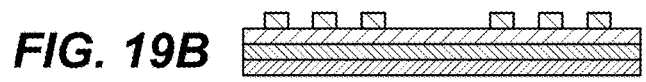
Figure 19C:
Figure 19D:
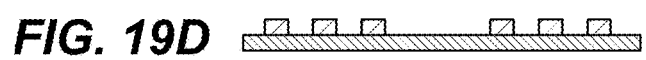
Figure 19E:
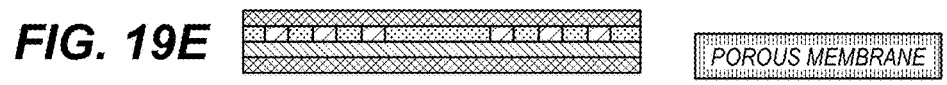
Figure 19F:

FIGS. 19A-19H depict steps in an exemplary fabrication process used for a tested device. The inductor coil was fabricated on a polyimide-laminated (PI) copper sheet (25

μm/18 gμm: Pralux AC, DuPont) (FIGS. 19A-C). After patterning the coil on the polyimide by lithography (20 turns, 100 μm width and spacing, 2.2 mm inner diameter, 10 mm outer diameter), the exposed copper was wet etched (CE-200, Transene). During the lithography process, the polyimide-laminated copper was attached to a silicon wafer, but it was released afterwards (FIG. 19D). Electrical passivation of the coil was achieved by attaching a transparency film (PP2500, 3M) to the exposed coil using UV-curable glue (Loctite 3105) (FIG. 19E). Subsequently, an adhesion promoting film (GelBond® PAG, Lonza) was attached to the transparency layer (FIG. 19F).

Figure 19G:

The pH-sensitive ferrogel was formed by adding SPN-containing polystyrene beads (ferroparticles) of 1 μm diameter (ProMag™, Bangs Laboratories) to a pregel solution including 334.5 mg of acrylamide (AAm, Sigma Aldrich), 100.8 μL methacrylic acid (mAA, Sigma Aldrich), 100 μL of N,N,N',N'-tetramethylethylenediamine (accelerator, Sigma Aldrich), 16.35 mg of N,N'-methylenebisacrylamide (cross-linker, Sigma Aldrich), and 2 μl of Tween 20 (surfactant, Bangs Lab), all dissolved 1.2 ml of DI water. The mixture was sonicated for 1 hour to achieve a dispersed suspension of ferroparticles. A solution of 80 mg·ml$_{-1}$ ammonium persulfate in DI water was added to the sonicated pre-gel solution in a 5.9 to 1 ratio and the mixture was cast onto the GelBond® film to form a thin ferrogel layer (FIG. 19G). The thickness of the hydrogel was controlled by placing a weight on the film during polymerization of the hydrogel. The beads were not chemically linked to the hydrogel but were physically immobilized since their diameter, ~1 μm, is very large compared to the mesh of the hydrogel, which is a few tens of nanometers.

Figure 19H:
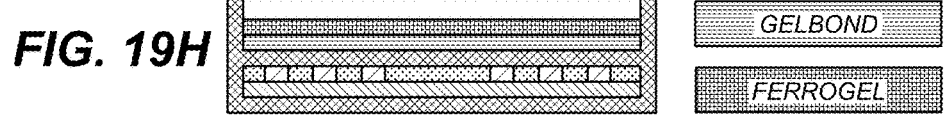

Following synthesis, the ferrogel was washed in DI water to remove unreacted monomers and sol fraction, and then dried, resulting in a ~20 μm thick film in its dry state. The dried ferrogel was either left standing or it was patterned by a laser cutter into small rectangles (375 μm×600 μm) with 150 μm spacing, or squares (130 μm)$_2$ with 200 μm spacing between the ferrogel blocks (FIG. 19H). Subsequently, the ferrogel was swelled in DI water overnight prior to testing in pH buffers. The dimensions of the fabricated sensor, including the coil substrate and ferrogel, were 12×12×0.5 mm$^3$.

Figure 20:
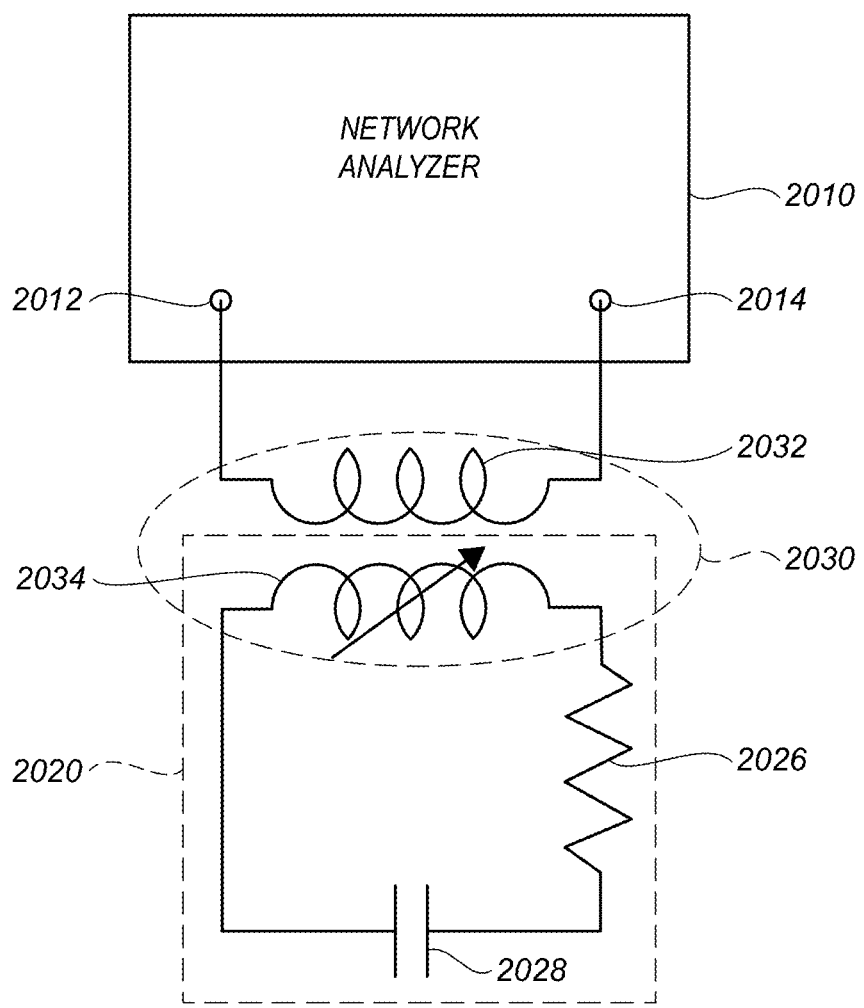
FIG. 20 shows a schematic of a system including a sensor and readout electronics.

FIG. 20 shows a test system. The sensor 2020 was placed in a laser-cut acrylic laminar flow test bed. Buffers were delivered steadily by separate syringe pumps, which were readily switched. The volume of and flow rate in the test bed were such that approximately 5-7 min was required for the pH to equilibrate following a switch in input. The sensor was mounted inside the test bed over a readout coil 2032 attached to an impedance analyzer 2010 (Agilent 4396B) at terminals 2012, 2014. Readout coil 2032 and sensor coil 2034 form a coupled pair 2030.

Figure 37:
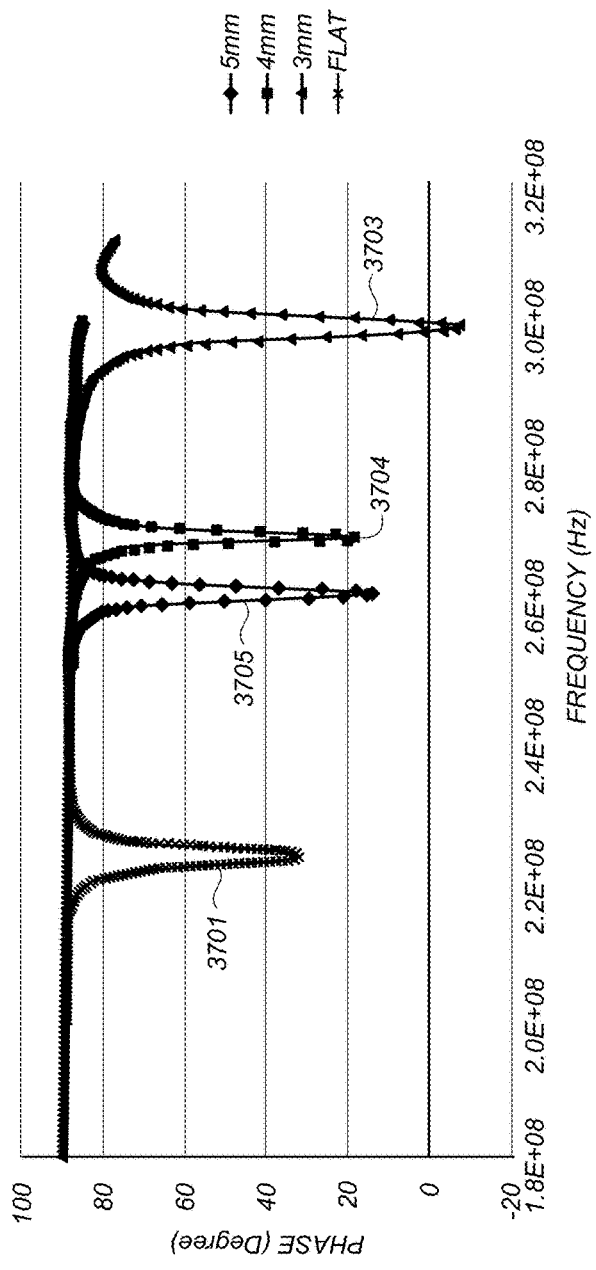
FIG. 37 shows experimental data of a tested sensor under various conditions.

As illustrated in FIG. 20, the sensor 2020 can be viewed as a passive LC tank (having inductance of sensor coil 2034, capacitance 2028, and series resistance 2026, e.g., parasitic resistance) whose inductance is a function of the volume and shape of the ferrogel. The resonant frequency of the sensor was tracked by the phase-dip method, which included monitoring the phase of the receiver coil 2032 with an impedance analyzer 2010. As the impedance analyzer 2010 swept across a frequency range, the phase of the readout coil 2032 was at its minimum at the resonant frequency of the sensor. FIG. 37 shows example phase plots.

Figure 21:
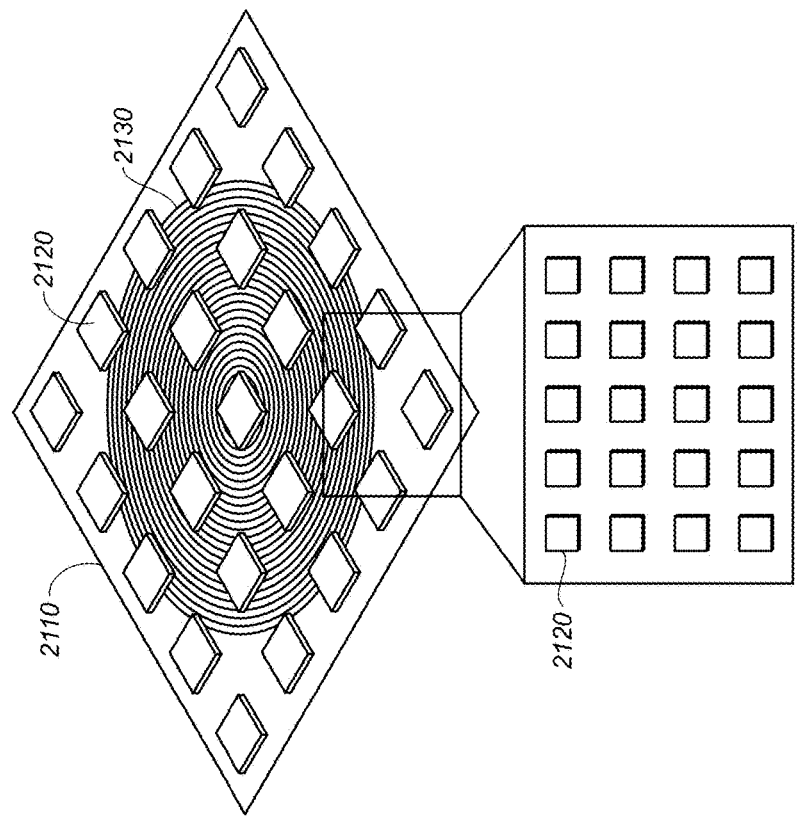
FIG. 21 shows a perspective and partial top view of a sensor according to various aspects.
Figure 23:
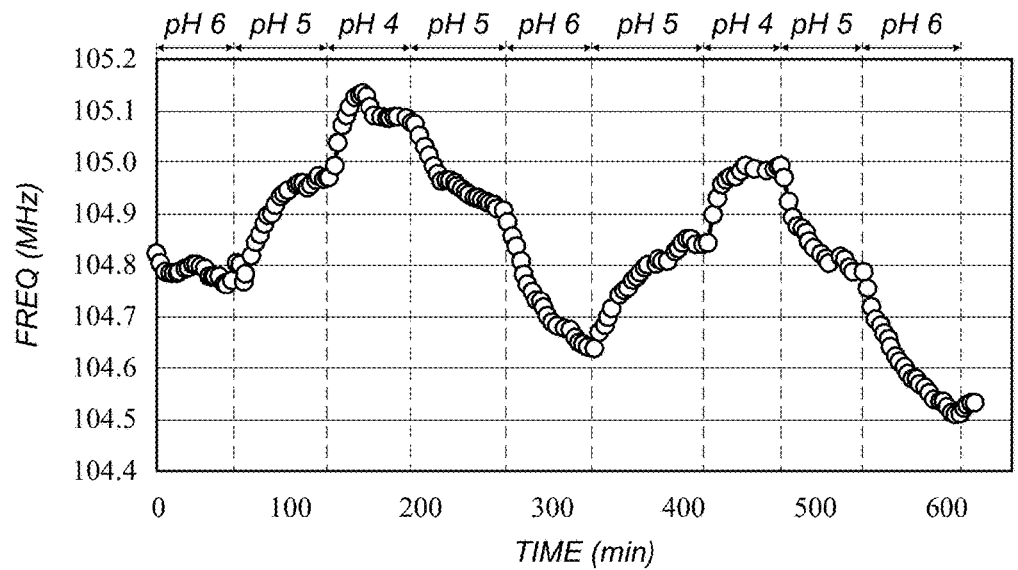
FIGS. 23-26 show experimental data of resonant frequency of a sensor as a function of pH.

FIG. 21 shows an example sensor made by patterning the ferrogel into islands 2120 (blocks) residing on the inductor coil 2130 substrate 2110. This patterning ensures consistent, reversible swelling behavior, as it substantially reduces internal stresses in the ferrogel caused by the swelling constraints imposed by bonding to the underlying GelBond® substrate. Such stresses may lead to buckling instabilities and unwanted relaxation delays.

The example sensor can include a ferrogel-coated planar coil. The device can include a thin planar inductor coil 2130 integrated into a flexible polymeric substrate 2110, e.g., parylene or polyimide. The intrinsic inductance ($L_0$) of the coil is set by its number of turns along with other geometric factors. The coil also possesses a stray capacitance, C, e.g., arising from the electrical polarizability of the dielectric material in which the coil is embedded. A laser-patterned stimulus-sensitive hydrogel containing a random dispersion of immobilized superparamagnetic nanosized ferroparticles (SPNs) ("ferrogel") is layered on top of the coil (islands 2120). This ferrogel is bonded to the embedding plastic of the coil and can swell perpendicularly to the interface. The intrinsic inductance of the coil is modified slightly by coupling of the magnetic flux lines to the SPNs. Swelling of the ferrogel in response to changes in glucose levels alters inductance due to change in SPN density. If the hydrogel is sufficiently thin, then change in its thickness can also have an effect on flux lines and hence inductance. This may be denoted by $L=L_0+\Delta L$, where $\Delta L$ is stimulus dependent. For all practical purposes, $\Delta L \ll L_0$ and therefore the fractional resonant frequency shift can be $\Delta f_{res}/f_{res,0}=-\Delta L/2L_0$, where $f_{res,0}$ is the intrinsic resonant frequency of the coil. This shift in resonant frequency can be detected wirelessly by a nearby RF transmitter/receiver (e.g., FIG. 1B) with suitably designed frequency analysis circuitry and software. A transmitter/receiver such as that shown in FIG. 1B may be connected to, e.g., a smart phone for usability.

In some examples, the SPNs (typically 10-20 nm in size) embedded into hydrogel network are prevented from leaching out of the structures. This can be accomplished by chemically bonding/linking the nanoparticles to the polymer chain. In other examples, commercially available SPN-embedded polystyrene beads (0.5-1 μm diameter) are used. Direct linking of SPNs to the polymer chains may provide greater sensitivity. Various aspects pattern of the ferrogel into smaller blocks. This has two advantages: 1) it improves the response time, and 2) it relaxes the internal stress in the hydrogel film, thus improving its stability (reducing the drift). In an experiment, it was observed that a sheet of ferrogel covering the entire coil suffered from excessive drift, which disappeared when the sheet was laser cut into small squares.

FIG. 21 is a perspective of an example sensor for detecting a condition, e.g., pH or glucose level. The sensor includes a substrate 2110, e.g., including polyimide. In an example, substrate 2110 is electrically nonconductive. A plurality of spaced-apart islands 2120 of hydrogel are arranged over substrate 2110. The hydrogel is configured to change thickness or volume in response to the condition. A plurality of magnetic particles are arranged in the hydrogel so that a magnetic property of the hydrogel changes with changes of thickness or volume of the hydrogel, e.g., as discussed above with reference to FIG. 12. In some examples, the islands of hydrogel are configured as geometrical units, e.g., tetrahedral, cubic, octahedral, dodecahedral, icosahedral, or pyramidal shapes.

An inductor coil 2130 is arranged with respect to the islands 2120 of hydrogel so that changes in the magnetic property of the hydrogel modulate an electrical property of the sensor. In the example arrangement shown, the islands 2120 of hydrogel are arranged in a layer and the inductor coil 2130 (also referred to as a "device coil") is a planar coil arranged substantially parallel to the layer. The electrical property of the sensor may be, e.g., resonant frequency, as discussed above with reference to FIG. 12. In some examples, the magnetic property is effective permeability and the electrical property is resonant frequency.

Figure 22A:
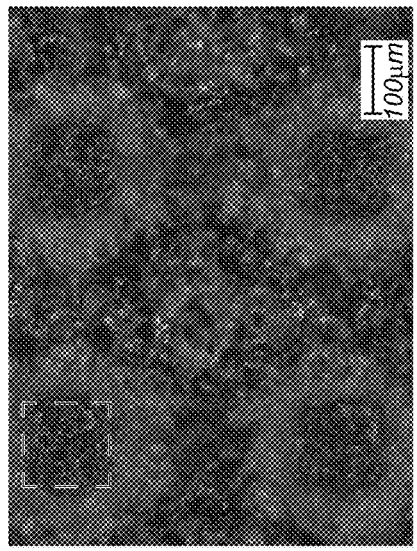
FIGS. 22A and 22B are graphical representations of micrographs showing swelling and shrinking of a hydrogel.
Figure 22B:
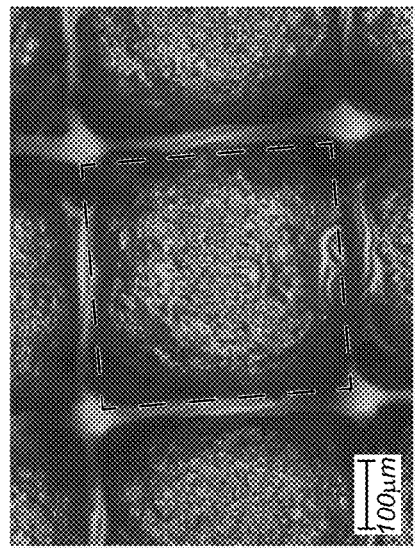

FIGS. 22A and 22B are graphical representations of micrographs of tested ferrogel blocks. The lateral expansion of the ferrogel blocks is indicated by the dashed-line boxes shown in FIGS. 22A and 22B. At high pH values, the gap between the hydrogel blocks is narrowed (compare FIGS. 22A and 22B) as a result of lateral swelling of the ferrogel, which occurs away from the bonding surface.

Figure 24:
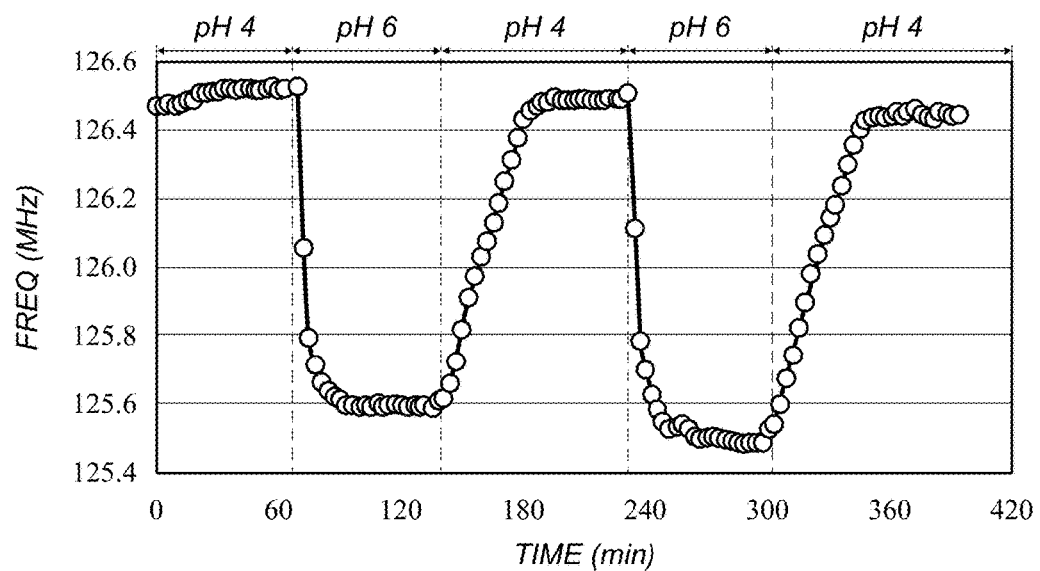
Figure 25:
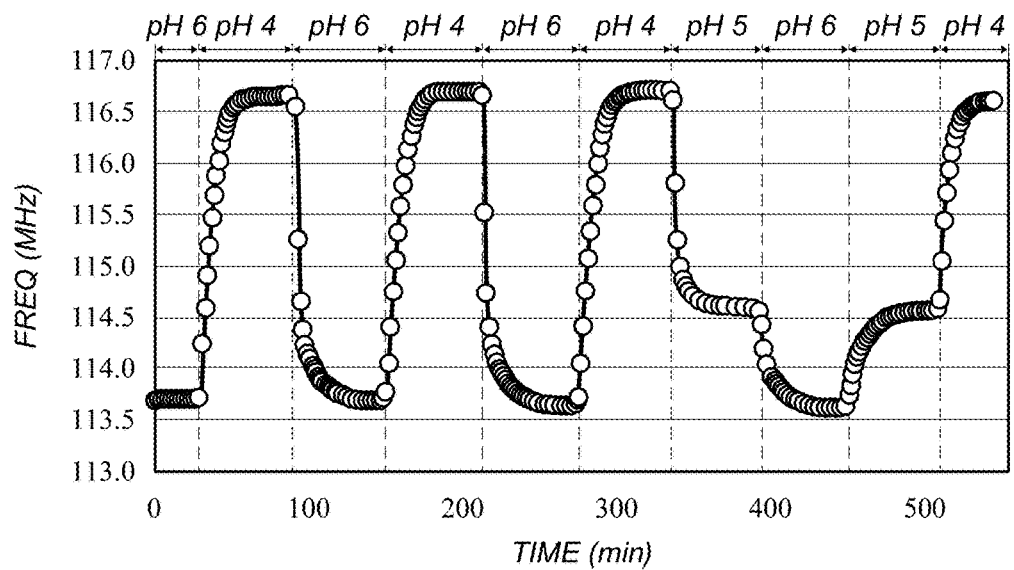
Figure 26:
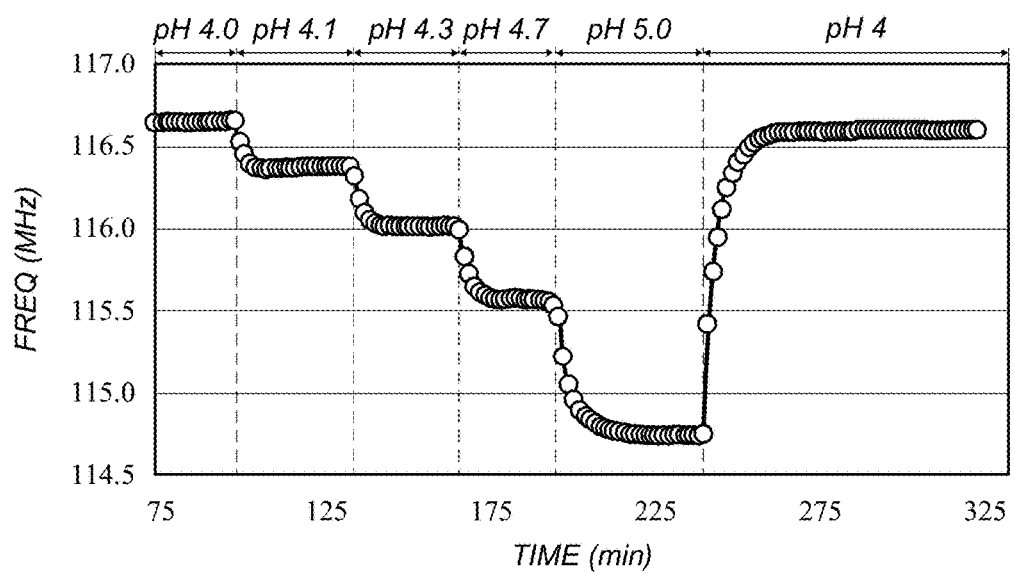

FIGS. 23-26 are measured time series of resonant frequency in response to different pH values. The results confirm the sensing principle. A decrease in frequency is observed as pH increases, as expected due to an increase in the thickness and shape change of the ferrogel, resulting from the increased ionization of the MAA groups. On the other hand, the resonant frequency increases when pH is lowered, consistent with a decrease in ferrogel thickness. FIG. 25 shows measured sensor response to up-down steps of 1 or 2 pH units, and FIG. 26 shows measured sensor response to small pH steps.

Patterning of the hydrogel into discrete blocks improved the pH-sensitivity, response time, and reversibility of the sensor (FIGS. 23-26). Without laser patterning, while the sensor displayed a response to the pH change, it also showed a downward drift (FIG. 23) due to the internal stress buildup. By patterning the ferrogel into a rectangular block of 375 μm by 600 μm with 150 μm of spacing, improved response to pH changes was observed with a significantly less downward drift (FIG. 24). When patterned into smaller squares of 130 μm wide with 200 μm of spacing between the squares, the sensor displayed a reversible pH response with no drift and was able to measure small pH changes of 0.1 unit (FIGS. 25 and 26). The responses time and the average frequencies at different pH levels are summarized in Table 1.

TABLE 1

Summary of ferrogel pH response with and without laser patterning

| Non-Patterned | | Laser Patterned (375 μm × 600 μm) | | Laser Patterned (130 μm × 130 μm) | |
| --- | --- | --- | --- | --- | --- |
| pH | Freq. [MHz] | Response Time [min] | pH | Freq. [MHz] | Response Time [min] | pH | Freq. [MHz] | Response Time [min] |
| 6 | 104.77 | — | 4 | 126.52 | — | 6 | 113.70 | — |
| 5 | 104.97 | 50 | 6 | 125.54 | 19 | 4 | 116.64 | 15 |
| 4 | 105.07 | 50 | 4 | 126.49 | 49 | 6 | 113.73 | 16 |
| 5 | 104.90 | 35 | 6 | 125.49 | 18 | 4 | 116.68 | 17 |
| 6 | 104.64 | 35 | 4 | 126.44 | 46 | 6 | 113.67 | 14 |
| 5 | 104.84 | 50 | | | | 4 | 116.69 | 17 |
| 4 | 104.99 | 50 | | | | 5 | 114.62 | 9 |
| 5 | 104.79 | 36 | | | | 6 | 113.63 | 19.5 |
| 6 | 104.53 | 35 | | | | 5 | 114.54 | 28 |
| | | | | | | 4 | 116.58 | 11 |
| | | | | | | 4 | 116.65 | — |
| | | | | | | 4.1 | 116.39 | 7.5 |
| | | | | | | 4.3 | 116.02 | 6 |
| | | | | | | 4.7 | 115.58 | 9 |
| | | | | | | 5 | 114.75 | 11 |
| | | | | | | 4 | 116.61 | 15 |

As a control (not shown), the SPN-containing polystyrene beads were replaced by blank, nonmagnetic polystyrene beads of the same diameter. This change should not affect swelling response, but such response manifests a change in the dielectric environment, since the dielectric constant of the beads is far below that of water. In this case, no significant change in resonant frequency was observed. Therefore the observed resonance changes are due to changes in the magnetic, and not the dielectric, environment.

Magnetic functionalization of hydrogel by introducing the superparamagnetic nanoparticles allows the wireless monitoring of hydrogel volume through flux linkage to an inductor. As a proof-of-concept, a pH sensitive poly(MAA-co-AAm) hydrogel was magnetically functionalized and attached to a planar inductor to form a pH sensor. The sensor showed expected responses to the pH change in its environment as its inductance was modulated by coupling between the ferrogel and the planar coil. The repeatability of the sensor was ensured by laser patterning of the ferrogel to prevent internal stress buildup during swelling. When patterned into smaller squares of 130 μm wide with 200 μm of spacing between the squares, the ferrogel sensor displayed a repeatable and reversible response to the pH change, with a sufficient sensitivity to detect 0.1 unit change in pH. Given the variety of hydrogels available for different analytes such as glucose, specific ions, pH, antigens, etc. and temperature, the same wireless principle can be applied to a broad range of sensors.

In various aspects, a wireless implantable glucose sensor can be used in the management of diabetes. Glucose sensitive hydrogels are in particular an attractive material for such application. This is due to their inherent chemomechanical transduction capability which alleviates the need to incorporate any power source and on-board electronics in the device, thus significantly reducing the implant complexity. Various aspects include an implantable wireless glucose sensor based on swelling and deswelling of a magnetically functionalized glucose sensitive hydrogel (ferrogel). The hydrogel contains a dispersion of superparamagnetic nanoparticles (SPNs) and is bonded to a flexible substrate incorporating an integrated capacitor/inductor (LC) resonator. Changes in hydrogel thickness and SPN density in response to environmental stimuli lead to a change in inductance (L) of the integrated resonator and therefore its natural resonant frequency, $f_{res} = 1/2\pi\sqrt{LC}$. Resonance will lie in the radio frequency (RF) range (100-200 MHz) permitting facile, wireless interrogation by a transmitter/receiver which might, for example, plug into a smart phone containing a suitable app. The sensors can be cylindrical in shape (2-3 mm in diameter and 1 cm² in length) and can be inserted subcutaneously under local anesthesia in an out-patient setting.

Prior schemes coupling hydrogels to solid state devices have used MEMS-based processing, involving rather difficult and expensive procedures. Example sensors disclosed here can be much simpler, inexpensive, and amenable to mass production. A prototype of this new class of sensors was constructed.

Diabetes mellitus is approaching epidemic proportions in both developing and developed countries due to increased obesity and nutritional maladjustments. According to the American Diabetes Association, 25.8 million children and adults in the United States—8.3% of the population—have diabetes (http://www.diabetes.org/diabetes-basics/diabetes-statistics/). Over a life time, hyperglycemia associated with uncontrolled diabetes can lead to degeneration of nerve, muscle, and connective tissue, with shortened life span and degraded quality of life. Blindness or loss of extremities can occur in extreme cases. Diet and exercise are important regulators of glucose metabolism in treating Type II diabetes, whereas regular insulin injection is the treatment of choice for Type I diabetes. Tight control of blood glucose level is fundamental to reducing diabetes-associated long-term morbidity and mortality.

Most commonly, Type I diabetic patients monitor their blood glucose intermittently using a finger stick, which is inconvenient and uncomfortable. Furthermore, finger sticks only provide intermittent, discrete measurements of blood glucose level, and important fluctuations may be missed. Thus, continuous glucose monitoring is critical for improved patient care. In addition to providing immediate information, data can be recorded, stored, sent over the internet, and tracked over time. Continuous sensing, in conjunction with predictive algorithms, can improve guidance of insulin delivery to not only minimize hyperglycemia but also to prevent life threatening hypoglycemic episodes. It may also be used by both Type I and Type II diabetics to assess effects of circadian rhythm, medication and behavior on glucose response to administered insulin.

Noninvasive glucose sensing, without a doubt the most preferable approach, has not been successful despite decades of intense research and development. These efforts have included: 1) Glucowatch™, a withdrawn product based on reverse iontophoresis of glucose across the skin; 2) ultrasound followed by vacuum extraction across the skin and electrochemical detection; 3) glucose sensing by absorption and reflectance of near- and far-IR radiation or more recently by surface-enhanced Raman scattering (SERS). These techniques have suffered from various shortcomings such as skin irritation (Glucowatch™ and ultrasonic approach); sophisticated, bulky, and expensive readout instrumentation; and ambiguous correlation between signal and true blood glucose level hampered by interfering analytes and scattering by intervening tissues (optical approaches).

Percutaneous (skin breaching) glucose electrodes that rely on the enzymatic (glucose oxidase) oxidation of glucose and subsequent conversion to electric current, are presently used in commercial sensors, with FDA approval limited to one week use. In developing long term, implantable, enzyme based sensors, enzyme denaturation, degradation, and poisoning should be minimized. While such sensors have demonstrated the health benefit of continuous monitoring of glucose, practical problems remain, including the need for frequent calibration against blood glucose obtained by finger stick. Infection is also a risk with each skin breach. Recently, a fully implantable glucose oxidase/catalase based sensor was shown to reliably monitor glucose fluctuations in diabetic pigs for more than one year. In this disk-shaped system (diameter 3.4 cm, thickness 1.5 cm) enzyme electrodes are packaged with a battery and microelectronics for radiotelemetry. The sensor exhibits short, clinically acceptable 6-10 min "dynamic delays", i.e. latencies in tracking up- and downswings in blood glucose concentration. Delays are attributed primarily to mass transfer in tissue.

Glucose Sensitive Hydrogels: Over the past two decades, there has been substantial interest in using hydrogels for glucose monitoring. There are several reasons why this is so. First, hydrogels are water swollen polymer networks containing chemical groups that are sensitive to the environmental stimulus such as temperature change or concentration of a chemical analyte of interest. Volume change can be regarded as a signal transduction, or in some cases, as an amplification. Second, highly hydrated hydrogels provide ready access of analyte to the sensing moiety. Third, it is possible to co-immobilize molecules or nano-objects in the hydrogel to assist in reporting the presence of the analyte. For example, a fluorescent species whose wavelength shifts in the presence of analyte can be attached to the hydrogel backbone, enabling analyte detection even without change in degree of swelling. Alternatively, a colloidal crystalline array or hologram embedded in the hydrogel, whose Bragg spacing is swelling dependent, can report swelling change by a simple color shift. Fourth, simpler physical means of reporting hydrogel swelling are available, including measurements of hydrogel mass, conductivity, and dimension. Fifth, enzymes are easily immobilized into hydrogels, which allows conversion of otherwise inert analytes to molecules that stimulate swelling and shrinking of the hydrogel and signal transduction.

Despite these potential advantages, hydrogel based sensors have not been advanced to practice for several reasons. First, as soft materials, hydrated hydrogels are difficult to manipulate and localize reliably in physically or chemically harsh environments, such as the human body or inside a chemical reactor. Second, response of hydrogels to physical or chemical stimuli tends to be diffusion controlled and hence quadratically slower with increasing size. Small dimensions are therefore required, and until recently it has been difficult to reproducibly fabricate very thin hydrogel structures. Third, readout is often nontrivial, especially if the hydrogel-containing sensor is placed under the skin.

Efforts in the area of hydrogel-based glucose sensing have included fiber optic systems with anthracene-boronate coated tips report fluorescence shifts upon glucose binding. Alternatively, swelling and shrinking of glucose sensitive phenylboronic acid (PBA)-based microgels bonded to fiber optic tips has been detected using Fabry-Perot interferometry. Such systems require either cutaneous breach by the fiber optic or co-implantation of a light source, radiofrequency (RF) transmitter, and power source, all adding bulk and packaging issues to the system. PBA-hydrogel systems do not rely on glucose oxidase, and hence circumvent issues associated with enzyme stability. Another approach relies on swelling and shrinking of colloidal crystal-embedded PBA hydrogels that can be monitored by changes in diffraction wavelength in the optical region. Glucose level can also be monitored by illuminating holographic gratings deposited in PBA-based hydrogels. Such hydrogels might sample glucose in the tear film, where concentration is correlated with, but much lower than, blood glucose level. The strength and temporal dynamics (pharmacokinetics) of this correlation are presently not well quantified, however. Incorporation of fluorescent PBA-based molecules into contact lenses for sensing of tear glucose is also under investigation. Other devices in this category uses a magnetic cantilever suspended in a microcavity containing a linear, noncrosslinked PBA-based polymer solution, whose viscosity changes with glucose concentration. Glucose concentration is sensed by optically measuring viscous damping of electromagnetically driven oscillations at relatively low (~26 Hz) frequencies. This device responds rapidly to external glucose concentration changes, but it may be difficult to configure for remote readout.

Various hydrogel-based sensors herein can sense temperature, pH, antigen, or nucleic acids. For example, the ability of nucleic acids (DNA and RNA) to form aptamers (strongly bound complexes) with a variety of analytes may be used to synthesize hydrogels that swell and shrink with varying analyte concentration. For example, attachment of crown ethers to hydrogel chains has enabled specific sensing of metal ions that preferentially bind to the crown cavities, and a variety of cyclodextrins (CDs) can be incorporated into hydrogels, whose swelling then depends on concentration of particular analytes. Template polymerization of hydrogels around selected analytes can be used, and the resulting hydrogels preferentially shrink in the presence of the target analyte. Thus, various sensors herein can sense a wide variety of biological analytes. With suitable hydrogel design, portable sensors for environmental monitoring and industrial process control can be provided.

Figure 27:
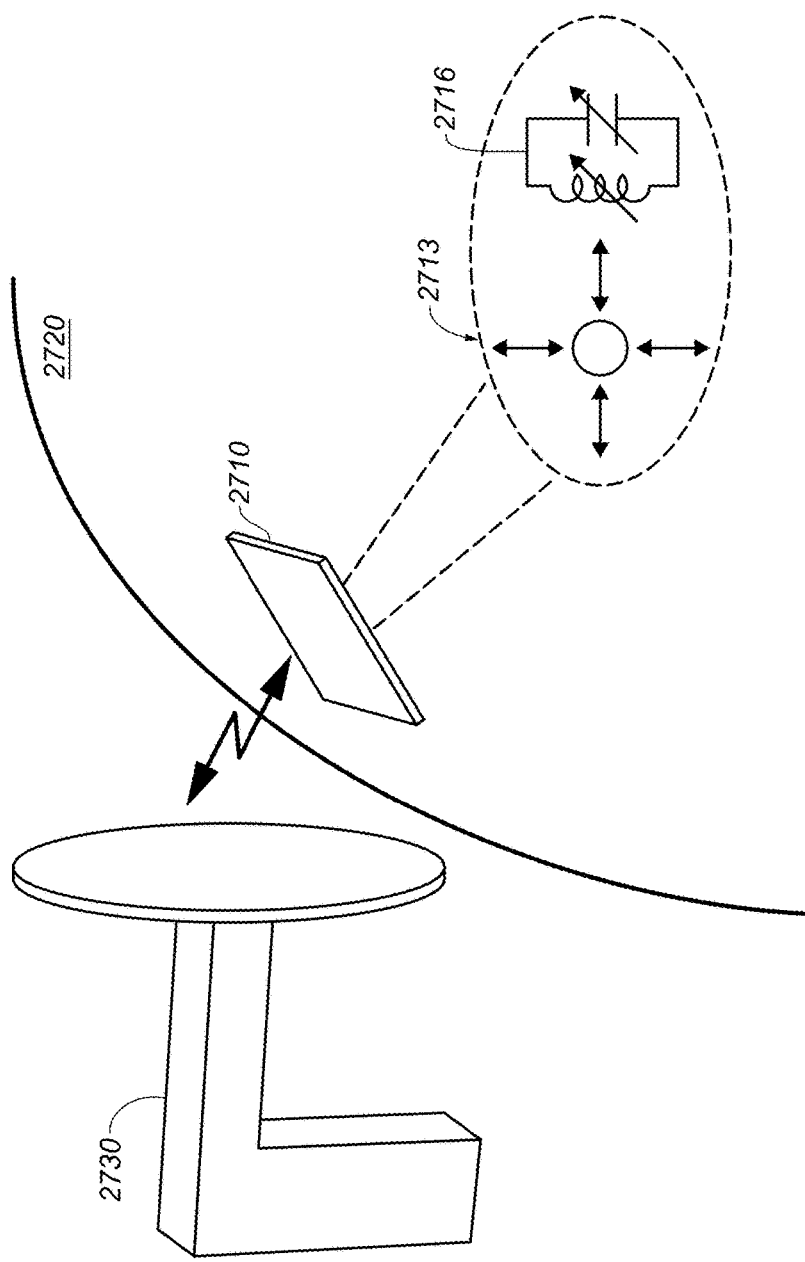
FIG. 27 depicts a system including an implantable sensor and a non-contact measuring device.

FIG. 27 shows an example measurement system including measurement device 2730 and implantable sensor 2710. Disclosed herein are implantable (e.g., under skin 2720), wirelessly interrogatable glucose sensors 2710 that use swelling changes in a glucose (analyte) sensitive hydrogel 2713 to alter the resonant frequency of an LC resonant tank 2716 in a chip or other sensor 2710 in which the hydrogel is imbedded, and wirelessly measure the resonant frequency using a nearby RF transmitter/receiver (interrogating unit) 2730.

FIG. 27 shows an example of an implantable glucose sensor that can be remotely queried. Sensor 2710 is placed under the skin 2720, and includes a hydrogel 2713 whose glucose dependent swelling alters the resonant frequency of an LC resonant tank 2716, by altering either capacitance (C) or inductance (L). Interrogating unit 2730 transmits and receives RF waves, determining resonant frequency.

Figure 28:
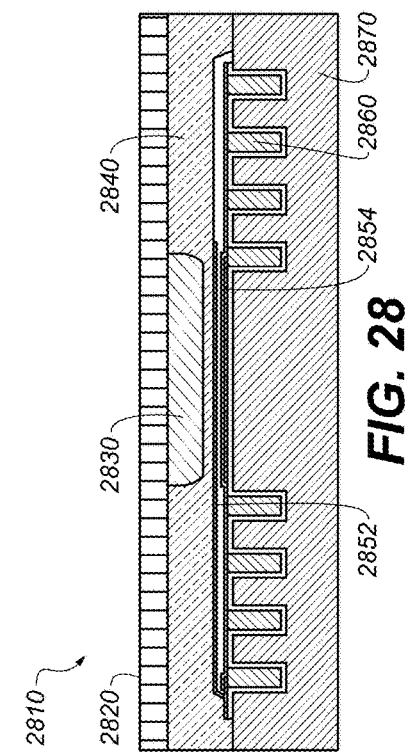
FIG. 28 shows a cross-section of an example sensor.

An example implantable wireless glucose sensor was developed and was based on the glucose dependent swelling of a phenylboronic acid (PBA) containing hydrogel. FIG. 28 is a cross sectional schematic of the microsensor 2810. A glucose-sensitive hydrogel 2830 based on phenylboronic acid (PBA) filled a chamber separating a permeable but rigid membrane 2820, and a more compliant, thin glass diaphragm 2840. The diaphragm was coated below with metal and served as the top plate 2852 of a microcapacitor, the bottom plate 2854 of which was a thin metal film coating a silicon element. A narrow, hermetically sealed gap separated the two capacitor plates. In addition, a microinductor coil 2860 was embedded in the silicon 2870 and electrically contacted to the capacitor plates, forming a LC resonator circuit. Depending on external glucose level, the hydrogel developed a swelling pressure leading to deflection of the capacitor $f_{res}=1/2\pi\sqrt{LC}$ (as above), which could be interrogated by an external transmitter-receiver.

Figure 29:
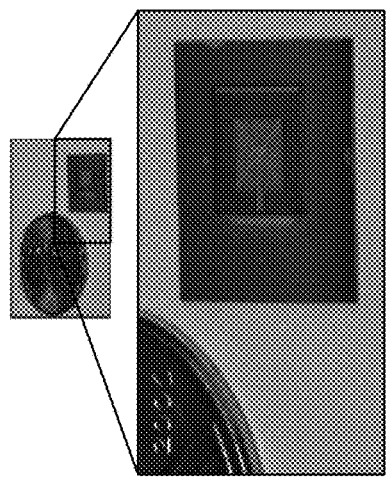
FIG. 29 shows a graphical representation of a photograph of a tested example microsensor.

FIG. 29 is a graphical representation of a photograph of a tested microsensor such as that depicted in FIG. 28. A U.S. penny (0.75" diameter) is shown for scale, highlighting the small size of the sensor.

Figure 30:
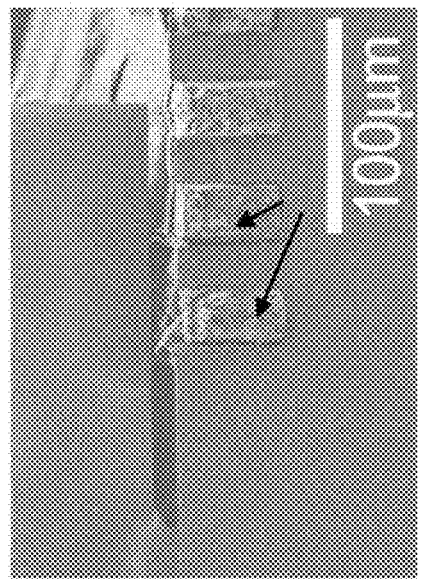
FIG. 30 shows a graphical representation of a micrograph of a cross-section of an example sensor.

FIG. 30 is a graphical representation of a micrograph showing a cross sectional view of the coils and air gap of the tested microsensor of FIG. 29.

Figure 31:
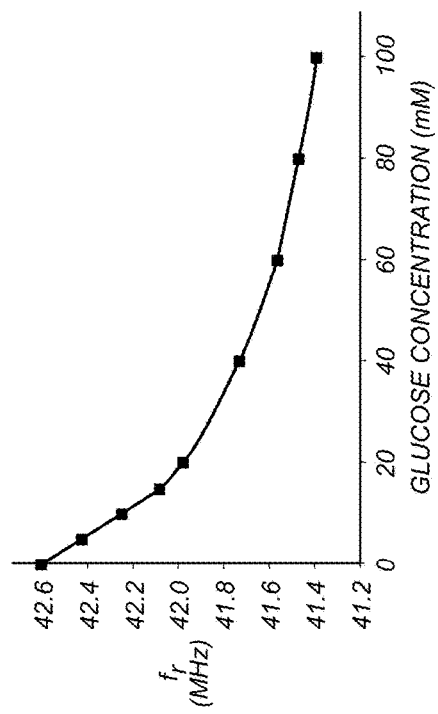
FIG. 31 shows experimental data of a tested microsensor.

FIG. 31 is a plot demonstrating that resonant frequency of the tested microsensor of FIG. 29 decreased with increasing glucose concentration. The trend reflects increased capacitance due to the top plate being pushed downward by the hydrogel. In some tests, 80-90 min was required to stabilize at equilibrium. For clinical use, up to 5-10 min is preferred.

Response time can be reduced by decreasing the thickness of all relevant components, including the hydrogel, rigid semipermeable membrane, and underlying glass diaphragm. Various aspects herein use islands of hydrogel to mitigate swelling pressures developed by the hydrogel, permitting establish secure long term bonding between elements. Various aspects herein use non-MEMS bonding procedures to reduce strain on polymer components of the sensor.

The response of PBA-based hydrogels to changes in glucose concentration was characterized and mathematically modeled, as well as pH and fructose, another sugar of interest.

Referring back to FIG. 4A, PBA is a Lewis acid. Upon binding an OH— ion (pK0=8.86), PBA is converted from a neutral to a charged form, which is stabilized by forming a reversible condensation complex with a sugar molecule through the latter's cis-diol. At physiological pH=7.4, PBA is mostly uncharged, at low sugar concentrations, but increasing sugar concentration increases hydrogel charge.

When the PBA moiety is incorporated into a polymer hydrogel, ionization leads to osmotic swelling forces. Under free swelling conditions, these forces can lead to substantial changes in hydrogel volume, which proceed until ionic swelling pressure is equalized by retractive pressures due to polymer elasticity and hydrophobic interactions between the hydrogel and the solvent.

The balance of swelling forces is normally accounted for by Flory-Rehner-Donnan-Langmuir (FRDL) theory, which under free swelling conditions predicts $$\ln(1-\phi)+\phi+\chi\phi^2+\rho_0\bar{v}_w[(\phi/\phi_0)^{1/3}-(\phi/2\phi_0)]- \bar{v}_w c_s(\lambda+1/\lambda-2)=0 \qquad 2$$

where $\phi$ is the volume fraction of polymer at equilibrium, $\phi_0$ is the volume fraction of polymer at synthesis, $\rho_0$ is proportional to the crosslink density at synthesis, $v_w$ is the partial molar volume of water (0.018 L/mol), $c_s$ is the salt concentration in the external solution (typically 0.155 mM), and $\chi$ is the Flory interaction parameter. The swelling ratio relative to synthesis is given by $Q=\phi_0/\phi$. The term $\lambda$ is the Donnan ratio, determined by properly assuming electroneutrality in the hydrogel:

$$(1-\phi)\bar{v}_s(\lambda-1/\lambda)-f\sigma_0(\phi/\phi_0)=0 \qquad 3$$

where $\sigma_0$ is the density (mol/volume of hydrogel) of ionizable PBA units at synthesis, and f is the fraction of these units that are ionized at a given pH and fructose concentration. Taking into account that pH inside the hydrogel differs from that in the external solution, the Donnan ratio can be used in the expression for f according to $$f = \frac{1}{1+\frac{\lambda 10^{-(pH-pK_0)}}{1+\frac{c_{sug}}{K_{sug}}}} \qquad (4)$$

Combining Eqs. (2), (3), and (4) enables prediction of swelling pressure under confinement, or degree of free swelling when the hydrogel is unconfined and $\Delta P=0$.

FIG. 4D demonstrates the ability of this model to predict the swelling behavior of PBA-based hydrogels as a joint function of pH and sugar concentration, with fructose used as a model sugar. This model, modified to account for reversible bridging of PBA groups by glucose, can be extended to describe glucose response.

In addition to the microvalve and microsensor work described above, various aspects include patterning and bonding of stimuli-sensitive hydrogels on silicon surfaces. In an example, a simple patterning method was demonstrated, in which hydrogels were synthesized and bonded on flat surfaces, dried and coated with photoresist. Standard chemical and plasma etch techniques were then used to remove hydrogel from all but the desired locations, with resulting feature sizes as small as 2 μm. The patterned hydrogels swelled perpendicular to the surface when exposed to the analyte, with lateral swelling constrained. Also, thin reflective metal films could be deposited on the initially dry hydrogel surfaces, providing a facile means to optically monitor swelling (not shown). In a variation on this theme, pH- and glucose sensitive hydrogels were introduced under an array of microcantilevers. Swelling in response to changes in analyte concentration led to distortion of the beams, which was readily detected by microinteferometry.

Figure 32:
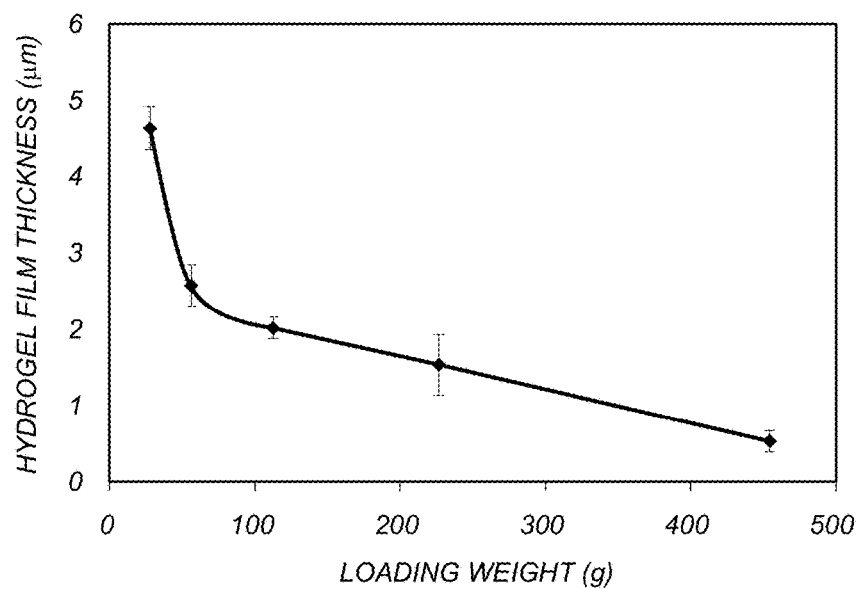
FIG. 32 shows experimental data of process options in making microsensors according to various aspects described herein.

Various aspects include a new method to prepare very thin hydrogel layers on glass substrates. Briefly, a glass slide is coated with an organosilane bonding agent. A drop of pregel solution containing monomers, crosslinker, and initiator is then placed on top and carefully covered with a transparency film, onto which weight is uniformly applied, squeezing the pregel into a thin uniform film whose thickness is inversely proportional to the resulting pressure, as shown in FIG. 32. Following polymerization, the weight and transparency film are removed, and the hydrogel is dried, followed by coating with a thin parylene layer. Subsequent deposition of photoresist, and sometimes Ti—Au layers, permits subsequent patterning.

Figure 33:
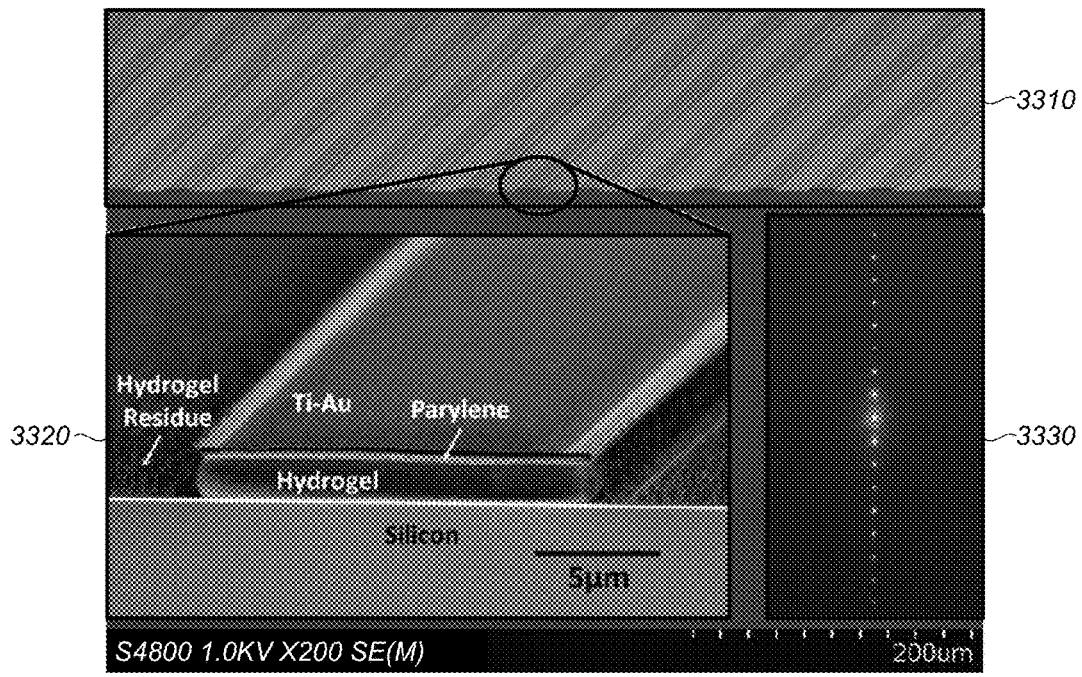
FIG. 33 shows graphical representations of a micrograph of a diffraction grating including a hydrogel, and of a diffraction pattern of the diffraction grating.

FIG. 33 shows a graphical representation of a micrograph (top) of a diffraction grating that was formed by this procedure, including inset 3320 showing hydrogel, parylene, and Ti—Au layers, plus a graphical representation of a laser diffraction pattern 3330 generated by the grating. Spot widths of this grating are swelling dependent, and can be used for analytical purposes.

Figure 34:
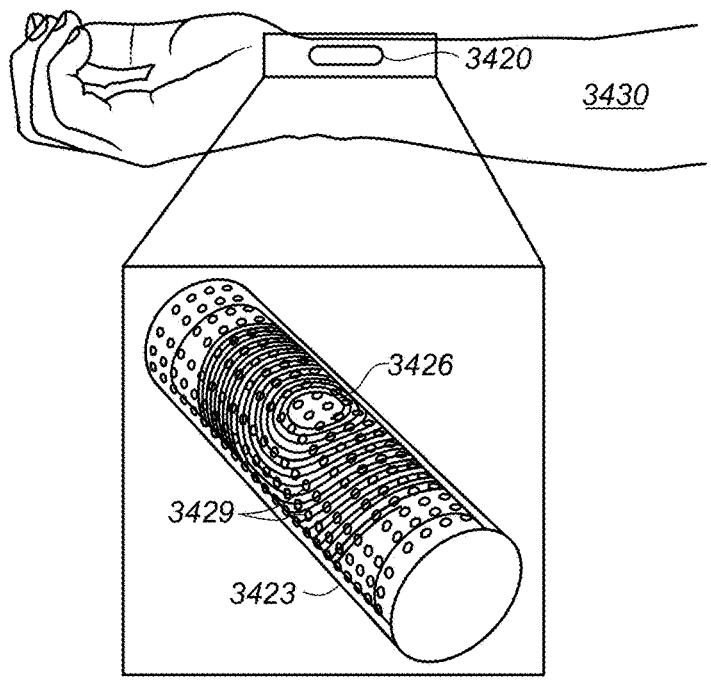
FIG. 34 shows a perspective of an implantable sensor.
Figure 35:
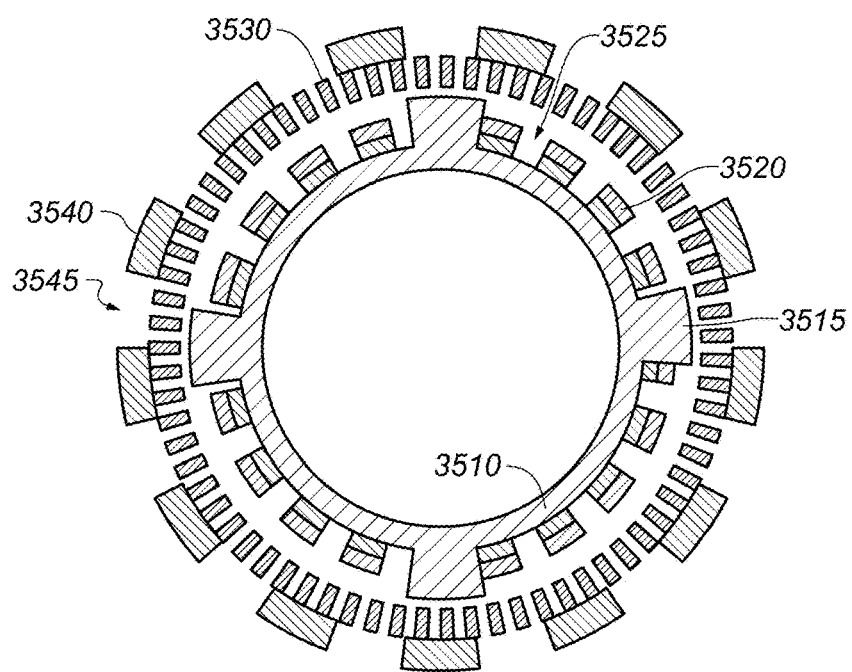
FIG. 35 shows a cross-section of an implantable sensor.

FIGS. 34 and 35 show a perspective and a radial (perpendicular to the long axis) cross-section of an example sensor 3420 device. The sensor 3420 is encapsulated in a perforated cylindrical outer shell 3423. The outer shell 3423 can be polymeric (Plexiglas, PEEK, PCL or other biocompatible material) and can be 2-3 mm in diameter and 10 mm in length (allowing for easy insertion using a large bore needle under local anesthesia) and implanted in subcutaneous tissue under skin 3430. Outer shell 3423 can be a tube configured to retain the substrate in a substantially cylindrical shape. The holes 3429 in the tube (50-100 µm in diameter) are laser drilled and large enough to allow easy access for interstitial fluid. The transponder is located inside the tube and includes a rolled planar coil 3426 with patterned PBA glucose sensitive ferrogel (not shown for clarity) on its surface. A thin membrane (not shown) with sub-micron pores (e.g., polycarbonate with a super-thin polyethylene glycol, PEG, coating to prevent biofouling) separates the hydrogel from the outer shell and prevents penetration of proteins and cells into the glucose sensitive part of the device. Various aspects provide a cylindrical form factor that is more attractive to physicians and patients than other form factors and allows easy implantation without the need for large incision required for a flat/planar structure such as that of FIG. 28.

The hydrogel structures in various aspects herein can be arranged as a thin layer (5-10 µm thick), improving the response time. The example sensor 3420 utilizes the change in the inductance of a planar coil 3426. Various aspects use the self-resonant frequency change of coil 3426 so do not require an additional separate capacitor to form the LC tank (parasitic capacitances of the coil itself play that role). Finally, the transponder can be fabricated from polymeric material and can be produced at low cost and with reduced need for cleanroom access.

Figures 38A, 38B, 38C:
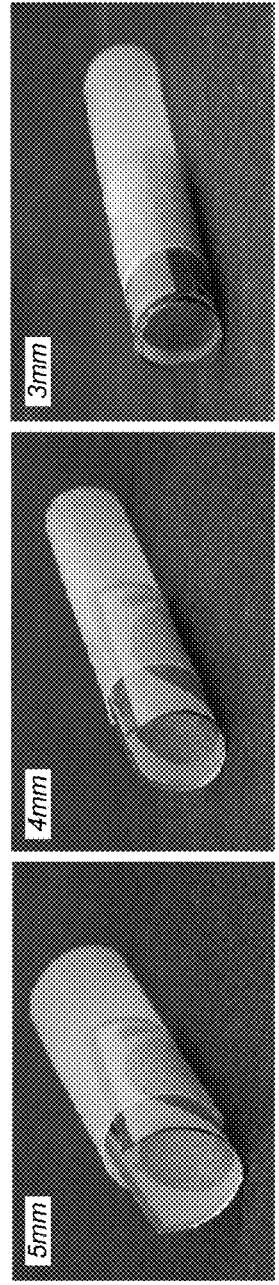
FIGS. 38A-38C show graphical representations of photographs of some of the conditions graphed in FIG. 37.
Figure 39A:
FIGS. 39A-39G shows steps in an example process for making ferrogel sensors.
Figure 39B:
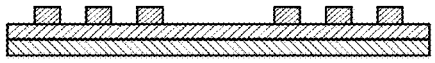
Figure 39C:
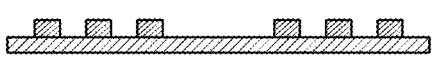
Figure 39D:
Figure 39E:
Figure 39F:
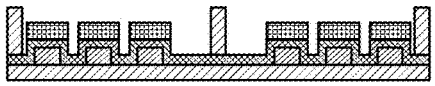
Figure 39G:
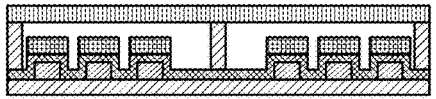

FIG. 34 is an example perspective of an implantable sensor 3420 that can be implanted, e.g., under the skin 3430 of a person. The substrate is formed or retained in a cylindrical shape. Further examples of cylindrical sensors are shown in FIGS. 38A, 38B, and 38C.

FIG. 35 shows substrate 3510 with spacers or standoffs 3515 to support nanoporous membrane 3530. Ferrogel 3520 is arranged in islands between standoffs 3515. The islands are separated by gaps 3525 (selected region(s) of a hydrogel layer from which the hydrogel is sacrificed). Cylindrical shell 3540 is arranged outside membrane 3530 and has pores 3545 through which an analyte or solute can pass. The coil is not shown in this cross-section.

Figure 36A:
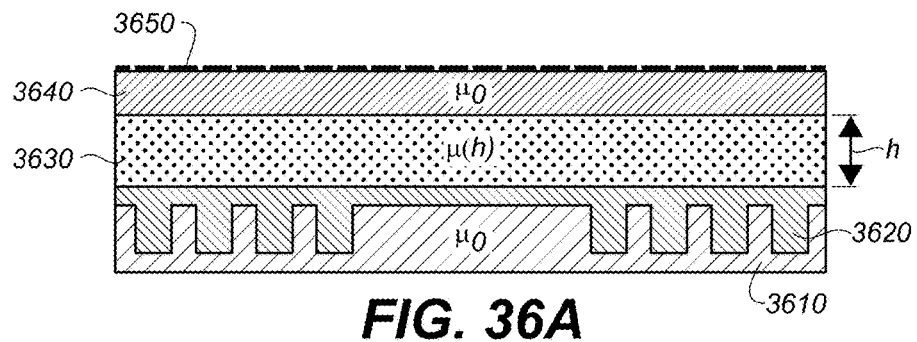
FIGS. 36A-36C show examples of the response of a hydrogel to an analyte.
Figure 36B:
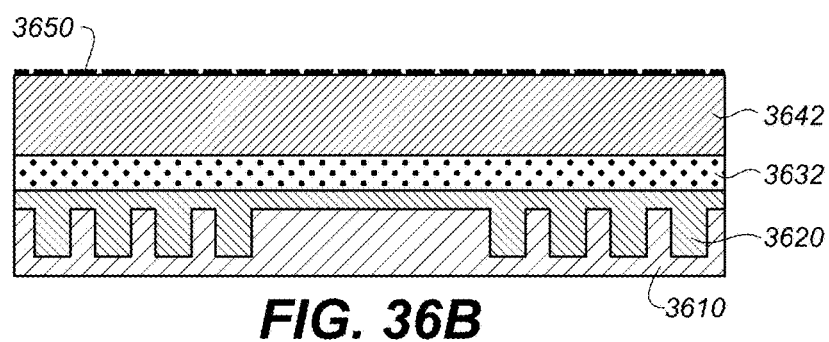
Figure 36C:
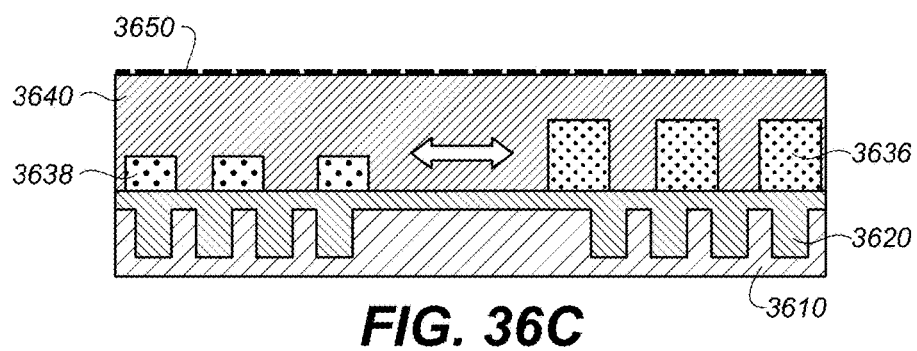

FIGS. 36A-36C show an example sensor. Inductor coil 3620 is embedded in dielectric substrate 3610 coated with waterproof film. Ferrogel 3630 of thickness h and containing ferrite nanoparticle inclusions is bonded to film but can expand into water or other contents of space 3640, below fluid- or solute-selective membrane 3650. Magnetic permeabilities above and below ferrogel are constant and equal to permeability of free space, $\mu_0$. Magnetic permeability $\mu$ of ferrogel depends on volume fraction of inclusions, which decreases inversely with increasing h. Inductance L and hence resonant frequency are determined by $\mu$ and h. Hydrogel swells or shrinks depending on glucose concentration, altering $\mu$, h, L, and fr. Ferrogel can be patterned onto substrate. Thin hydrogel islands swell and shrink more rapidly, as are porous hydrogels.

FIG. 36A is a cross section schematic of the sensor illustrating the substrate 3610, inductor coil 3620, and hydrogel 3630. The depiction is planar, though it should be recognized that the structures can be rolled onto a cylinder as in FIG. 34. The coil 3620 includes conductive metal fabricated in an insulating dielectric substrate (parylene or polyimide) and coated on top with a thin, waterproof insulating layer (not shown). The ferrogel 3630 is bonded on top of the coating and projects into the space 3640 below the nanoporous membrane 3650 (see FIG. 35). Space 3640 can, e.g., be filled with water when the sensor is implanted in a body. Due to bonding, changes in hydrogel swelling are manifested by a change in hydrogel thickness, h, from an initial, "reference" thickness h0. The ferrogel can include immobilized $Fe_3O_4$ SPNs. The magnetic permeability, $\mu$, of the ferrogel can vary according to a function $$\mu(h,h_0,\theta_0)=\mu_0+\Delta\mu(\theta_0 h_0/h), \quad (5)$$

where $\theta_0$ is the loading (v/v) of ferroparticles in the initial hydrogel configuration, and $\mu_0$ is the permeability of free space, which also applies to the nonmagnetic structures above and below the ferrogel. The inductance of the whole system, and hence and resonant frequency, can depend on h, $\mu(h, h_0, \theta_0)$, and the geometry and number of coil windings.

FIG. 36B shows the sensor of FIG. 36A after hydrogel 3632 has shrunk. Space 3642 is now larger as a result, in this example. When the hydrogel swells or shrinks in response to a change in glucose concentration, resonant frequency can change.

FIG. 36C shows a sensor configuration in which the ferrogel is patterned on the surface. Patterned ferrogel can swell/shrink more rapidly that a flat sheet hydrogel of equal thickness. As mentioned above this can also relax the built in stress in the hydrogel film and improve sensor stability. In the illustrated example, hydrogel 3636 represents a swollen state and hydrogel 3638 represents a shrunken state. Hydrogels can be made highly porous, increasing mass transfer and hence speed of response. In some examples, the swelling of patterned hydrogels may not be completely unidirectional. For example, flanging may occur at the top, especially if the pattern feature sizes are comparable to the hydrogel thickness.

In some aspects described herein, the sensor further includes a substrate and a membrane arranged to form a cavity in which the hydrogel is located and can swell or shrink, wherein the membrane is configured to allow passage of a fluid across the membrane and block passage of particles of a predetermined size that are suspended in the fluid. In some examples, the hydrogel, the substrate, and the membrane are configured so that the hydrogel does not completely fill the cavity. The electrical property of the sensor can be resonant frequency or inductance. The condition can be moisture, temperature, pH, concentration of glucose, or concentration of a selected metal ion.

A custom fabricated planar copper coil (10 mm diameter) was embedded in insulating polyimide film, and was placed on top of a GelBond® PAG sheet (Lonza Rockland). Latex beads including $Fe_3O_4$ SPNs dispersed in a polystyrene matrix and coated with surfactant (ProMag™, Bangs Laboratories: 1 μm diameter) were suspended in an aqueous pregel solution containing poly (methacrylic acid-co-acrylamide) (MAA/AAm, 5 mol % MAA), crosslinker and initiator. Using the squeeze film technique described above (FIG. 32), the suspension was polymerized onto the substrate, producing a ferrogel that completely covered the coil film, and bonded covalently to the GelBond® PAG sheet, trapping the coil. The ferrogel was dried and determined to be approximately 5 μm thick in its dry state. The dried ferrogel was patterned by a laser cutter into small squares of 130 μm widths with 200 μm spacing between the ferrogel blocks. Subsequently, the ferrogel was swelled in DI water overnight prior to testing in pH buffers. FIG. 20 shows a block diagram of the experimental setup. FIG. 19 shows the tested fabrication process.

Following rehydration of the ferrogel, this construct was tested in aqueous buffers at varying pH staircases. The device was exposed to the solutions of alternating pH levels between 4 and 6, FIG. 25. A decrease in frequency was observed as pH increased, as expected due to an increase in the thickness and shape change of the ferrogel, resulting from the increased ionization of the MAA groups. On the other hand, the resonant frequency increased when pH was lowered, consistent with a decrease in ferrogel thickness. The following reversible response in resonant frequency were observed after exposure for 15 minutes with the shifts in resonant frequency when changed from pH 4 to pH 5, $\Delta f_{res}$=2.04 MHz; from pH 5 to pH 6, $\Delta f_{res}$=1 MHz. The sensor displayed a reversible pH response with no drift and was able to measure much smaller pH changes, as shown in FIG. 26. For example, changing from pH 4.0 to pH 4.1 yielded $\Delta$fres=0.26 MHz.

FIG. 37 shows measured data of phase as a function of frequency, with phase minima corresponding to the resonant frequency. Data are shown for a flat sensor (curve 3701) and the sensor rolled into cylinders of three diameters, 5, 4, and 3 mm (curves 3705, 3704, and 3703, respectively).

FIGS. 38 A-C are graphical representations of photographs of the planar-coil sensor rolled into a cylindrical shape and inserted into a perforated tube, as shown in FIGS. 34 and 35. A planar structure can be used in the fabrication and preceding design process, simplifying sensor manufacturing. The rolling process increases the self-resonant frequency by decreasing the inductance, as shown in FIG. 37. For example, curve 3703, the tightest diameter, has the highest resonant frequency at ~300 MHz, compared to ~220 MHz for the flat sensor, curve 3701.

Various aspects include a flexible inductor, coated with a patterned thin layer of glucose sensitive ferrogel; a process to fabricate the sensor and incorporate it into a perforated cylindrical tube targeted for subcutaneous implantation; and in vitro use of the device in PBS glucose solutions.

The sensitivity of the disclosed sensor depends on the coil design (dimensions, number of turns, turn width and separation), the propensity of the ferrogel to swell and shrink as a function of glucose concentration, and the change in magnetic properties of ferrogel in its swollen and shrunken states, e.g., the concentration and distribution of SPNs in the ferrogel covering the coil. The spatial distribution of patterned ferrogel over the sensor can be chosen such that the magnetic flux from the coil couples efficiently with the ferrogel. COMSOL® or other multiphysics simulations can be used in determining design parameters.

Various aspects include at least one of two types of ferrogels. The first type can be based on the directly glucose sensitive hydrogels containing the phenylboronic acids described above (FIG. 4A). The second type can be based on pH-sensitive hydrogels into which the enzymes glucose oxidase, catalase, and gluconolactonase are immobilized. In the presence of these enzymes, glucose is converted to hydrogen ion (H+) causing a lowering of local pH from its physiological set point. Amine-based hydrogels whose swelling degrees increase as local pH is reduced from pH 7.4 to 6.8 can be used.

Ferrogels can be synthesized by standard solution free radical copolymerization, with monomer ratios, crosslinker concentration, solvent concentration and concentration of SPNs (either individually functionalized for incorporation in the network or incorporated into latex beads as described above), as degrees of freedom for synthesis. When enzymes are incorporated, they can be pre-acrylated and hence incorporated directly into the polymer network. Enzymes can be incorporated at excess concentrations, and their stability can enhanced by their immobilization and by the presence of catalase, which removes $H_2O_2$ and other reactive oxygen species that are known to degrade enzyme performance.

Various aspects include synthesizing, in parallel to the patterned arrays (FIG. 21), small samples that are unanchored and hence free to swell in all directions. These samples, which can be synthesized in capillary tubes, can be tested for their swelling characteristics, permitting extraction of parameters relevant to the FRDL swelling model of Eqs. (2), (3), and (4). With these parameters in hand, it may be possible to predict the swelling of anchored hydrogels using COMSOL®. As noted before, the aspect ratio (height/base width) of the ferrogels at rest may affect the ultimate shape following swelling. The hydrogels may flange out on top, and the density of SNPs may become nonuniform throughout the hydrogel whereas they were initially uniform. Profilimetry and side-view microscopy can be used when possible to characterize the shape of swollen but tethered hydrogels.

Once the polymer concentration profile, (x, y, z) is determined in the swollen hydrogel, the local magnetic permeability can be modeled using the Bruggeman effective medium equation. According to this equation, which holds for many properties of composite materials, the magnetic permeability inside the ferrogel, $\mu f(x, y, z)$, is given in terms of the permeability of nonmagnetizable materials, $\mu_0$, the permeability of the SNPs, $\mu_{SNP}$, and the volume fraction of SNPs at hydrogel synthesis, $\theta_0$, by $$\left(\frac{\phi}{\phi_0}\right)\theta_0\left(\frac{\mu_{SNP}-\mu_f}{\mu_{SNP}-2\mu_f}\right)+\left[1-\left(\frac{\phi}{\phi_0}\right)\theta_0\right]\left(\frac{\mu_0-\mu_f}{\mu_0-2\mu_f}\right)=0 \quad (6)$$

Eq. (6) may be used with ferrogels based on covalently attached SNPs, since they may be uniformly dispersed. For ferrogels containing SNPs incorporated inside latex beads, it may be necessary to iterate Eq. (6), first treating the beads as effective media with a given concentration of SNPs and estimating their permeability, and then using this value plus the bead volume fraction to determine the final answer. This model can be checked against experiment, either by altering degree and mode of incorporation of SPNs, or by measuring magnetic permeabilities of the same ferrogel but at different swelling degrees.

The model and measurements just described can provide a picture of the magnetic permeability distribution within a single ferrogel patch. This distribution, along with the spatial patterning of the patches on the magnetic coil substrate, can determine the magnetic coupling (i.e. inductance) of the hydrogel/coil device, in either its planar or cylindrically wrapped form. Integration of this information can again be carried in COMSOL®, allowing prediction of resonant frequency. The modeling may include determining stationary response following a stimulus, i.e. prediction of resonant frequency when the hydrogel has reached its equilibrium. Dynamic aspects can be modeled later, using appropriate mass transfer and poroelastic equations, which may also be coded in COMSOL®.

An important design parameter is the interrogation range. Passive LC transponders suffer from a short readout distance (1-2 cm depending on the relative size of the interrogating and implanted coils). Due to the shallow subcutaneous implantation depth of the disclosed sensor, the interrogation range may not be a major issue. However, the rolled planar coil can have a different flux coupling to the outside inductor which can influence the interrogation range and alignment issues. In experiments shown in FIGS. 37 and 38A-C, more significantly improved results were obtained when the center of the rolled coil was coinciding with the center of a flat, single turn interrogating wire.

FIGS. 39A-39G show steps in a fabrication process of a sensor. Various aspects herein include fabricating a thin (5-10 µm) ferrogel layer with good adhesion to the underneath polymeric inductor. FIGS. 39A-G show process steps in a disclosed sequence in which the coil is first fabricated on a polyimide (or parylene) layer (a silicon wafer is used for easy handling and can be released from the structures at the very end) followed by a low temperature atomic layer deposition (ALD) of a good quality dielectric ($SiO_2$ or $Al_2O_3$). ALD allows for deposition of a high quality inorganic oxide that is needed for adhesion of the ferrogel to the coil while simultaneously retains the flexibility of the structure. Then, the oxide surface is silanized and ferrogel is squeeze-cast (see FIG. 32) on top of the coil and laser-patterned into smaller islands. Subsequently a double-sided adhesive-coated polyimide tape (50-100 µm thick) is laser patterned and bonded to the coil to form posts surrounding the ferrogel plugs (such posts are necessary to allow for vertical swelling of the ferrogel and separating its top surface from the nanoporous membrane and outside polymeric capsule). Finally, a polycarbonate nanoporous membrane (pores<1 µm) coated with a thin layer (<0.1 µm) of PEG is bonded to the top layer, completing the fabrication of the planar coil. One fabricated, the coil is rolled into a cylindrical shape and inserted into a perforated polymeric tube (FIGS. 34 and 35) and the ends of the tube is sealed using epoxy.

In vitro tests were performed in PBS glucose solution in order to characterize and evaluate the ferrogel sensor for targeted design metrics. In various aspects, sensors herein have a dynamic range of 2-20 mM (39-3900 mg/dL) covering hypoglycemic (<2 mM), normoglycemic (4-7 mM), and hyperglycemic (7-20 mM) scenarios associated with diabetes; a resolution of 0.1 mM; an accuracy of 10%; and a drift of <1 mM/month. Various sensors herein have a response time is <5 minutes which is fast enough to record most blood glucose fluctuations.

Figure 40:
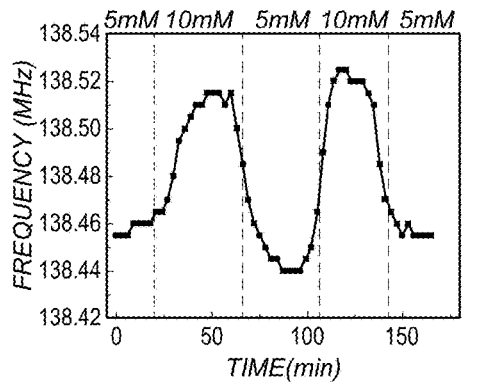
FIG. 40 shows measured data of a tested example sensor.

FIG. 40 shows measured data of resonant frequency of a tested sensor over a time series of glucose-concentration steps. A glucose-sensitive hydrogel in which magnetic beads were physically entrapped was used. The tested time series alternated between 5 mM and 10 mM glucose concentrations.

Figure 41:
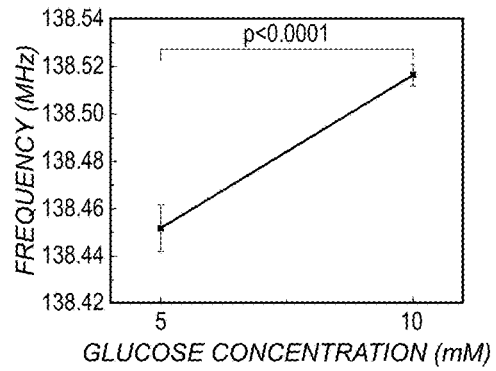
FIGS. 41-43 show statistics of data collected from various experiments.

FIG. 41 shows results of a statistical analysis of the data shown in FIG. 40. The tested sensor had a sensitivity of 12.61 kHz/mM and a resolution of 0.4 mM. The sensor had a response time of ~10 min for both rise (increasing glucose concentration) and fall (decreasing glucose concentration). The results are given in Table 2. The p-value<0.0001 indicates there is a statistically-significant difference between measurements at 5 mM and measurements at 10 mM.

TABLE 2

|  | Ferrogel | |
| --- | --- | --- |
| Glucose Con. [mM] | 5 | 10 |
| Freq [MHz] | 138.45 | 138.52 |
| Std. Dev. Freq [MHz] | 0.010 | 0.005 |

Figure 42:
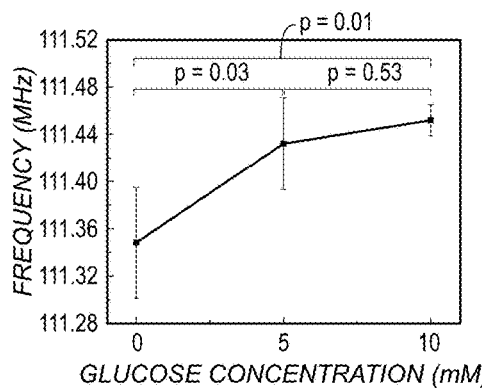
Figure 43:
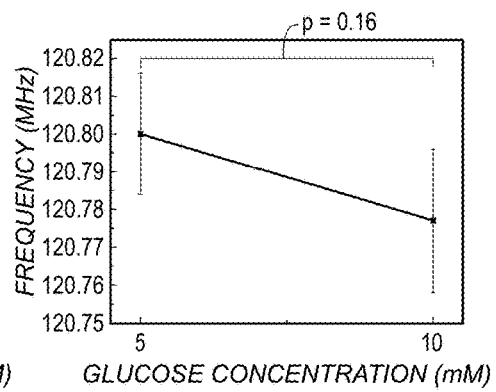

FIGS. 42 and 43 show results of control experiments that demonstrate the effectiveness of the ferrogel with coil as a glucose transducer. Experiments were performed using a coil alone, and using a coil with a hydrogel that did not include SPNs or other structures for modulating magnetic properties of the hydrogel. The results are given in Table 3.

TABLE 3

|  | Coil | | | Non-Ferrogel | |
| --- | --- | --- | --- | --- | --- |
| Glucose Con. [mM] | 0 | 5 | 10 | 5 | 10 |
| Freq [MHz] | 111.348 | 111.432 | 111.452 | 120.800 | 120.777 |
| Std. Dev. Freq [MHz] | 0.047 | 0.039 | 0.013 | 0.016 | 0.019 |
| p |  |  | 0.01 |  | 0.16 |
| p |  | 0.03 |  |  |  |
| p |  |  | 0.53 |  |  |

FIG. 42 shows results of an experiment in which a coil was tested with various glucose concentrations. As indicated by the depicted "p" values, there was no statistically-significant difference between the measurements at 5 mM and the measurements at 10 mM.

FIG. 43 shows results of an experiment in which a hydrogel without SPNs was tested with various glucose concentrations. As indicated by the depicted "p" values, there was no statistically-significant difference between the measurements at 5 mM and the measurements at 10 mM.

Figure 44:
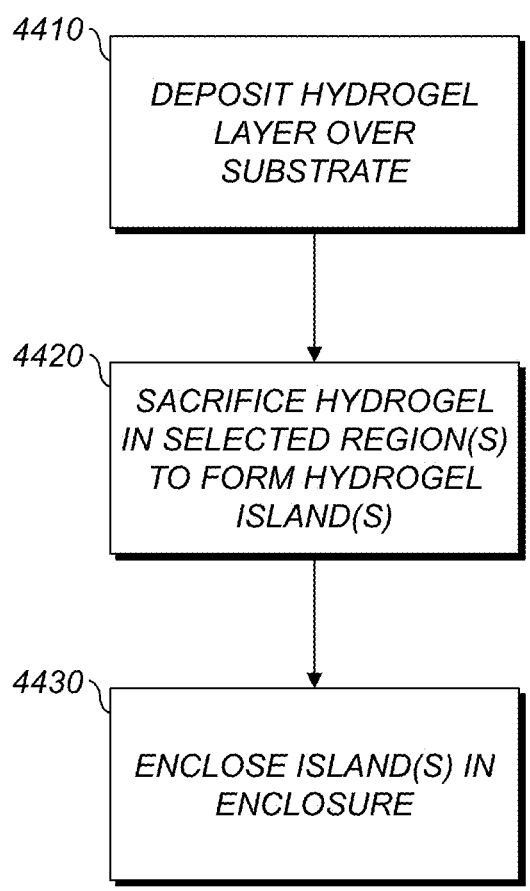
FIG. 44 is a flowchart illustrating an example process for making a ferrogel sensor.

FIG. 44 shows a flowchart illustrating an exemplary method for making a sensor. The steps can be performed in any order except when otherwise specified, or when data from an earlier step is used in a later step. In at least one example, processing begins with step 4410. For clarity of explanation, reference is herein made to various components described above that can carry out or participate in the steps of the exemplary method. It should be noted, however, that other components can be used; that is, exemplary method(s) shown in FIG. 44 are not limited to being carried out by the identified components. Similarly, steps of other flow diagrams herein may be performed in any order except under the conditions noted above, and references to specific components in the discussions of other flow diagrams here are exemplary and not limiting.

In step 4410, a layer of hydrogel is deposited over a substrate. The hydrogel is configured to change thickness or volume in response to a selected condition, as described above (e.g., FIGS. 21, 36C). The hydrogel includes a plurality of magnetic particles disposed in the hydrogel so that a magnetic property of the hydrogel changes with changes of thickness or volume of the hydrogel, also as described above.

In step 4420, the hydrogel is sacrificed in selected region(s) of the layer of hydrogel. As a result, hydrogel outside the selected region(s) forms a plurality of spaced-apart islands of the hydrogel. Sacrificing can include pattern-wise moving, destroying, ablating, eroding, evaporating, disintegrating, or otherwise removing hydrogel in the selected region(s). Step 4420 may include laser-cutting, shoveling, pushing aside, or grinding of the hydrogel. After step 4420, areas can exist between the islands of the hydrogel into which the hydrogel can swell. In some examples, the selected region(s) are shaped so that each island of hydrogel is substantially quadrilateral (e.g., square, rectangular, or parallelogram-shaped), triangular, otherwise polygonal (concave or convex), or circular. In some examples, the selected region(s) are arranged so the islands of hydrogel form a checkerboard pattern. In some examples, each island of hydrogel has a selected size in a selected direction, and the spaces between islands adjacent to each other along that direction are substantially equal to the selected size. For example, in a checkerboard pattern, at least some of the selected region(s) can be squares substantially the same size and shape as the islands.

In some examples, the sacrificing step 4420 includes removing hydrogel from the selected region(s) by laser patterning. Laser patterning processes such as laser ablation or laser drilling can be used. In some examples, the laser patterning includes irradiating the hydrogel with a laser having a substantially Gaussian spot.

In step 4430, the islands of the hydrogel are enclosed in an enclosure at least partly permeable to a selected fluid or to a selected solute. The fluid may include gas or liquid. The fluid may include a solute, solvent, or solution. Examples of enclosure are discussed above with reference, e.g., to FIGS. 1, 36A-36C.

Figure 45:
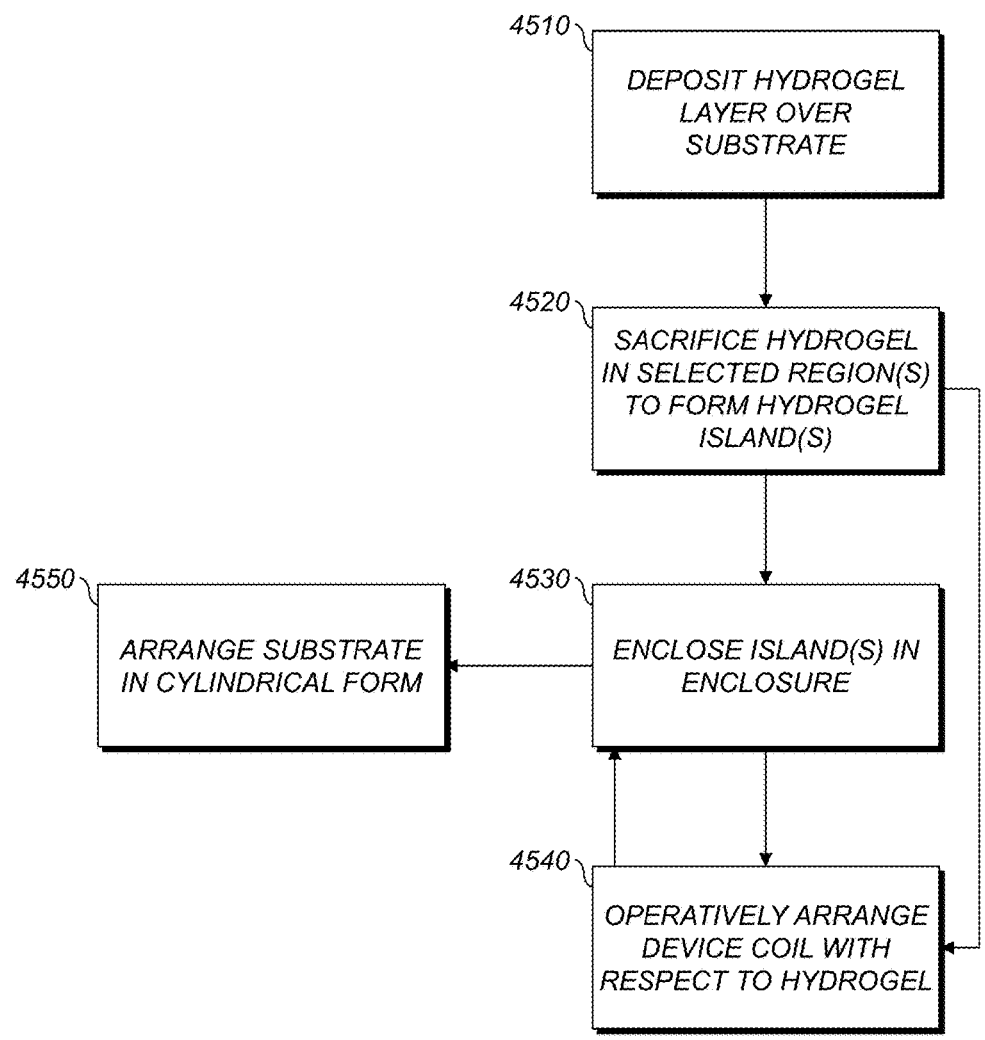
FIG. 45 is a flowchart illustrating example processes for making a ferrogel sensor.

FIG. 45 shows a flowchart illustrating an exemplary method for making a sensor. Steps 4510, 4520, and 4530 can correspond to steps 4410, 4420, and 4430, respectively. Steps 4520 or 4530 can be followed by step 4540. Step 4540 can be followed by step 4530. Step 4530 can be followed by step 4550.

In step 4540, a device coil is operatively arranged with respect to the hydrogel so that changes in the magnetic property modulate an electrical property of the sensor. In some examples, the selected region(s) of the layer of hydrogel at least partly overlay electrode(s) of the device coil. In an example, plugs or other shapes of ferrogel are arranged between lines of the device coil. The device coil can include, e.g., a smoothly-curved spiral, or an octagonal, square, or other pentagonal coil such as coils typically fabricated on semiconductor wafers.

In step 4550, the substrate is arranged in a substantially cylindrical form. Examples are discussed above with reference to FIGS. 34, 35, 37, and 38A-38C. As used herein, "cylindrical" includes configurations having radial cross-sections in the form of circular or elliptical arcs (e.g., FIG. 38A), circles, ellipses, or spirals, whether within circles or ellipses (e.g., FIG. 38C). In an example, step 4550 includes inserting the substrate into a substantially cylindrical tube, as discussed above.

Figure 46:
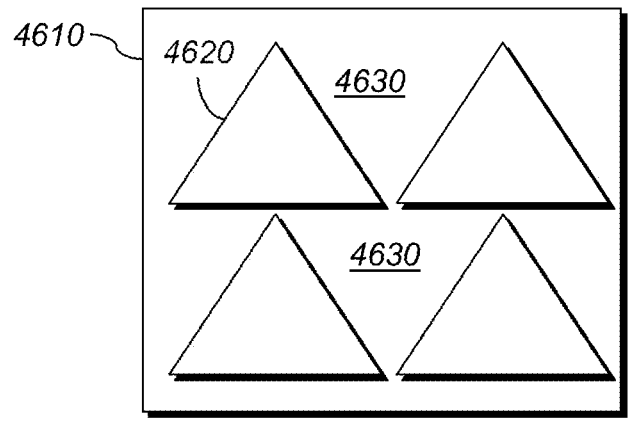
FIG. 46 is an example layout of ferrogel islands.

FIG. 46 shows an example arrangement of a sensor 4610. Islands 4620 of hydrogel are separated by selected region(s) 4630. In the illustrated example, region(s) 4630 are shaped so that islands 4620 are substantially triangular. For brevity, only one island 4620 is labeled.

Figure 47:
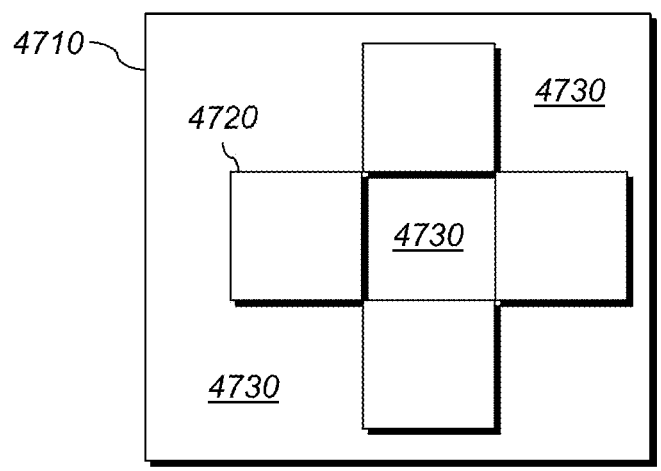
FIG. 47 is another example layout of ferrogel islands.

FIG. 47 shows an example arrangement of a sensor 4710. Islands 4720 of hydrogel are separated by selected region(s) 4730. In the illustrated example, region(s) 4730 are shaped so that islands 4720 substantially form a checkerboard pattern. For brevity, only one island 4720 is labeled. As used herein, islands 4720 and other islands described throughout are considered to be spaced apart if they are either fully isolated from each other or in substantially point contact only at sparsely-spread points (e.g., at their corners, as shown in this example).

Figure 48:
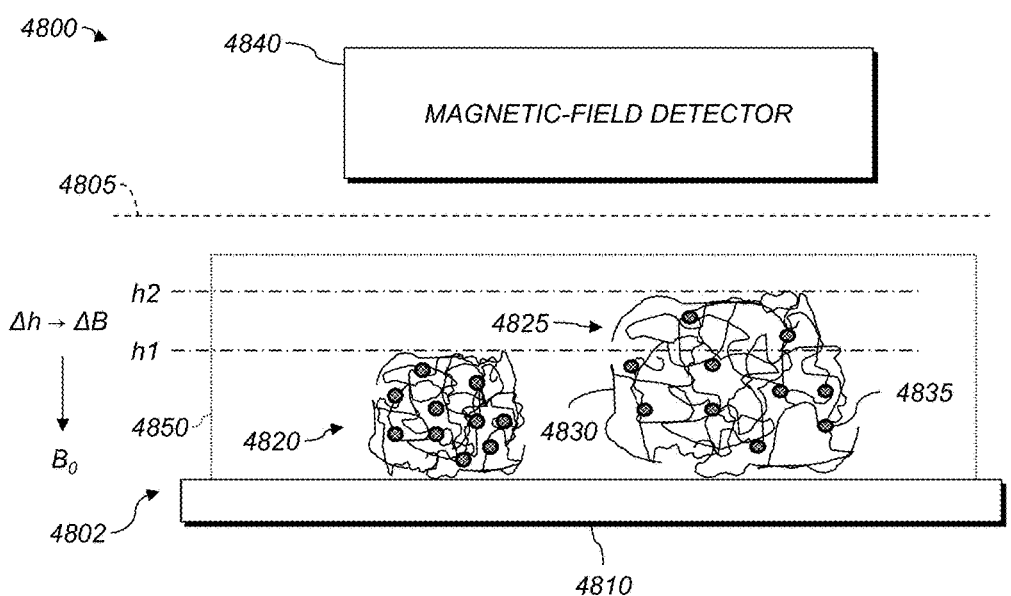
FIG. 48 is a schematic cross-section of a sensing system.

FIG. 48 shows a system 4800 for detecting a condition. System 4800 includes sensor 4802 and magnetic-field detector 4840. Sensor 4802 can be, e.g., implanted under skin 4805. The sensor includes substrate 4810 over which are arranged a plurality of spaced-apart islands 4820, 4825 of hydrogel 4830. Hydrogel 4830 is configured to change thickness or volume in response to the condition.

A plurality of magnetic particles 4835 is arranged in the hydrogel 4830 so that a magnetic field of the hydrogel 4830 changes with changes of thickness or volume of the hydrogel 4830. Magnetic-field detector 4840 is operatively arranged to measure the magnetic field of the hydrogel 4830.

In the illustrated example, island 4820 extends to a height $h_1$ off substrate 4810, and represents a shrunken condition of hydrogel 4830. Island 4820 extends to a height $h_2 > h_1$ off substrate 4810, and represents a swollen condition of hydrogel 4830. The difference $\Delta h = h_2 - h_1$ leads to a change $\Delta B$ in the magnetic field. A base magnetic field is $B_0$, e.g., externally applied using an electromagnet (not shown). Magnetic-field detector 4840, e.g., a Hall-effect sensor, can measure the resulting field $B_0 + \Delta B$ and determine $\Delta h$ and thus the measured property of the analyte.

In some examples, substrate 4810 is formed in a cylindrical shape. In some examples, the sensor includes a tube (not shown) configured to retain the substrate in a substantially cylindrical shape, e.g., as discussed above with reference to FIGS. 34, 35, 37, 38A-38C, and 45. In some examples, islands 4820, 4825 of hydrogel 4830 are configured as geometrical units, e.g., tetrahedral, cubic, octahedral, dodecahedral, icosahedral, or pyramidal shapes.

In some examples, membrane 4850 is arranged with respect to substrate 4810 to form cavity 4855 in which the hydrogel 4830 is located and can swell or shrink. Membrane 4850 is configured to allow passage of fluid across the membrane, along with an analyte therein (e.g., glucose), and block passage of particles of a predetermined size that are suspended in the fluid (e.g., proteins or cells).

The invention is inclusive of combinations of the aspects described herein. References to "a particular aspect" and the like refer to features that are present in at least one aspect of the invention. Separate references to "an aspect" (or "embodiment" or "version") or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. A sensor comprising:
   a substrate;
   a plurality of spaced-apart islands of hydrogel arranged over the substrate, the plurality of spaced-apart islands of hydrogel configured to change respective thicknesses or volumes in response to a condition;
   a plurality of magnetic particles arranged in the islands of hydrogel so that respective magnetic properties of the islands of hydrogel change with changes of respective thicknesses or volumes of the islands of hydrogel;
   a device coil arranged with respect to the islands of hydrogel so that changes in the respective magnetic properties of the islands of hydrogel cause changes in an electrical property of the sensor; and
   a tube retaining at least a portion of the substrate disposed at least partly within the tube in a substantially cylindrical shape, the tube having a first end, a second end opposite the first end, and a substantially cylindrical outer shell extending from the first end to the second end.

2. The sensor according to claim 1, wherein the respective magnetic properties are respective effective permeabilities and the electrical property is resonant frequency.

3. The sensor according to claim 1, wherein the substrate is formed in a cylindrical shape.

4. The sensor according to claim 1, wherein each island of the plurality of islands of hydrogel is configured as a geometrical unit.

5. The sensor according to claim 4, wherein the geometrical units include tetrahedral, cubic, octahedral, dodecahedral, icosahedral, or pyramidal shapes.

6. The sensor according to claim 1, further comprising a hydrogel layer, wherein each island of the plurality of islands of hydrogel is arranged in the hydrogel layer, and the device coil is a planar coil arranged substantially parallel to the hydrogel layer.

7. The sensor according to claim 1, wherein:
   the sensor further includes a membrane forming a cavity in which each island of the plurality of islands of hydrogel is located;
   each island of the plurality of islands of hydrogel can swell or shrink in the cavity; and
   the membrane is configured to allow passage of a fluid across the membrane and to block passage of particles of a predetermined size that are suspended in the fluid.

8. The sensor according to claim 7, wherein the islands of hydrogel, the substrate, and the membrane are configured so that the islands of hydrogel do not completely fill the cavity.

9. The sensor according to claim 1, wherein the condition is moisture, temperature, pH, concentration of glucose, or concentration of a selected metal ion.

10. The sensor according to claim 1, wherein the sensor is 2 mm-3 mm in diameter.

11. A system comprising:
    a sensor comprising:
      a substrate;
      a plurality of spaced-apart islands of hydrogel arranged over the substrate, each island of the islands of hydrogel configured to change a respective thickness or a respective volume in response to a condition;
      a plurality of magnetic particles arranged in at least some of the islands of hydrogel so that respective magnetic fields of the at least some of the islands of hydrogel change with changes of the respective thicknesses or the respective volumes of the at least some of the islands of hydrogel; and
      a tube retaining at least a portion of the substrate disposed at least partly within the tube in a substantially cylindrical shape, the tube having a first end, a second end opposite the first end, and a substantially cylindrical outer shell extending from the first end to the second end; and
    a magnetic-field detector configured to measure the magnetic field of the hydrogel.

12. The system according to claim 11, wherein the substrate is formed in a cylindrical shape.

13. The system according to claim 11, wherein each of the at least some of the islands of hydrogel is configured as a geometrical unit.

14. The sensor according to claim 13, wherein the geometrical units include tetrahedral, cubic, octahedral, dodecahedral, icosahedral, or pyramidal shapes.

15. The system according to claim 11, the sensor further including a membrane arranged to form a cavity in which each of the islands of hydrogel is located and can swell or shrink, wherein the membrane is configured to allow passage of fluid across the membrane and block passage of particles of a predetermined size that are suspended in the fluid.

16. The system according to claim 11, wherein the magnetic-field detector includes a Hall-effect sensor.

17. The system according to claim 11, wherein the sensor is 2 mm-3 mm in diameter.

18. A sensor comprising:
    a shell having a substantially cylindrical shape, wherein the shell has a plurality of holes therethrough;
    a hydrogel arranged within the shell and configured to change thickness or volume in response to a condition;
    a plurality of magnetic particles arranged in the hydrogel so that a magnetic property of the hydrogel changes with changes of the thickness or volume of the hydrogel; and
    a device coil arranged within the shell,
    wherein the device coil is arranged with respect to the hydrogel so that changes in the magnetic property of the hydrogel modulate an electrical property of the sensor.

19. The sensor according to claim 18, wherein:
    the sensor further comprises a substrate arranged within the shell; and
    the hydrogel comprises an island of the hydrogel arranged over the substrate.

20. The sensor according to claim 19, wherein the shell retains at least a portion of the substrate in a substantially cylindrical shape.

21. The sensor according to claim 18, wherein:
    the sensor further comprises a membrane configured to allow passage of fluid across the membrane and block passage of particles of a predetermined size that are suspended in the fluid; and
    the membrane is arranged at least partly between the holes and the hydrogel.

22. The sensor according to claim 18, wherein the magnetic property is effective permeability and the electrical property is resonant frequency.

23. The sensor according to claim 18, wherein:
    the shell forms a cavity containing the hydrogel; and
    the hydrogel does not completely fill the cavity.

24. The sensor according to claim 18, wherein hydrogel comprises a plurality of islands configured as respective geometrical units.

25. The sensor according to claim 18, wherein the geometrical units include tetrahedral, cubic, octahedral, dodecahedral, icosahedral, or pyramidal shapes.

* * * * *